(12) United States Patent
Nijjar et al.

(10) Patent No.: US 10,494,426 B2
(45) Date of Patent: *Dec. 3, 2019

(54) ANTI-TRANSTHYRETIN ANTIBODIES

(71) Applicants: PROTHENA BIOSCIENCES LIMITED, County Dublin (IE); UNIVERSITY HEALTH NETWORK, Toronto, Ontario (CA)

(72) Inventors: Tarlochan S. Nijjar, Orinda, CA (US); Avijit Chakrabartty, Vaughan (CA); Jeffrey N. Higaki, San Mateo, CA (US)

(73) Assignees: PROTHENA BIOSCIENCES LIMITED, Dublin (IE); UNIVERSITY HEALTH NETWORK, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,600

(22) Filed: Jan. 3, 2018

(65) Prior Publication Data
US 2018/0201670 A1    Jul. 19, 2018

Related U.S. Application Data

(60) Division of application No. 15/201,416, filed on Jul. 2, 2016, now Pat. No. 9,879,080, which is a
(Continued)

(51) Int. Cl.
A61K 39/00 (2006.01)
C07K 16/00 (2006.01)
(Continued)

(52) U.S. Cl.
CPC ......... *C07K 16/18* (2013.01); *G01N 33/6893* (2013.01); *G01N 33/6896* (2013.01);
(Continued)

(58) Field of Classification Search
None
See application file for complete search history.

(56) References Cited

U.S. PATENT DOCUMENTS 5,530,101 A    6/1996 Queen et al.
9,534,048 B2   1/2017 Chakrabartty et al.
(Continued)

FOREIGN PATENT DOCUMENTS

WO    WO 2010/030203 A1    3/2010
WO    WO 2014/124334 A2    8/2014
(Continued)

OTHER PUBLICATIONS

U.S. Appl. No. 15/201,423 Notice of Allowance and Examiner Initiated Interview Summary dated Mar. 6, 2019.
(Continued)

Primary Examiner — Aurora M Fontainhas
(74) Attorney, Agent, or Firm — Alston & Bird LLP

(57) ABSTRACT

The invention provides antibodies that specifically bind to transthyretin (TTR). The antibodies can be used for treating or effecting prophylaxis of diseases or disorders associated with TTR accumulation or accumulation of TTR deposits (e.g., TTR amyloidosis). The antibodies can also be used for diagnosing TTR amyloidosis and inhibiting or reducing aggregation of TTR, among other applications.

34 Claims, 22 Drawing Sheets
(2 of 22 Drawing Sheet(s) Filed in Color)
Specification includes a Sequence Listing.

Related U.S. Application Data continuation-in-part of application No. 15/009,666, filed on Jan. 28, 2016, now abandoned.

(60) Provisional application No. 62/266,557, filed on Dec. 11, 2015, provisional application No. 62/109,001, filed on Jan. 28, 2015.

(51) Int. Cl.
| | |
|---|---|
| *A61K 51/10* | (2006.01) |
| *A61P 25/00* | (2006.01) |
| *C07K 16/18* | (2006.01) |
| *G01N 33/68* | (2006.01) |

(52) U.S. Cl.
CPC .... *A61K 2039/505* (2013.01); *C07K 2317/24* (2013.01); *C07K 2317/34* (2013.01); *C07K 2317/565* (2013.01); *C07K 2317/567* (2013.01); *C07K 2317/76* (2013.01); *C07K 2317/92* (2013.01); *G01N 2800/28* (2013.01); *G01N 2800/32* (2013.01)

(56) References Cited

U.S. PATENT DOCUMENTS

| | | | |
|---|---|---|---|
| 9,731,292 | B2 | 8/2017 | Ermantraut et al. |
| 9,879,080 | B2 | 1/2018 | Nijjar et al. |
| 2014/0056904 | A1 | 2/2014 | Chakrabartty et al. |
| 2016/0039916 | A1 | 2/2016 | Jiang et al. |
| 2016/0251418 | A1 | 9/2016 | Liu et al. |
| 2016/0257736 | A1 | 9/2016 | Nijjar et al. |
| 2016/0257737 | A1 | 9/2016 | Liu et al. |
| 2016/0340419 | A1 | 11/2016 | Torikai et al. |
| 2016/0340420 | A1 | 11/2016 | Zhang et al. |
| 2016/0347832 | A1 | 12/2016 | Hosoi et al. |
| 2016/0355576 | A1 | 12/2016 | Grimm et al. |
| 2017/0015737 | A1 | 1/2017 | Nijjar et al. |
| 2017/0058023 | A1 | 3/2017 | Liu et al. |
| 2017/0121398 | A1 | 5/2017 | Nijjar et al. |

FOREIGN PATENT DOCUMENTS

| | | |
|---|---|---|
| WO | WO 2015/010118 A2 | 1/2015 |
| WO | WO 2015/092077 A1 | 6/2015 |
| WO | 2016/033326 A2 | 3/2016 |
| WO | WO 2016/120809 A1 | 8/2016 |
| WO | WO 2016/120810 A1 | 8/2016 |
| WO | WO 2016/120811 A1 | 8/2016 |
| WO | WO 2018/007922 A2 | 1/2018 |
| WO | WO 2018/007923 A2 | 1/2018 |
| WO | WO 2018/007924 A2 | 1/2018 |

OTHER PUBLICATIONS

Adekar, et al., "Inherent Anti-amyloidogenic Activity of Human Immunoglobulin γ Heavy Chains," *J Biol Chem*, 285(2):1066-74, (2010).
Almagro, et al., "Humanization of antibodies," *Frontiers in Bioscience*, 12:1619-1633, (Jan. 1, 2008).
Bergstrom, et al., "Surface exposed epitopes and structural heterogeneity of in vivo formed transthyretin amyloid fibrils," Biophysical Research Communications, 348:532-539 (2006).
Cardoso, et al., "Transthyretin Fibrillogenesis Entails the Assembly of Monomers: A Molecular Model for in Vitro Assembled Transthyretin Amyloid-like Fibrils," *J Mol Biol*, 317:683-95, (2002).
Chen, et al., "Endoplasmic Reticulum Proteostasis Influences the Oligomeric State of an Amyloidogenic Protein Secreted from Mammalian Cells," *Cell Chem Biol*, 23:1282-1293, (2016).
Dias-Santos, et al., "Macular and Iptic disc dedma and retinal vascular leakage in familal amyloid polyneuropathy with a transthyretin Val30Met mutation: a case report", *J Med Case Rep*, 8:327 (Oct. 4, 2014).

Galant, et al., "Substoichiometric inhibition of transthyretin misfolding by immune-targeting sparsely populated misfolding intermediates: a potential diagnostic and therapeutic for TTR amyloidosis," *Sci Rep*, 6:1-11, srep 25080, Apr. 28, 2016. [Retrieved from the Internet Feb. 27, 2017: <www.nature.com/scientificreports>].
Goldsteins, et al., "Exposure of cryptic epitopes on transthyretin only in amyloid and in amyloidogenic mutants," Proc. Natl. Acad. Sci. USA, vol. 96, pp. 3108-3113 (Mar. 1999).
Gustavsson, et al., "Antigenic Mapping of Transthyretin Purified from Plasma and Amyloid Fibrils and within in Situ Tissue Localizations," American Journal of Pathology, vol. 144, No. 6, pp. 1301-1311 (Jun. 1994).
Hernandez, et al., "Identification of new pathogenic candidates for diabetic mascular edema using fluorescence-based difference gel electrophoresis analysis", Diabetes Metab Res Rev, 29:499-506 (2013). [Retrieved from the Internet Mar. 8, 2017: https://www.researchgate.net/publication/236140050_Identification_of_new_pathogenic_candidates_for_diabetic_macular_edema_using_fluorescence-based_difference_gel_electrophoresis_analysis].
Higaki, et al., "Novel conformation-specific monoclonal antibodies against amyloidogenic forms of transthyretin," *Amyloid*, 23(2):86-97, (2016).
Hosoi, et al., "Novel Antibody for the Treatment of Transthyretin Amyloidosis," *J Biol Chem*, 291(48):25096-25105, (2016).
Jiang, et al., "An Engineered Transthyretin Monomer that Is Nonamyloidogenic, Unless It Is Partially Denatured," *Biochemistry*, 40(38):11442-11452, (2011).
Johnson, et al., "The Transthyretin Amyloidoses: From Delineating the Molecular Mechanism of Aggregation Linked to Pathology to a Regulatory-Agency-Approved Drug," *J Mol Biol*, 421:185-203, (2012).
Lai, et al., "The Acid-Mediated Denaturation Pathway of Transthyretin Yields a Conformational Intermediate That Can Self-Assemble into Amyloid," *Biochemistry*, 35(20):6470-6482, (1996).
Lashuel, et al., "Characterization of the Transthyretin Acid Denaturation Pathways by Analytical Ultracentrifugation: Implications for Wild-Type, V30M, and L55P Amyloid Fibril Formation," *Biochemistry*, 37(51):17851-17864, (1998).
Leger, et al., "Humanization of Antibodies," *Molecular Medicine and Medicinal Chemistry*, pp. 1-23, (Jan. 1, 2011).
Levites, et al., "A Human Monoclonal IgG That Binds Aβ Assemblies and Diverse Amyloids Exhibits Anti-Amyloid Activities In Vitro and In Vivo," *J Neurosci*, 35(16):6265-6276, (2015).
McCutchen, et al., "Comparison of Lethal and Nonlethal Transthyretin Variants and Their Relationship to Amyloid Disease," *Biochemistry*, 34(41):13527-13536, (1995).
Miroy, et al., "Inhibiting transthyretin amyloid fibril formation via protein stabilization," *Proc Natl Acad Sci USA*, 93:15051-15056, (1996).
O'Nuallain, et al., "Anti-amyloidogenic Activity of IgGs Contained in Normal Plasma," *J Clin Immunol*, 30 Suppl 1:S37-S42, (2010).
O'Nuallain, et al., "Conformational Abs recognizing a generic amyloid fibril epitope," *Proc Natl Acad Sci USA*, 99(3):1485-1490, (2002).
O'Nuallain, et al., "Localization of a Conformational Epitope Common to Non-Native and Fibrillar Immunoglobulin Light Chains," *Biochemistry*, 46(5):1240-1247, (2007).
Paul, "Fundamental Immunology" textbook under the heading "Fv Structure and Diversity in Three Dimensions," pp. 292-295, (1993).
PCT/IB2016/050414 International Preliminary Report on Patentability dated Aug. 1, 2017.
PCT/IB2016/050414 International Search Report and Written Opinion dated Apr. 25, 2016.
PCT/IB2016/050415 International Preliminary Report on Patentability dated Aug. 10, 2017.
PCT/IB2016/050415 International Search Report and Written Opinion dated Mar. 24, 2016.
PCT/IB2016/050416 International Preliminary Report on Patentability dated Aug. 10, 2017.
PCT/IB2016/050416 International Search Report and Written Opinion dated May 18, 2016.
PCT/IB2017/053984 International Search Report and Written Opinion dated Jan. 2, 2018.

(56) References Cited

OTHER PUBLICATIONS

PCT/IB2017/053991 International Search Report and Written Opinion dated Jan. 17, 2018.
PCT/IB2017/053991 Invitation to Pay Additional Fees dated Nov. 2, 2017.
Phay, et al., "IgG Conformer's Binding to Amyloidogenic Aggregates," *PLoS One*, 10(9):1-25, (2015).
Phay, et al., "Transthyretin Aggregate-Specific Antibodies Recognize Cryptic epitopes on Patient-Derived Amyloid Fibrils," Rejuvenation Research, vol. 17, No. 2, pp. 97-105 (2014).
Planque, et al., "Physiological IgM Class Catalytic Antibodies Selective for Transthyretin Amyloid," *J Biol Chem*, 289(19):13243-13258, (2014).
Planque, et al., "Specific Amyloid β Clearance by a Catalytic Antibody Construct," *J Biol Chem*, 290(16):10229-10241, (2015).
Quintas, et al., "Tetramer Dissociation and Monomer Partial Unfolding Precedes Protofibril Formation in Amyloidogenic Transthyretin Variants," *J Biol Chem*, 276(29):27207-27213, (2001).
Redondo, et al., "Search for Intermediate Structures in Transthyretin Fibrillogenesis: Soluble Tetrameric Tyr78Phe TTR Expresses a Specific Epitope Present Only in Amyloid Fibrils," J. Mol. Biol., 304, 461-470 (2000).
Rudikoff, et al., "Single amino acid substitution altering antigen-binding specificity," *Proc Natl Acad Sci USA*, 79(6):1979-1983, (1982).
Sharma, et al., "Identification of Autoantibodies against Transthyretin for the Screening and Diagnosis of Rheumatoid Arthritis", *PLoS One*, vol. 9, Issue 4, (Apr. 2014).
Su, et al., "Antibody therapy for familial amyloidotic polyneuropathy," *Amyloid*, 19(51):45-46, (2012).
Terazaki, et al., "Immunization in familial amyloidotic polyneuropathy: counteracting deposition by immunization with a Y78F TTR mutant," Laboratory Investigation, 86, 23-31 (2006).
U.S. Appl. No. 15/201,416 Restriction Requirement dated May 31, 2017.
U.S. Appl. No. 15/201,423 Non-Final Office Action dated Oct. 19, 2017.
U.S. Appl. No. 15/201,423 Restriction Requirement dated Jun. 5, 2017.
U.S. Appl. No. 15/201,429 Non-Final Office Action dated Nov. 14, 2017.
U.S. Appl. No. 15/201,429 Restriction Requirement dated Jul. 3, 2017.
U.S. Appl. No. 15/009,662 Examiner Initiated Interview Summary dated Mar. 7, 2017.
U.S. Appl. No. 15/009,662 Non-Final Office Action dated Mar. 7, 2017.
U.S. Appl. No. 15/009,662 Restriction Requirement dated Sep. 20, 2016.
U.S. Appl. No. 15/009,666 Examiner Initiated Interview Summary dated Mar. 6, 2017.
U.S. Appl. No. 15/009,666 Non-Final Office Action dated Mar. 6, 2017.
U.S. Appl. No. 15/009,666 Restriction Requirement dated Sep. 20, 2016.
U.S. Appl. No. 15/009,667 Non-Final Office Action dated Mar. 29, 2017.
U.S. Appl. No. 15/009,667 Restriction Requirement dated Dec. 30, 2016.
U.S. Appl. No. 15/201,429 Final Office Action dated Jul. 9, 2018.
U.S. Appl. No. 15/201,423 Notice of Allowance and Examiner Initiated Interview Summary dated Jun. 13, 2018.
U.S. Appl. No. 15/201,429 Advisory Action dated Sep. 17, 2018.
U.S. Appl. No. 15/201,423 Notice of Allowance and Examiner Initiated Interview Summary dated Oct. 12, 2018.
PCT/IB2017/053987 International Preliminary Report on Patentability dated Jan. 8, 2019.
PCT/IB2017/053991 International Preliminary Report on Patentability dated Jan. 8, 2019.
PCT/IB2017/053984 International Preliminary Report on Patentability dated Jan. 8, 2019.
PCT/US2018/054723 International Search Report and Written Opinion dated Jan. 3, 2018.
Ionis Pharmaceuticals Announces Phase 3 NEURO-TTR Study of Inotersen (IONIS-TTRRx) Meets Both Primary Endpoints, Press Release, Carlsbad California, May 15, 2017.
PCT/US2018/062902 International Search Report and Written Opinion dated Apr. 7, 2019.
PCT/US2018/054720 International Search Report and Written Opinion dated Feb. 12, 2019.
Schonhoft, et al., "Peptide probes detect misfolded transthyretin oligomers in plasma of hereditary amyloidosis patients," Sci. Tranl. Med., 9, eaam 7621, (2017).
U.S. Appl. No. 15/201,429 Non-Final Office Action dated Mar. 5, 2019.
U.S. Appl. No. 15/201,423 Notice of Allowance dated Jun. 12, 2019.
Damas, et al., "Review: TTR Amyloidosis-Structural Features Leading to Protein Aggregation and Their Implications on Therapeutic Strategies," Journal of Structural Biology, 120, pp. 290-299, (2000).
U.S. Appl. No. 16/129,618 Non-Final Office Action and Interview Summary dated Aug. 22, 2019.
Carvalho, et al., "Liver Transplantation in Transthyretin Amyloidosis: Issues and Challenges," Liver Transplantation, 21:282-292, (2015).

```
                         10        20        30        40
                         |         |         |         |
m6C1VH      EVQLVESGGGLVQPGGSLKLSCAASGFTFSNYYMSWRQT  40
2OTU_B.pro  QVQLQESGGGLVQPGGSLKLSCAASGFTFRDYYMYWVRQT  40
ADX65650    EVQLVESGGGLVQPGGSLRLSCAASGFTFSSYEMNWVRQA  40
Hu6C1VHv1   EVQLVESGGGLVQPGGSLRLSCAASGFTFSNYYMSWVRQA  40
Hu6C1VHv1b  EVQLVESGGGLVQPGGSLRLSCAASGFTFSNYYMSWVRQA  40
Hu6C1VHv2   EVQLVESGGGLVQPGGSLRLSCAASGFTFSNYYMSWVRQA  40
Hu6C1VHv2b  EVQLVESGGGLVQPGGSLRLSCAASGFTFSNYYMSWVRQA  40
Hu6C1VHv3   EVQLVESGGGLVQPGGSLKLSCAASGFTFSNYYMSWVRQA  40
Hu6C1VHv3b  EVQLVESGGGLVQPGGSLKLSCAASGFTFSNYYMSWVRQA  40

50        60        70        80
                         |         |         |         |
m6C1VH      PEKRLEWVAYISIDGNNIYHPDSVKGRFTISRDNAKNTLY  80
2OTU_B.pro  PEKRLEWVAFISNGGSTYYPDTVKGRFTISRDNAKNTLY   80
ADX65650    PGKGLEWVSMISSSGSTIYYADSVKGRFTISRDNAKNSLY  80
6C1VHv1     PGKGLEWVSYISIDGNNIYHPDSVKGRFTISRDNAKNTLY  80
Hu6C1VHv1b  PGKGLEWVSYISIDGNNIYHPDSVKGRFTISRDNAKSTLY  80
Hu6C1VHv2   PGKGLEWVAYISIDGNNIYHPDSVKGRFTISRDNAKNTLY  80
Hu6C1VHv2b  PGKGLEWVAYISIDGNNIYHPDSVKGRFTISRDNAKSTLY  80
Hu6C1VHv3   PGKRLEWVSYISIDGNNIYHPDSVKGRFTISRDNAKNTLY  80
Hu6C1VHv3b  PGKRLEWVAYISIDGNNIYHPDSVKGRFTISRDNAKNTLY  80

90       100       110
                         |         |         |
m6C1VH      LQMSSLKSEDTAMYYCARDSDYGYFDVWGTGTTVTVSS  118  (SEQ ID NO:1)
2OTU_B.pro  LQMSRLKSEDTAMYYCARGRGYVWFAYWGQGTTVTVSS  118  (SEQ ID NO:2)
ADX65650    LQMNSLRAEDTAVYYCARDLSGSYYGYWGQGTLVTVSS  118  (SEQ ID NO:3)
Hu6C1VHv1   LQMNSLRAEDTAVYYCARDSDYGYFDVWGQGTLVTVSS  118  (SEQ ID NO:4)
Hu6C1VHv1b  LQMNSLRAEDTAVYYCARDSDYGYFDVWGQGTLVTVSS  118  (SEQ ID NO:5)
Hu6C1VHv2   LQMSSLRAEDTAVYYCARDSDYGYFDVWGQGTLVTVSS  118  (SEQ ID NO:6)
Hu6C1VHv2b  LQMSSLRAEDTAVYYCARDSDYGYFDVWGQGTLVTVSS  118  (SEQ ID NO:7)
Hu6C1VHv3   LQMNSLKAEDTAMYYCARDSDYGYFDVWGQGTLVTVSS  118  (SEQ ID NO:8)
Hu6C1VHv3b  LQMNSLKAEDTAMYYCARDSDYGYFDVWGQGTLVTVSS  118  (SEQ ID NO:9)
```

FIG. 1

```
                      10        20        30        40
                      |         |         |         |
m6C1VL         DVLMTQTPLSLPVSLGDQASISCRSSQSIVHSNGNTYLEW  40
3EYS_L_S-.pro  DVLMTQTPLSLPVSLGDQASISCRSSQSIVHSNGNTYLEW  40
ABI74084       DIVMTQTPLSLPVTPGEPASISCRSSQSLLHSNGYNYLDW  40
Hu6C1VLv1      DVVMTQTPLSLPVTPGEPASISCRSSQSIVHSNGNTYLEW  40
Hu6C1VLv2      DIVMTQTPLSLPVTPGEPASISCRSSQSIVHSNGNTYLEW  40

50        60        70        80
                      |         |         |         |
m6C1VL         YLQKRGQSPKLLIYKVSKRFSGVPDRFSGSGSGTDFILKI  80
3EYS_L_S-.pro  YLQKPGQSPKLLIYKVSNRFSGVPDRFSGSGSGTDFTLKI  80
ABI74084       YLQKPGQSPQLLIYLGSNRASGVPDRFSGSGSGTDFTLKI  80
Hu6C1VLv1      YLQKPGQSPKLLIYKVSKRFSGVPDRFSGSGSGTDFTLKI  80
Hu6C1VLv2      YLQKPGQSPKLLIYKVSKRFSGVPDRFSGSGSGTDFTLKI  80

90       100       110
                      |         |         |
m6C1VL         SRVEAEDLGVYYCFQGSHVPLTFGGGTKLELK  112 (SEQ ID NO:13)
3EYS_L_S-.pro  SRVEAEDLGVYYCFQGSHVPLTFGAGTKLELK  112 (SEQ ID NO:14)
ABI74084       SRVEAEDVGVYYCMQGLQTPLTFGGGTKVEIK  112 (SEQ ID NO:15)
Hu6C1VLv1      SRVEAEDVGVYYCFQGSHVPLTFGGGTKVEIK  112 (SEQ ID NO:16)
Hu6C1VLv2      SRVEAEDVGVYYCFQGSHVPLTFGGGTKVEIK  112 (SEQ ID NO:17)
```

FIG. 2

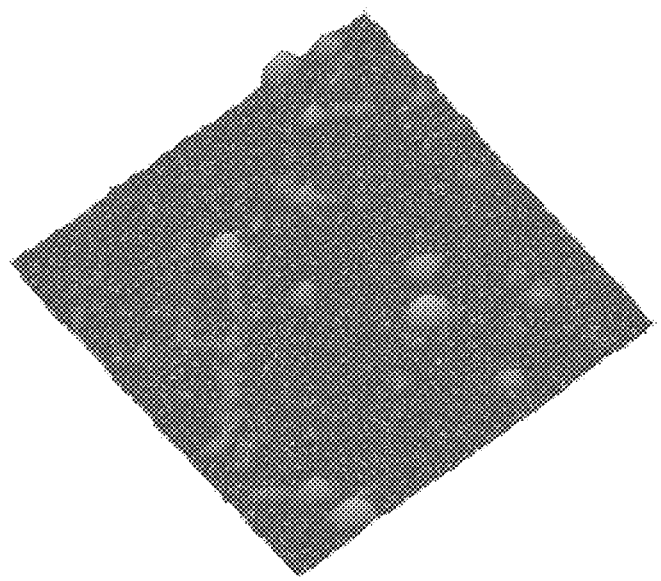
FIG. 8D.1
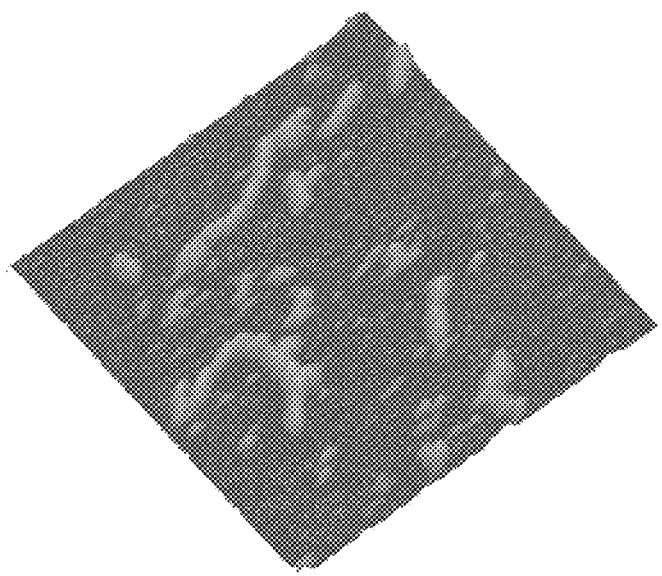
FIG. 8D.2

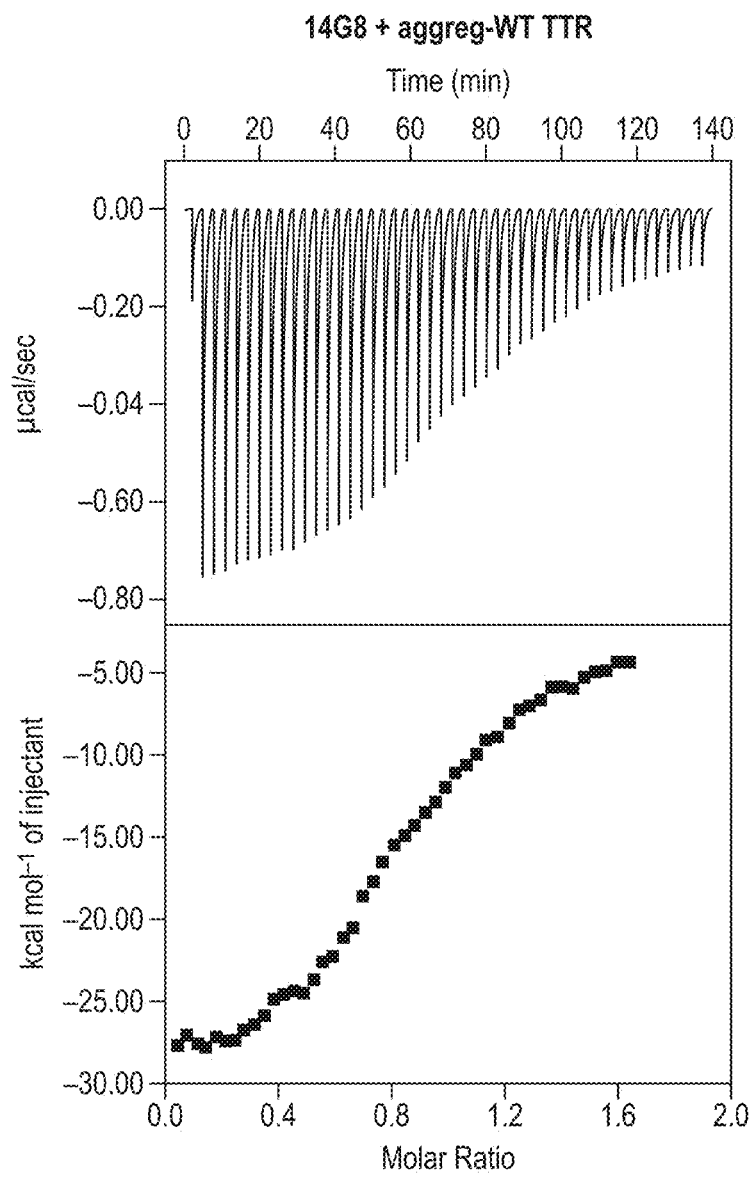
FIG. 9A.1

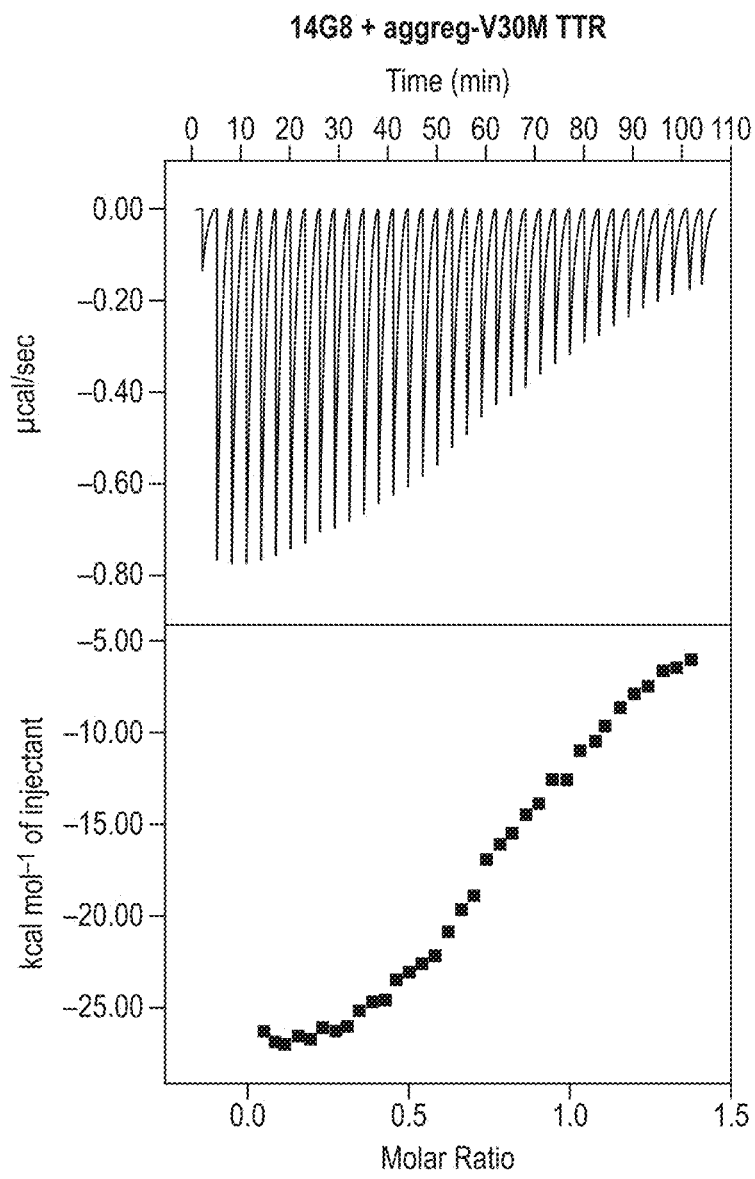
FIG. 9A.2

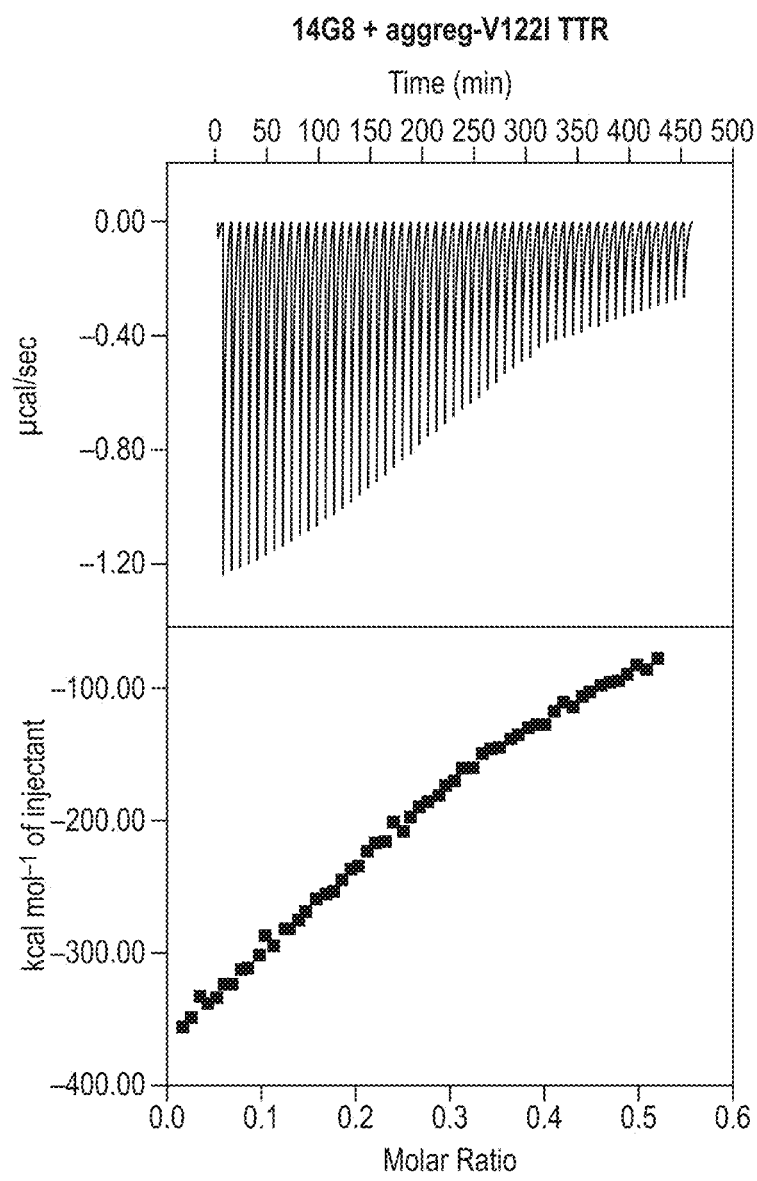
FIG. 9A.3

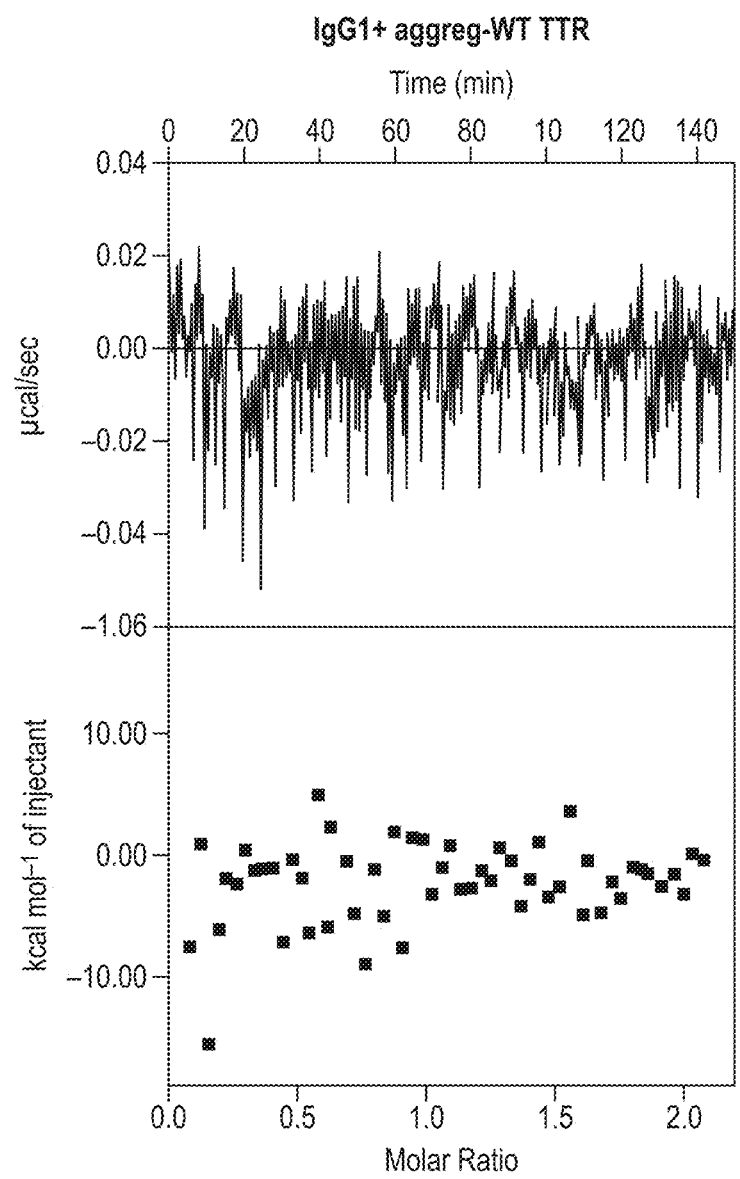
FIG. 9A.4

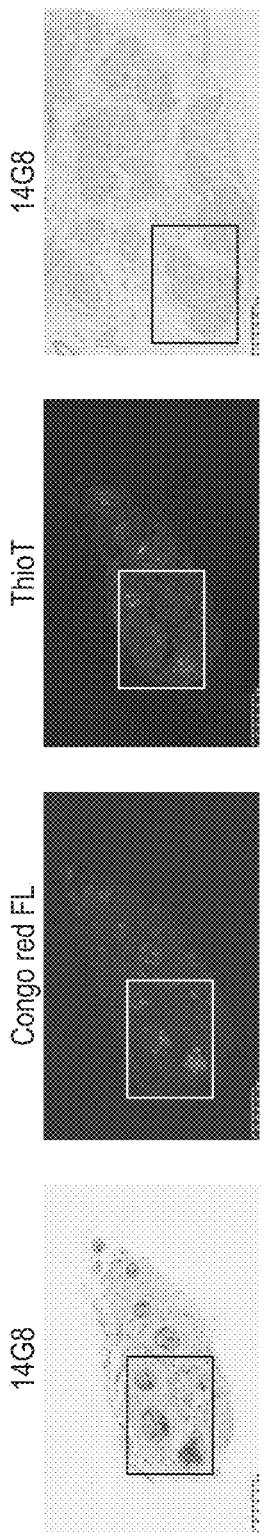
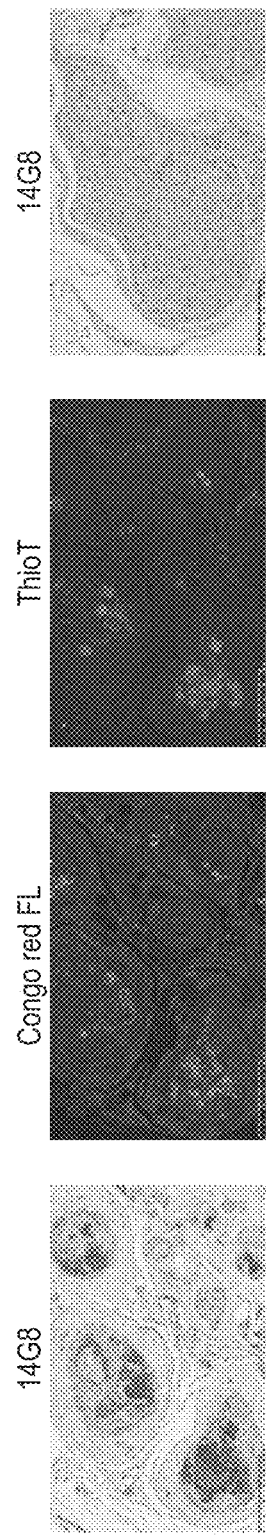
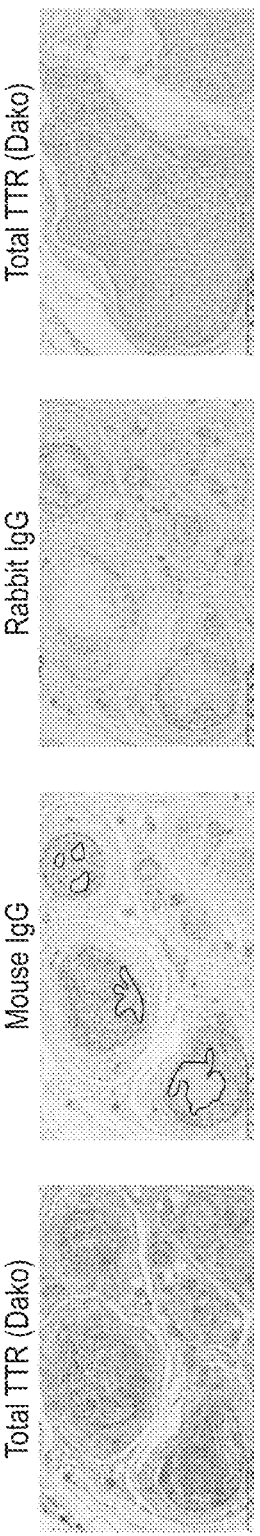
FIG. 10A.1  FIG. 10B.1  FIG. 10C.1  FIG. 10G.1
FIG. 10A.2  FIG. 10B.2  FIG. 10C.2  FIG. 10G.2
FIG. 10D   FIG. 10E   FIG. 10F   FIG. 10G.3

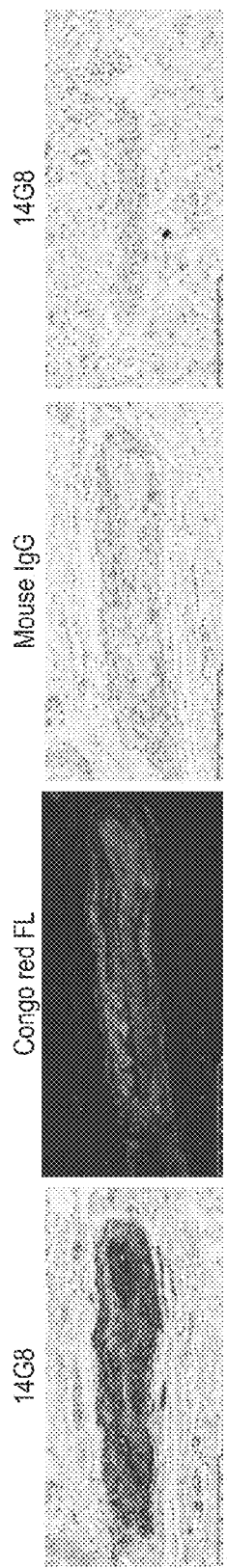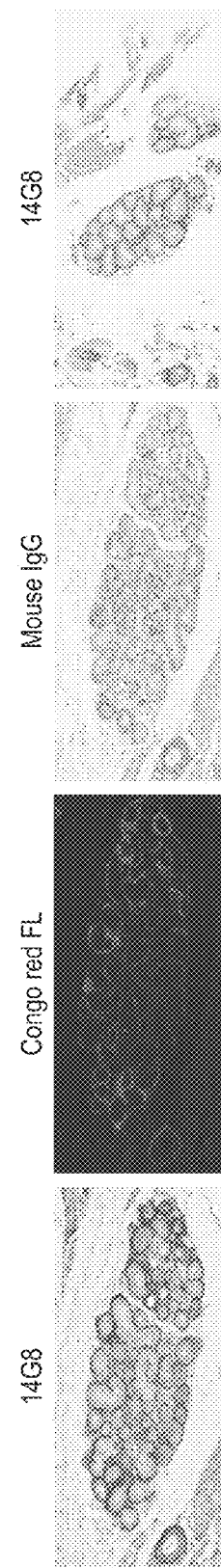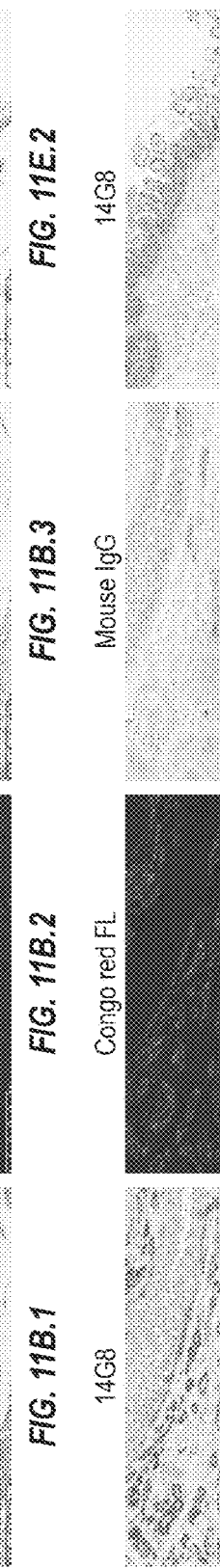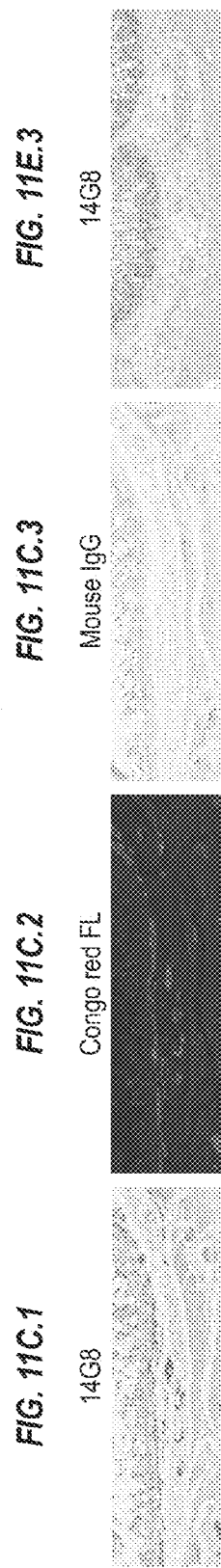
FIG. 11A.1 FIG. 11A.2 FIG. 11A.3 FIG. 11E.1
FIG. 11B.1 FIG. 11B.2 FIG. 11B.3 FIG. 11E.2
FIG. 11C.1 FIG. 11C.2 FIG. 11C.3 FIG. 11E.3
FIG. 11D.1 FIG. 11D.2 FIG. 11D.3 FIG. 11E.4

Figure 12A

Humanized 6C1 Vh Regions

| Chothia residue # | Kabat residue # | Linear residue # | FR or CDR | Murine 6C1 VH (SEQ ID NO:1) | Hu VH Acceptor Fr Acc# ADX65650 (SEQ ID NO:3) | 6C1 VHv1 (SEQ ID NO:4) | 6C1 VHv1b (SEQ ID NO:5) | 6C1 VHv2 (SEQ ID NO:6) | 6C1 VHv2b (SEQ ID NO:7) | 6C1 VHv3 (SEQ ID NO:8) | 6C1 VHv3b (SEQ ID NO:9) |
|---|---|---|---|---|---|---|---|---|---|---|---|
| 1 | 1 | 1 | Fr1 | E | E | E | E | E | E | E | E |
| 2 | 2 | 2 | Fr1 | V | V | V | V | V | V | V | V |
| 3 | 3 | 3 | Fr1 | Q | Q | Q | Q | Q | Q | Q | Q |
| 4 | 4 | 4 | Fr1 | L | L | L | L | L | L | L | L |
| 5 | 5 | 5 | Fr1 | V | V | V | V | V | V | V | V |
| 6 | 6 | 6 | Fr1 | E | E | E | E | E | E | E | E |
| 7 | 7 | 7 | Fr1 | S | S | S | S | S | S | S | S |
| 8 | 8 | 8 | Fr1 | G | G | G | G | G | G | G | G |
| 9 | 9 | 9 | Fr1 | G | G | G | G | G | G | G | G |
| 10 | 10 | 10 | Fr1 | G | G | G | G | G | G | G | G |
| 11 | 11 | 11 | Fr1 | L | L | L | L | L | L | L | L |
| 12 | 12 | 12 | Fr1 | V | V | V | V | V | V | V | V |
| 13 | 13 | 13 | Fr1 | Q | Q | Q | Q | Q | Q | Q | Q |
| 14 | 14 | 14 | Fr1 | P | P | P | P | P | P | P | P |
| 15 | 15 | 15 | Fr1 | G | G | G | G | G | G | G | G |
| 16 | 16 | 16 | Fr1 | G | G | G | G | G | G | G | G |
| 17 | 17 | 17 | Fr1 | S | S | S | S | S | S | S | S |
| 18 | 18 | 18 | Fr1 | L | L | L | L | L | L | L | L |
| 19 | 19 | 19 | Fr1 | K | R | R | R | R | R | K | K |
| 20 | 20 | 20 | Fr1 | L | L | L | L | L | L | L | L |
| 21 | 21 | 21 | Fr1 | S | S | S | S | S | S | S | S |
| 22 | 22 | 22 | Fr1 | C | C | C | C | C | C | C | C |
| 23 | 23 | 23 | Fr1 | A | A | A | A | A | A | A | A |
| 24 | 24 | 24 | Fr1 | A | A | A | A | A | A | A | A |
| 25 | 25 | 25 | Fr1 | S | S | S | S | S | S | S | S |
| 26 | 26 | 26 | CDR-H1 | G | G | G | G | G | G | G | G |
| 27 | 27 | 27 | CDR-H1 | F | F | F | F | F | F | F | F |
| 28 | 28 | 28 | CDR-H1 | T | T | T | T | T | T | T | T |
| 29 | 29 | 29 | CDR-H1 | F | F | F | F | F | F | F | F |
| 30 | 30 | 30 | CDR-H1 | S | S | S | S | S | S | S | S |
| 31 | 31 | 31 | CDR-H1 | N | S | N | N | N | N | N | N |
| 32 | 32 | 32 | CDR-H1 | Y | Y | Y | Y | Y | Y | Y | Y |
| 33 | 33 | 33 | CDR-H1 | Y | E | Y | Y | Y | Y | Y | Y |

Figure 12B

Humanized 6C1 Vh Regions

| | | | | | | | | | | | |
|---|---|---|---|---|---|---|---|---|---|---|---|
| 34 | 34 | 34 | CDR-H1 | M | M | M | M | M | M | M | M |
| 35 | 35 | 35 | CDR-H1 | S | N | S | S | S | S | S | S |
| 36 | 36 | 36 | Fr2 | W | W | W | W | W | W | W | W |
| 37 | 37 | 37 | Fr2 | V | V | V | V | V | V | V | V |
| 38 | 38 | 38 | Fr2 | R | R | R | R | R | R | R | R |
| 39 | 39 | 39 | Fr2 | Q | Q | Q | Q | Q | Q | Q | Q |
| 40 | 40 | 40 | Fr2 | T | A | A | A | A | A | A | A |
| 41 | 41 | 41 | Fr2 | P | P | P | P | P | P | P | P |
| 42 | 42 | 42 | Fr2 | E | G | G | G | G | G | G | G |
| 43 | 43 | 43 | Fr2 | K | K | K | K | K | K | K | K |
| 44 | 44 | 44 | Fr2 | R | G | G | G | G | G | R | R |
| 45 | 45 | 45 | Fr2 | L | L | L | L | L | L | L | L |
| 46 | 46 | 46 | Fr2 | E | E | E | E | E | E | E | E |
| 47 | 47 | 47 | Fr2 | W | W | W | W | W | W | W | W |
| 48 | 48 | 48 | Fr2 | V | V | V | V | V | V | V | V |
| 49 | 49 | 49 | Fr2 | A | S | S | A | S | A | S | A |
| 50 | 50 | 50 | CDR-H2 | Y | Y | Y | Y | Y | Y | Y | Y |
| 51 | 51 | 51 | CDR-H2 | I | I | I | I | I | I | I | I |
| 52 | 52 | 52 | CDR-H2 | S | S | S | S | S | S | S | S |
| 52A | 52A | 53 | CDR-H2 | I | S | I | I | I | I | I | I |
| 53 | 53 | 54 | CDR-H2 | D | S | D | D | D | D | D | D |
| 54 | 54 | 55 | CDR-H2 | G | G | G | G | G | G | G | G |
| 55 | 55 | 56 | CDR-H2 | N | S | N | N | N | N | N | N |
| 56 | 56 | 57 | CDR-H2 | N | T | N | N | N | N | N | N |
| 57 | 57 | 58 | CDR-H2 | I | I | I | I | I | I | I | I |
| 58 | 58 | 59 | CDR-H2 | Y | Y | Y | Y | Y | Y | Y | Y |
| 59 | 59 | 60 | CDR-H2 | H | Y | H | H | H | H | H | H |
| 60 | 60 | 61 | CDR-H2 | P | A | P | P | P | P | P | P |
| 61 | 61 | 62 | CDR-H2 | D | D | D | D | D | D | D | D |
| 62 | 62 | 63 | CDR-H2 | S | S | S | S | S | S | S | S |
| 63 | 63 | 64 | CDR-H2 | V | V | V | V | V | V | V | V |
| 64 | 64 | 65 | CDR-H2 | K | K | K | K | K | K | K | K |

Figure 12C

Humanized 6C1 Vh Regions

| | | | | | | | | | | | |
|---|---|---|---|---|---|---|---|---|---|---|---|
| 65 | 65 | 66 | CDR-H2 | G | G | G | G | G | G | G | G |
| 66 | 66 | 67 | Fr3 | R | R | R | R | R | R | R | R |
| 67 | 67 | 68 | Fr3 | F | F | F | F | F | F | F | F |
| 68 | 68 | 69 | Fr3 | T | T | T | T | T | T | T | T |
| 69 | 69 | 70 | Fr3 | I | I | I | I | I | I | I | I |
| 70 | 70 | 71 | Fr3 | S | S | S | S | S | S | S | S |
| 71 | 71 | 72 | Fr3 | R | R | R | R | R | R | R | R |
| 72 | 72 | 73 | Fr3 | D | D | D | D | D | D | D | D |
| 73 | 73 | 74 | Fr3 | N | N | N | N | N | N | N | N |
| 74 | 74 | 75 | Fr3 | A | A | A | A | A | A | A | A |
| 75 | 75 | 76 | Fr3 | K | K | K | K | K | K | K | K |
| 76 | 76 | 77 | Fr3 | N | N | N | N | S | S | N | N |
| 77 | 77 | 78 | Fr3 | T | S | T | T | T | T | T | T |
| 78 | 78 | 79 | Fr3 | L | L | L | L | L | L | L | L |
| 79 | 79 | 80 | Fr3 | Y | Y | Y | Y | Y | Y | Y | Y |
| 80 | 80 | 81 | Fr3 | L | L | L | L | L | L | L | L |
| 81 | 81 | 82 | Fr3 | Q | Q | Q | Q | Q | Q | Q | Q |
| 82 | 82 | 83 | Fr3 | M | M | M | M | M | M | M | M |
| 82A | 82A | 84 | Fr3 | S | N | N | N | S | S | N | N |
| 82B | 82B | 85 | Fr3 | S | S | S | S | S | S | S | S |
| 82C | 82C | 86 | Fr3 | L | L | L | L | L | L | L | L |
| 83 | 83 | 87 | Fr3 | K | R | R | R | R | R | K | K |
| 84 | 84 | 88 | Fr3 | S | A | A | A | A | A | A | A |
| 85 | 85 | 89 | Fr3 | E | E | E | E | E | E | E | E |
| 86 | 86 | 90 | Fr3 | D | D | D | D | D | D | D | D |
| 87 | 87 | 91 | Fr3 | T | T | T | T | T | T | T | T |
| 88 | 88 | 92 | Fr3 | A | A | A | A | A | A | A | A |
| 89 | 89 | 93 | Fr3 | M | V | V | V | V | V | M | M |
| 90 | 90 | 94 | Fr3 | Y | Y | Y | Y | Y | Y | Y | Y |
| 91 | 91 | 95 | Fr3 | Y | Y | Y | Y | Y | Y | Y | Y |
| 92 | 92 | 96 | Fr3 | C | C | C | C | C | C | C | C |
| 93 | 93 | 97 | Fr3 | A | A | A | A | A | A | A | A |
| 94 | 94 | 98 | Fr3 | R | R | R | R | R | R | R | R |
| 95 | 95 | 99 | CDR-H3 | D | D | D | D | D | D | D | D |
| 96 | 96 | 100 | CDR-H3 | S | L | S | S | S | S | S | S |
| 97 | 97 | 101 | CDR-H3 | D | S | D | D | D | D | D | D |
| 98 | 98 | 102 | CDR-H3 | Y | G | Y | Y | Y | Y | Y | Y |
| 99 | 99 | 103 | CDR-H3 | G | S | G | G | G | G | G | G |
| 100 | 100 | 104 | CDR-H3 | Y | Y | Y | Y | Y | Y | Y | Y |
| 100G | 100G | 105 | CDR-H3 | F | Y | F | F | F | F | F | F |

Figure 12D

Humanized 6C1 Vh Regions

| | | | | | | | | | | | |
|---|---|---|---|---|---|---|---|---|---|---|---|
| 101 | 101 | 106 | CDR-H3 | D | G | D | D | D | D | D | D |
| 102 | 102 | 107 | CDR-H3 | V | Y | V | V | V | V | V | V |
| 103 | 103 | 108 | Fr4 | W | W | W | W | W | W | W | W |
| 104 | 104 | 109 | Fr4 | G | G | G | G | G | G | G | G |
| 105 | 105 | 110 | Fr4 | T | Q | Q | Q | Q | Q | Q | Q |
| 106 | 106 | 111 | Fr4 | G | G | G | G | G | G | G | G |
| 107 | 107 | 112 | Fr4 | T | T | T | T | T | T | T | T |
| 108 | 108 | 113 | Fr4 | T | L | L | L | L | L | L | L |
| 109 | 109 | 114 | Fr4 | V | V | V | V | V | V | V | V |
| 110 | 110 | 115 | Fr4 | T | T | T | T | T | T | T | T |
| 111 | 111 | 116 | Fr4 | V | V | V | V | V | V | V | V |
| 112 | 112 | 117 | Fr4 | S | S | S | S | S | S | S | S |
| 113 | 113 | 118 | Fr4 | S | S | S | S | S | S | S | S |

Figure 13A

Humanized 6C1 Vk Regions

| Chothia residue # | Kabat residue # | Linear residue # | FR or CDR | Murine 6C1 VL (SEQ ID NO:13) | Hu VL Acceptor Fr Acc#ABI74084 (SEQ ID NO:15) | 6C1 VLv1 (SEQ ID NO:16) | 6C1 VLv2 (SEQ ID NO:17) |
|---|---|---|---|---|---|---|---|
| 1 | 1 | 1 | Fr1 | D | D | D | D |
| 2 | 2 | 2 | Fr1 | V | I | V | I |
| 3 | 3 | 3 | Fr1 | L | V | V | V |
| 4 | 4 | 4 | Fr1 | M | M | M | M |
| 5 | 5 | 5 | Fr1 | T | T | T | T |
| 6 | 6 | 6 | Fr1 | Q | Q | Q | Q |
| 7 | 7 | 7 | Fr1 | T | T | T | T |
| 8 | 8 | 8 | Fr1 | P | P | P | P |
| 9 | 9 | 9 | Fr1 | L | L | L | L |
| 10 | 10 | 10 | Fr1 | S | S | S | S |
| 11 | 11 | 11 | Fr1 | L | L | L | L |
| 12 | 12 | 12 | Fr1 | P | P | P | P |
| 13 | 13 | 13 | Fr1 | V | V | V | V |
| 14 | 14 | 14 | Fr1 | S | T | T | T |
| 15 | 15 | 15 | Fr1 | L | P | P | P |
| 16 | 16 | 16 | Fr1 | G | G | G | G |
| 17 | 17 | 17 | Fr1 | D | E | E | E |
| 18 | 18 | 18 | Fr1 | Q | P | P | P |
| 19 | 19 | 19 | Fr1 | A | A | A | A |
| 20 | 20 | 20 | Fr1 | S | S | S | S |
| 21 | 21 | 21 | Fr1 | I | I | I | I |
| 22 | 22 | 22 | Fr1 | S | S | S | S |
| 23 | 23 | 23 | Fr1 | C | C | C | C |
| 24 | 24 | 24 | CDR-L1 | R | R | R | R |
| 25 | 25 | 25 | CDR-L1 | S | S | S | S |
| 26 | 26 | 26 | CDR-L1 | S | S | S | S |
| 27 | 27 | 27 | CDR-L1 | Q | Q | Q | Q |
| 27A | 27A | 28 | CDR-L1 | S | S | S | S |
| 27B | 27B | 29 | CDR-L1 | I | L | I | I |
| 27C | 27C | 30 | CDR-L1 | V | L | V | V |
| 27D | 27D | 31 | CDR-L1 | H | H | H | H |
| 27E | 27E | 32 | CDR-L1 | S | S | S | S |

Figure 13B

Humanized 6C1 Vk Regions

| | | | | | | | |
|---|---|---|---|---|---|---|---|
| 28 | 28 | 33 | CDR-L1 | N | N | N | N |
| 29 | 29 | 34 | CDR-L1 | G | G | G | G |
| 30 | 30 | 35 | CDR-L1 | N | Y | N | N |
| 31 | 31 | 36 | CDR-L1 | T | N | T | T |
| 32 | 32 | 37 | CDR-L1 | Y | Y | Y | Y |
| 33 | 33 | 38 | CDR-L1 | L | L | L | L |
| 34 | 34 | 39 | CDR-L1 | E | D | E | E |
| 35 | 35 | 40 | Fr2 | W | W | W | W |
| 36 | 36 | 41 | Fr2 | Y | Y | Y | Y |
| 37 | 37 | 42 | Fr2 | L | L | L | L |
| 38 | 38 | 43 | Fr2 | Q | Q | Q | Q |
| 39 | 39 | 44 | Fr2 | K | K | K | K |
| 40 | 40 | 45 | Fr2 | R | P | P | P |
| 41 | 41 | 46 | Fr2 | G | G | G | G |
| 42 | 42 | 47 | Fr2 | Q | Q | Q | Q |
| 43 | 43 | 48 | Fr2 | S | S | S | S |
| 44 | 44 | 49 | Fr2 | P | P | P | P |
| 45 | 45 | 50 | Fr2 | K | Q | K | K |
| 46 | 46 | 51 | Fr2 | L | L | L | L |
| 47 | 47 | 52 | Fr2 | L | L | L | L |
| 48 | 48 | 53 | Fr2 | I | I | I | I |
| 49 | 49 | 54 | Fr2 | Y | Y | Y | Y |
| 50 | 50 | 55 | CDR-L2 | K | L | K | K |
| 51 | 51 | 56 | CDR-L2 | V | G | V | V |
| 52 | 52 | 57 | CDR-L2 | S | S | S | S |
| 53 | 53 | 58 | CDR-L2 | K | N | K | K |
| 54 | 54 | 59 | CDR-L2 | R | R | R | R |
| 55 | 55 | 60 | CDR-L2 | F | A | F | F |
| 56 | 56 | 61 | CDR-L2 | S | S | S | S |
| 57 | 57 | 62 | Fr3 | G | G | G | G |
| 58 | 58 | 63 | Fr3 | V | V | V | V |
| 59 | 59 | 64 | Fr3 | P | P | P | P |
| 60 | 60 | 65 | Fr3 | D | D | D | D |
| 61 | 61 | 66 | Fr3 | R | R | R | R |
| 62 | 62 | 67 | Fr3 | F | F | F | F |

Figure 13C

Humanized 6C1 Vk Regions

| | | | | | | | |
|---|---|---|---|---|---|---|---|
| 63 | 63 | 68 | Fr3 | S | S | S | S |
| 64 | 64 | 69 | Fr3 | G | G | G | G |
| 65 | 65 | 70 | Fr3 | S | S | S | S |
| 66 | 66 | 71 | Fr3 | G | G | G | G |
| 67 | 67 | 72 | Fr3 | S | S | S | S |
| 68 | 68 | 73 | Fr3 | G | G | G | G |
| 69 | 69 | 74 | Fr3 | T | T | T | T |
| 70 | 70 | 75 | Fr3 | D | D | D | D |
| 71 | 71 | 76 | Fr3 | F | F | F | F |
| 72 | 72 | 77 | Fr3 | I | T | T | T |
| 73 | 73 | 78 | Fr3 | L | L | L | L |
| 74 | 74 | 79 | Fr3 | K | K | K | K |
| 75 | 75 | 80 | Fr3 | I | I | I | I |
| 76 | 76 | 81 | Fr3 | S | S | S | S |
| 77 | 77 | 82 | Fr3 | R | R | R | R |
| 78 | 78 | 83 | Fr3 | V | V | V | V |
| 79 | 79 | 84 | Fr3 | E | E | E | E |
| 80 | 80 | 85 | Fr3 | A | A | A | A |
| 81 | 81 | 86 | Fr3 | E | E | E | E |
| 82 | 82 | 87 | Fr3 | D | D | D | D |
| 83 | 83 | 88 | Fr3 | L | V | V | V |
| 84 | 84 | 89 | Fr3 | G | G | G | G |
| 85 | 85 | 90 | Fr3 | V | V | V | V |
| 86 | 86 | 91 | Fr3 | Y | Y | Y | Y |
| 87 | 87 | 92 | Fr3 | Y | Y | Y | Y |
| 88 | 88 | 93 | Fr3 | C | C | C | C |
| 89 | 89 | 94 | CDR-L3 | F | M | F | F |
| 90 | 90 | 95 | CDR-L3 | Q | Q | Q | Q |
| 91 | 91 | 96 | CDR-L3 | G | G | G | G |
| 92 | 92 | 97 | CDR-L3 | S | L | S | S |
| 93 | 93 | 98 | CDR-L3 | H | Q | H | H |
| 94 | 94 | 99 | CDR-L3 | V | T | V | V |
| 95 | 95 | 100 | CDR-L3 | P | P | P | P |
| 96 | 96 | 101 | CDR-L3 | L | L | L | L |
| 97 | 97 | 102 | CDR-L3 | T | T | T | T |
| 98 | 98 | 103 | Fr4 | F | F | F | F |
| 99 | 99 | 104 | Fr4 | G | G | G | G |
| 100 | 100 | 105 | Fr4 | G | G | G | G |
| 101 | 101 | 106 | Fr4 | G | G | G | G |

Figure 13D

Humanized 6C1 Vk Regions

| 102 | 102 | 107 | Fr4 | T | T | T | T |
|-----|-----|-----|-----|---|---|---|---|
| 103 | 103 | 108 | Fr4 | K | K | K | K |
| 104 | 104 | 109 | Fr4 | L | V | V | V |
| 105 | 105 | 110 | Fr4 | E | E | E | E |
| 106 | 106 | 111 | Fr4 | L | I | I | I |
| 107 | 107 | 112 | Fr4 | K | K | K | K |

SEQUENCE LISTING

```
<160> NUMBER OF SEQ ID NOS: 63

<210> SEQ ID NO 1
<211> LENGTH: 118
<212> TYPE: PRT
<213> ORGANISM: Artificial Sequence
<220> FEATURE:
<223> OTHER INFORMATION: Synthesized

<400> SEQUENCE: 1

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Trp Val
        35                  40                  45

Ala Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95
```

Ala Arg Asp Ser Asp Tyr Gly Tyr Phe Asp Val Trp Gly Thr Gly Thr
            100                 105                 110

Thr Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Synthesized

<400> SEQUENCE: 2

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Arg Asp Tyr
            20                  25                  30

Tyr Met Tyr Trp Val Arg Gln Thr Pro Glu Lys Arg Leu Glu Trp Val
        35                  40                  45

Ala Phe Ile Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Arg Gly Tyr Val Trp Phe Ala Tyr Trp Gly Gln Gly Thr
            100                 105                 110

Thr Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Synthesized

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Ser Tyr Tyr Gly Tyr Trp Gly Gln Gly Thr
            100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Synthesized

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser
        115

<210> SEQ ID NO 5
<211> LENGTH: 118
<212> TYPE: PRT
<213> ORGANISM: Artificial Sequence
<220> FEATURE:
<223> OTHER INFORMATION: Synthesized

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Synthesized

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
            35                  40                  45

Ser Tyr Ile Ser Ile Asp Gly Asn Asn Ile Tyr His Pro Asp Ser Val
 50                  55                  60

Lys Gly Arg Phe Thr Ile Ser Arg Asp Asn Ala Lys Ser Thr Leu Tyr
 65                  70                  75                  80

Leu Gln Met Ser Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
                100                 105                 110

Leu Val Thr Val Ser Ser
            115

<210> SEQ ID NO 7
<211> LENGTH: 118
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
                20                  25                  30

Tyr Met Ser Trp Val Arg Gln Ala Pro Gly Lys Gly Leu Glu Trp Val
            35                  40                  45

Ala Tyr Ile Ser Ile Asp Gly Asn Asn Ile Tyr His Pro Asp Ser Val
 50                  55                  60

Lys Gly Arg Phe Thr Ile Ser Arg Asp Asn Ala Lys Ser Thr Leu Tyr
 65                  70                  75                  80

Leu Gln Met Ser Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
                100                 105                 110

Leu Val Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Asn Tyr
                20                  25                  30

Tyr Met Ser Trp Val Arg Gln Ala Pro Gly Lys Arg Leu Glu Trp Val
            35                  40                  45

Ser Tyr Ile Ser Ile Asp Gly Asn Asn Ile Tyr His Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Met Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser
        115

<210> SEQ ID NO 9
<211> LENGTH: 118
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Ala Pro Gly Lys Arg Leu Glu Trp Val
        35                  40                  45

Ala Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser
        115

<210> SEQ ID NO 10
<211> LENGTH: 5
<212> TYPE: PRT
<213> ORGANISM: Artificial Sequence
<220> FEATURE:
<223> OTHER INFORMATION: Synthesized

<400> SEQUENCE: 10

Asn Tyr Tyr Met Ser
1               5

<210> SEQ ID NO 11
<211> LENGTH: 17
<212> TYPE: PRT
<213> ORGANISM: Artificial Sequence
<220> FEATURE:
<223> OTHER INFORMATION: Synthesized

<400> SEQUENCE: 11

Tyr Ile Ser Ile Asp Gly Asn Asn Ile Tyr His Pro Asp Ser Val Lys
1               5                   10                  15

Gly

<210> SEQ ID NO 12
<211> LENGTH: 9
<212> TYPE: PRT
<213> ORGANISM: Artificial Sequence
<220> FEATURE:
<223> OTHER INFORMATION: Synthesized

<400> SEQUENCE: 12

Asp Ser Asp Tyr Gly Tyr Phe Asp Val
1               5

<210> SEQ ID NO 13
<211> LENGTH: 112
<212> TYPE: PRT
<213> ORGANISM: Artificial Sequence
<220> FEATURE:
<223> OTHER INFORMATION: Synthesized

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Arg Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Leu Glu Leu Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Synthesized

<400> SEQUENCE: 14

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: Synthesized

<400> SEQUENCE: 15

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser

```
                        20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Val Glu Ile Lys
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Synthesized

<400> SEQUENCE: 16

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: Synthesized

<400> SEQUENCE: 17

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110
```

<210> SEQ ID NO 18
<211> LENGTH: 16
<212> TYPE: PRT
<213> ORGANISM: Artificial Sequence
<220> FEATURE:
<223> OTHER INFORMATION: Synthesized

<400> SEQUENCE: 18

Arg Ser Ser Gln Ser Ile Val His Ser Asn Gly Asn Thr Tyr Leu Glu
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Synthesized

<400> SEQUENCE: 19

Lys Val Ser Lys Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized

<400> SEQUENCE: 20

Phe Gln Gly Ser His Val Pro Leu Thr
1               5

<210> SEQ ID NO 21
<211> LENGTH: 411
<212> TYPE: DNA
<213> ORGANISM: Artificial Sequence
<220> FEATURE:
<223> OTHER INFORMATION: Synthesized

<400> SEQUENCE: 21

```
atgaactttg ggttcagctt gattttcctt gtccttgttt taaaaggtgt gaagtgtgaa      60
gtgcagctgg tggagtctgg gggaggctta gtgcagcctg agggtccct gaaactctcc      120 tgtgcagcct ctggattcac ttttagtaac tattacatgt cttgggttcg ccagactcca     180
gagaagaggc tggagtgggt cgcatacatt agtattgatg gtaataatat ctaccatcca     240
gacagtgtga agggtcgatt caccatctcc agagacaatg ccaagaacac cctgtacctg     300
caaatgagca gtctgaagtc tgaggacaca gccatgtatt actgtgcaag agacagtgac     360
tacggctact cgatgtctg ggcacaggg accacggtca ccgtctcctc a                411
```

<210> SEQ ID NO 22
<211> LENGTH: 137
<212> TYPE: PRT
<213> ORGANISM: Artificial Sequence
<220> FEATURE:
<223> OTHER INFORMATION: Synthesized

<400> SEQUENCE: 22

Met Asn Phe Gly Phe Ser Leu Ile Phe Leu Val Leu Val Leu Lys Gly
1               5                   10                  15

Val Lys Cys Glu Val Gln Leu Val Glu Ser Gly Gly Gly Leu Val Gln
                20                  25                  30

```
Pro Gly Gly Ser Leu Lys Leu Ser Cys Ala Ala Ser Gly Phe Thr Phe
            35                  40                  45

Ser Asn Tyr Tyr Met Ser Trp Val Arg Gln Thr Pro Glu Lys Arg Leu
 50                  55                  60

Glu Trp Val Ala Tyr Ile Ser Ile Asp Gly Asn Asn Ile Tyr His Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ala Arg Asp Ser Asp Tyr Gly Tyr Phe Asp Val Trp Gly
            115                 120                 125

Thr Gly Thr Thr Val Thr Val Ser Ser
        130                 135

<210> SEQ ID NO 23
<211> LENGTH: 393
<212> TYPE: DNA
<213> ORGANISM: Artificial Sequence
<220> FEATURE:
<223> OTHER INFORMATION: Synthesized

<400> SEQUENCE: 23
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac gaggccagtc tccaaagctc ctgatctaca aagtttccaa acgatttcct     240 gggqtcccag acaggttcag tggcagtgga tcagggacag atttcatact caagatcagc     300
agagtggagg ctgaggatct gggagtttat tactgctttc aaggttcaca tgttccgctc     360
acgttcggtg gtgggaccaa gctggagctg aaa                                  393

<210> SEQ ID NO 24
<211> LENGTH: 131
<212> TYPE: PRT
<213> ORGANISM: Artificial Sequence
<220> FEATURE:
<223> OTHER INFORMATION: Synthesized

<400> SEQUENCE: 24

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
                 20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Arg
 50                  55                  60

Gly Gln Ser Pro Lys Leu Leu Ile Tyr Lys Val Ser Lys Arg Phe Ser
 65                  70                  75                  80

Gly Val Pro Asp Arg Phe Ser Gly Ser Gly Ser Gly Thr Asp Phe Ile
                 85                  90                  95

Leu Lys Ile Ser Arg Val Glu Ala Glu Asp Leu Gly Val Tyr Tyr Cys
            100                 105                 110

Phe Gln Gly Ser His Val Pro Leu Thr Phe Gly Gly Gly Thr Lys Leu
            115                 120                 125
```

```
Glu Leu Lys
    130

<210> SEQ ID NO 25
<211> LENGTH: 330
<212> TYPE: PRT
<213> ORGANISM: Artificial Sequence
<220> FEATURE:
<223> OTHER INFORMATION: Synthesized

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 330
```

<212> TYPE: PRT
<213> ORGANISM: Artificial Sequence
<220> FEATURE:
<223> OTHER INFORMATION: Synthesized

<400> SEQUENCE: 26

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 27
<211> LENGTH: 330
<212> TYPE: PRT
<213> ORGANISM: Artificial Sequence
<220> FEATURE:
<223> OTHER INFORMATION: Synthesized

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 107
<212> TYPE: PRT
<213> ORGANISM: Artificial Sequence
<220> FEATURE:
<223> OTHER INFORMATION: Synthesized

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Synthesized

<400> SEQUENCE: 29

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 30
<211> LENGTH: 448
<212> TYPE: PRT
<213> ORGANISM: Artificial Sequence
<220> FEATURE:
<223> OTHER INFORMATION: Synthesized

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser Ala Ser Thr Lys Gly Pro Ser Val Phe Pro

```
                115                 120                 125
Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 31
<211> LENGTH: 448
<212> TYPE: PRT
<213> ORGANISM: Artificial Sequence
<220> FEATURE:
<223> OTHER INFORMATION: Synthesized

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
```

```
                35                  40                  45
Ala Tyr Ile Ser Ile Asp Gly Asn Asn Ile Tyr His Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Asp Tyr Gly Tyr Phe Asp Val Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 32
```

<211> LENGTH: 448
<212> TYPE: PRT
<213> ORGANISM: Artificial Sequence
<220> FEATURE:
<223> OTHER INFORMATION: Synthesized

<400> SEQUENCE: 32

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Tyr |
|---|---|---|---|---|---|---|---|---|---|---|---|---|---|---|---|
| | | | 20 | | | | | 25 | | | | | 30 | | |

| Tyr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Tyr | Ile | Ser | Ile | Asp | Gly | Asn | Asn | Ile | Tyr | His | Pro | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ala | Lys | Ser | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Ser | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Ser | Asp | Tyr | Gly | Tyr | Phe | Asp | Val | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser | Ala | Ser | Thr | Lys | Gly | Pro | Ser | Val | Phe | Pro |
|---|---|---|---|---|---|---|---|---|---|---|---|---|---|---|---|
| | | 115 | | | | | 120 | | | | | 125 | | | |

| Leu | Ala | Pro | Ser | Ser | Lys | Ser | Thr | Ser | Gly | Gly | Thr | Ala | Ala | Leu | Gly |
|---|---|---|---|---|---|---|---|---|---|---|---|---|---|---|---|
| 130 | | | | | 135 | | | | | 140 | | | | | |

| Cys | Leu | Val | Lys | Asp | Tyr | Phe | Pro | Glu | Pro | Val | Thr | Val | Ser | Trp | Asn |
|---|---|---|---|---|---|---|---|---|---|---|---|---|---|---|---|
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
|---|---|---|---|---|---|---|---|---|---|---|---|---|---|---|---|
| | | | | 165 | | | | | 170 | | | | | 175 | |

| Ser | Ser | Gly | Leu | Tyr | Ser | Leu | Ser | Val | Val | Thr | Val | Pro | Ser | Ser |
|---|---|---|---|---|---|---|---|---|---|---|---|---|---|---|
| | | | 180 | | | | | 185 | | | | | 190 | |

| Ser | Leu | Gly | Thr | Gln | Thr | Tyr | Ile | Cys | Asn | Val | Asn | His | Lys | Pro | Ser |
|---|---|---|---|---|---|---|---|---|---|---|---|---|---|---|---|
| | | 195 | | | | | 200 | | | | | 205 | | | |

| Asn | Thr | Lys | Val | Asp | Lys | Arg | Val | Glu | Pro | Lys | Ser | Cys | Asp | Lys | Thr |
|---|---|---|---|---|---|---|---|---|---|---|---|---|---|---|---|
| | 210 | | | | | 215 | | | | | 220 | | | | |

| His | Thr | Cys | Pro | Pro | Cys | Pro | Ala | Pro | Glu | Leu | Leu | Gly | Gly | Pro | Ser |
|---|---|---|---|---|---|---|---|---|---|---|---|---|---|---|---|
| 225 | | | | | 230 | | | | | 235 | | | | | 240 |

| Val | Phe | Leu | Phe | Pro | Pro | Lys | Pro | Lys | Asp | Thr | Leu | Met | Ile | Ser | Arg |
|---|---|---|---|---|---|---|---|---|---|---|---|---|---|---|---|
| | | | | 245 | | | | | 250 | | | | | 255 | |

| Thr | Pro | Glu | Val | Thr | Cys | Val | Val | Val | Asp | Val | Ser | His | Glu | Asp | Pro |
|---|---|---|---|---|---|---|---|---|---|---|---|---|---|---|---|
| | | | 260 | | | | | 265 | | | | | 270 | | |

| Glu | Val | Lys | Phe | Asn | Trp | Tyr | Val | Asp | Gly | Val | Glu | Val | His | Asn | Ala |
|---|---|---|---|---|---|---|---|---|---|---|---|---|---|---|---|
| | | 275 | | | | | 280 | | | | | 285 | | | |

| Lys | Thr | Lys | Pro | Arg | Glu | Glu | Gln | Tyr | Asn | Ser | Thr | Tyr | Arg | Val | Val |
|---|---|---|---|---|---|---|---|---|---|---|---|---|---|---|---|
| | 290 | | | | | 295 | | | | | 300 | | | | |

| Ser | Val | Leu | Thr | Val | Leu | His | Gln | Asp | Trp | Leu | Asn | Gly | Lys | Glu | Tyr |
|---|---|---|---|---|---|---|---|---|---|---|---|---|---|---|---|
| 305 | | | | | 310 | | | | | 315 | | | | | 320 |

| Lys | Cys | Lys | Val | Ser | Asn | Lys | Ala | Leu | Pro | Ala | Pro | Ile | Glu | Lys | Thr |
|---|---|---|---|---|---|---|---|---|---|---|---|---|---|---|---|
| | | | | 325 | | | | | 330 | | | | | 335 | |

| Ile | Ser | Lys | Ala | Lys | Gly | Gln | Pro | Arg | Glu | Pro | Gln | Val | Tyr | Thr | Leu |
|---|---|---|---|---|---|---|---|---|---|---|---|---|---|---|---|
| | | | 340 | | | | | 345 | | | | | 350 | | |

| Pro | Pro | Ser | Arg | Glu | Glu | Met | Thr | Lys | Asn | Gln | Val | Ser | Leu | Thr | Cys |
|---|---|---|---|---|---|---|---|---|---|---|---|---|---|---|---|
| | | 355 | | | | | 360 | | | | | 365 | | | |

| Leu | Val | Lys | Gly | Phe | Tyr | Pro | Ser | Asp | Ile | Ala | Val | Glu | Trp | Glu | Ser |
|---|---|---|---|---|---|---|---|---|---|---|---|---|---|---|---|
| | 370 | | | | | 375 | | | | | 380 | | | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 33
<211> LENGTH: 448
<212> TYPE: PRT
<213> ORGANISM: Artificial Sequence
<220> FEATURE:
<223> OTHER INFORMATION: Synthesized

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 34
<211> LENGTH: 448
<212> TYPE: PRT
<213> ORGANISM: Artificial Sequence
<220> FEATURE:
<223> OTHER INFORMATION: Synthesized

<400> SEQUENCE: 34

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Ala Pro Gly Lys Arg Leu Glu Trp Val
        35                  40                  45

Ser Tyr Ile Ser Ile Asp Gly Asn Asn Ile Tyr His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Arg Asp Ser Asp Tyr Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 35
<211> LENGTH: 448
<212> TYPE: PRT
<213> ORGANISM: Artificial Sequence
<220> FEATURE:
<223> OTHER INFORMATION: Synthesized

<400> SEQUENCE: 35

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Ala Pro Gly Lys Arg Leu Glu Trp Val
            35                  40                  45

Ala Tyr Ile Ser Ile Asp Gly Asn Asn Ile Tyr His Pro Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Met Tyr Tyr Cys
            85                  90                  95

Ala Arg Asp Ser Asp Tyr Gly Tyr Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 36
<211> LENGTH: 219
<212> TYPE: PRT
<213> ORGANISM: Artificial Sequence
<220> FEATURE:
<223> OTHER INFORMATION: Synthesized

<400> SEQUENCE: 36

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Lys Arg Phe Ser Gly Val Pro
50                  55                  60
```

-continued

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 37
<211> LENGTH: 219
<212> TYPE: PRT
<213> ORGANISM: Artificial Sequence
<220> FEATURE:
<223> OTHER INFORMATION: Synthesized

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
    210                 215
```

<210> SEQ ID NO 38
<211> LENGTH: 147
<212> TYPE: PRT
<213> ORGANISM: Homo sapiens

<400> SEQUENCE: 38

```
Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
                115                 120                 125

Ala Leu Leu Ser Pro Tyr Ser Tyr Ser Thr Thr Ala Val Val Thr Asn
130                 135                 140

Pro Lys Glu
145
```

<210> SEQ ID NO 39
<211> LENGTH: 127
<212> TYPE: PRT
<213> ORGANISM: Homo sapiens

<400> SEQUENCE: 39

```
Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Gln Phe
50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
                100                 105                 110

Pro Tyr Ser Tyr Ser Thr Thr Ala Val Val Thr Asn Pro Lys Glu
                115                 120                 125
```

<210> SEQ ID NO 40
<211> LENGTH: 127
<212> TYPE: PRT
<213> ORGANISM: Homo sapiens

<400> SEQUENCE: 40

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Gln Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 41
<211> LENGTH: 138
<212> TYPE: PRT
<213> ORGANISM: Homo sapiens

<400> SEQUENCE: 41

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Ser Tyr Ser
        115                 120                 125

Thr Thr Ala Val Val Thr Asn Pro Lys Glu
    130                 135

<210> SEQ ID NO 42
<211> LENGTH: 9
<212> TYPE: PRT
<213> ORGANISM: Artificial Sequence
<220> FEATURE:
<223> OTHER INFORMATION: Synthesized

<400> SEQUENCE: 42

Glu His Ala Glu Val Val Phe Thr Ala
1               5

<210> SEQ ID NO 43
<211> LENGTH: 15
<212> TYPE: PRT

```
<213> ORGANISM: Artificial Sequence
<220> FEATURE:
<223> OTHER INFORMATION: Synthesized

<400> SEQUENCE: 43

Gly Gly Glu His Ala Glu Val Val Phe Thr Ala Gly Gly Lys Gly
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: Synthesized

<400> SEQUENCE: 44

Cys Gly Gly Glu His Ala Glu Val Val Phe Thr Ala
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthesized

<400> SEQUENCE: 45

Glu His Ala Glu Val Val Phe Thr Ala Cys Gly Gly
1               5                   10

<210> SEQ ID NO 46
<211> LENGTH: 990
<212> TYPE: DNA
<213> ORGANISM: Artificial Sequence
<220> FEATURE:
<223> OTHER INFORMATION: Synthesized

<400> SEQUENCE: 46
```

| | | | | | |
|---|---|---|---|---|---|
| gcctccacca | agggtccatc | ggtcttcccc | ctggcaccct | cctccaagag | cacctctggg        60 |
| ggcacagcgg | ccctgggctg | cctggtcaag | gactacttcc | ccgaaccggt | gacggtgtcg       120 |
| tggaactcag | gcgccctgac | cagcggcgtg | cacaccttcc | cggctgtcct | acagtcctca       180 |
| ggactctact | ccctcagcag | cgtggtgacc | gtgccctcca | gcagcttggg | cacccagacc       240 |
| tacatctgca | acgtgaatca | caagcccagc | aacaccaagg | tggacaagag | agttgagccc       300 |
| aaatcttgtg | acaaaactca | cacatgccca | ccgtgcccag | cacctgaact | cctggggggga      360 |
| ccgtcagtct | tcctcttccc | cccaaaaccc | aaggacaccc | tcatgatctc | ccggaccctc       420 |
| gaggtcacat | gcgtggtggt | ggacgtgagc | cacgaagacc | ctgaggtcaa | gttcaactgg       480 |
| tacgtggacg | gcgtggaggt | gcataatgcc | aagacaaagc | cgcgggagga | gcagtacaac       540 |
| agcacgtacc | gtgtggtcag | cgtcctcacc | gtcctgcacc | aggactggct | gaatggcaag       600 |
| gagtacaagt | gcaaggtctc | caacaaagcc | ctcccagccc | ccatcgagaa | aaccatctcc       660 |
| aaagccaaag | ggcagccccg | agaaccacag | gtgtacaccc | tgcccccatc | ccgggaggag       720 |
| atgaccaaga | accaggtcag | cctgacctgc | ctggtcaaag | gcttctatcc | cagcgacatc       780 |
| gccgtggagt | gggagagcaa | tgggcagccg | gagaacaact | acaagaccac | gcctcccgtg       840 |
| ctggactccg | acggctcctt | cttcctctat | agcaagctca | ccgtggacaa | gagcaggtgg       900 |
| cagcagggga | acgtcttctc | atgctccgtg | atgcatgagg | ctctgcacaa | ccactacacg       960 |
| cagaagagcc | tctccctgtc | cccgggtaaa |            |            |            990 |

<210> SEQ ID NO 47
<211> LENGTH: 321
<212> TYPE: DNA
<213> ORGANISM: Artificial Sequence
<220> FEATURE:
<223> OTHER INFORMATION: Synthesized

<400> SEQUENCE: 47

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321
```

<210> SEQ ID NO 48
<211> LENGTH: 318
<212> TYPE: DNA
<213> ORGANISM: Artificial Sequence
<220> FEATURE:
<223> OTHER INFORMATION: Synthesized

<400> SEQUENCE: 48

```
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318
```

<210> SEQ ID NO 49
<211> LENGTH: 19
<212> TYPE: PRT
<213> ORGANISM: Artificial Sequence
<220> FEATURE:
<223> OTHER INFORMATION: Synthesized

<400> SEQUENCE: 49

```
Met Asn Phe Gly Phe Ser Leu Ile Phe Leu Val Leu Val Leu Lys Gly
1               5                   10                  15

Val Lys Cys
```

<210> SEQ ID NO 50
<211> LENGTH: 57
<212> TYPE: DNA
<213> ORGANISM: Artificial Sequence
<220> FEATURE:
<223> OTHER INFORMATION: Synthesized

<400> SEQUENCE: 50

```
atgaactttg ggttcagctt gattttcctt gtccttgttt taaaaggtgt gaagtgt        57
```

<210> SEQ ID NO 51
<211> LENGTH: 19
<212> TYPE: PRT
<213> ORGANISM: Artificial Sequence
<220> FEATURE:
<223> OTHER INFORMATION: Synthesized

<400> SEQUENCE: 51

Met Lys Leu Pro Val Arg Leu Leu Val Leu Met Phe Trp Ile Pro Ala
1               5                   10                  15

Ser Ser Ser

<210> SEQ ID NO 52
<211> LENGTH: 57
<212> TYPE: DNA
<213> ORGANISM: Artificial Sequence
<220> FEATURE:
<223> OTHER INFORMATION: Synthesized

<400> SEQUENCE: 52

```
atgaagttgc ctgttaggct gttggtgctg atgttctgga ttcctgcttc cagcagt      57
```

<210> SEQ ID NO 53
<211> LENGTH: 336
<212> TYPE: DNA
<213> ORGANISM: Artificial Sequence
<220> FEATURE:
<223> OTHER INFORMATION: Synthesized

<400> SEQUENCE: 53

```
gatgttttga tgacccaaac tccactctcc ctgcctgtca gtcttggaga tcaagcctcc     60
atctcttgca gatctagtca gagcattgta catagtaatg aaacaccta tttagaatgg    120
tacctgcaga aacgaggcca gtctccaaag ctcctgatct acaaagtttc caaacgattt    180
tctggggtcc cagacaggtt cagtggcagt ggatcaggga cagatttcat actcaagatc    240
agcagagtgg aggctgagga tctggagtt tattactgct ttcaaggttc acatgttccg    300
ctcacgttcg gtggtgggac caagctggag ctgaaa                              336
```

<210> SEQ ID NO 54
<211> LENGTH: 354
<212> TYPE: DNA
<213> ORGANISM: Artificial Sequence
<220> FEATURE:
<223> OTHER INFORMATION: Synthesized

<400> SEQUENCE: 54

```
gaagtgcagc tggtggagtc tgggggaggc ttagtgcagc ctggagggtc cctgaaactc     60
tcctgtgcag cctctggatt cacttttagt aactattaca tgtcttgggt tcgccagact    120
ccagagaaga ggctggagtg ggtcgcatac attagtattg atggtaataa tatctaccat    180
ccagacagtg tgaagggtcg attcaccatc tccagagaca tgccaagaa caccctgtac    240
ctgcaaatga gcagtctgaa gtctgaggac acagccatgt attactgtgc aagagacagt    300
gactacggct acttcgatgt ctggggcaca gggaccacgg tcaccgtctc ctca          354
```

<210> SEQ ID NO 55
<211> LENGTH: 354
<212> TYPE: DNA
<213> ORGANISM: Artificial Sequence
<220> FEATURE:
<223> OTHER INFORMATION: Synthesized

<400> SEQUENCE: 55

```
gaggtgcagc tggtggagtc cggcggcggc ctggtgcagc ccggcggctc cctgcgcctg     60
tcctgcgccg cctccggctt caccttctcc aactactaca tgtcctgggt gcgccaggcc    120
cccggcaagg gcctggagtg ggtgtcctac atctccatcg acggcaacaa catctaccac    180
```

| | |
|---|---|
| cccgactccg tgaagggccg cttcaccatc tcccgcgaca acgccaagaa caccctgtac | 240 |
| ctgcagatga actccctgcg cgccgaggac accgccgtgt actactgcgc ccgcgactcc | 300 |
| gactacggct acttcgacgt gtggggccaa ggcaccctgg tgaccgtgtc ctca | 354 |

<210> SEQ ID NO 56
<211> LENGTH: 354
<212> TYPE: DNA
<213> ORGANISM: Artificial Sequence
<220> FEATURE:
<223> OTHER INFORMATION: Synthesized

<400> SEQUENCE: 56

| | |
|---|---|
| gaggtgcagc tggtggagtc cggcggcggc ctggtgcagc ccggcggctc cctgcgcctg | 60 |
| tcctgcgccg cctccggctt caccttctcc aactactaca tgtcctgggt gcgccaggcc | 120 |
| cccggcaagg gcctggagtg ggtggcctac atctccatcg acggcaacaa catctaccac | 180 |
| cccgactccg tgaagggccg cttcaccatc tcccgcgaca acgccaagaa caccctgtac | 240 |
| ctgcagatga actccctgcg cgccgaggac accgccgtgt actactgcgc ccgcgactcc | 300 |
| gactacggct acttcgacgt gtggggccaa ggcaccctgg tgaccgtgtc ctca | 354 |

<210> SEQ ID NO 57
<211> LENGTH: 354
<212> TYPE: DNA
<213> ORGANISM: Artificial Sequence
<220> FEATURE:
<223> OTHER INFORMATION: Synthesized

<400> SEQUENCE: 57

| | |
|---|---|
| gaggtgcagc tggtggagtc cggcggcggc ctggtgcagc ccggcggctc cctgcgcctg | 60 |
| tcctgcgccg cctccggctt caccttctcc aactactaca tgtcctgggt gcgccaggcc | 120 |
| cccggcaagg gcctggagtg ggtgtcctac atctccatcg acggcaacaa catctaccac | 180 |
| cccgactccg tgaagggccg cttcaccatc tcccgcgaca acgccaagtc caccctgtac | 240 |
| ctgcagatgt cctccctgcg cgccgaggac accgccgtgt actactgcgc ccgcgactcc | 300 |
| gactacggct acttcgacgt gtggggccaa ggcaccctgg tgaccgtgtc ctca | 354 |

<210> SEQ ID NO 58
<211> LENGTH: 354
<212> TYPE: DNA
<213> ORGANISM: Artificial Sequence
<220> FEATURE:
<223> OTHER INFORMATION: Synthesized

<400> SEQUENCE: 58

| | |
|---|---|
| gaggtgcagc tggtggagtc cggcggcggc ctggtgcagc ccggcggctc cctgcgcctg | 60 |
| tcctgcgccg cctccggctt caccttctcc aactactaca tgtcctgggt gcgccaggcc | 120 |
| cccggcaagg gcctggagtg ggtggcctac atctccatcg acggcaacaa catctaccac | 180 |
| cccgactccg tgaagggccg cttcaccatc tcccgcgaca acgccaagtc caccctgtac | 240 |
| ctgcagatgt cctccctgcg cgccgaggac accgccgtgt actactgcgc ccgcgactcc | 300 |
| gactacggct acttcgacgt gtggggccaa ggcaccctgg tgaccgtgtc ctca | 354 |

<210> SEQ ID NO 59
<211> LENGTH: 354
<212> TYPE: DNA
<213> ORGANISM: Artificial Sequence
<220> FEATURE:
<223> OTHER INFORMATION: Synthesized

<400> SEQUENCE: 59

```
gaggtgcagc tggtggagtc cggcggcggc ctggtgcagc ccggcggctc cctgaagctg        60
tcctgcgccg cctccggctt caccttctcc aactactaca tgtcctgggt gcgccaagcc       120
cccggcaagc gcctggagtg ggtgtcctac atctccatcg acggcaacaa catctaccac       180
cccgactccg tgaagggccg cttcaccatc tcccgcgaca acgccaagaa caccctgtac       240
ctgcagatga actccctgaa ggccgaggac accgccatgt actactgcgc ccgcgactcc       300
gactacggct acttcgacgt gtggggccaa ggcaccctgg tgaccgtgtc ctca             354
```

<210> SEQ ID NO 60
<211> LENGTH: 354
<212> TYPE: DNA
<213> ORGANISM: Artificial Sequence
<220> FEATURE:
<223> OTHER INFORMATION: Synthesized

<400> SEQUENCE: 60

```
gaggtgcagc tggtggagtc cggcggcggc ctggtgcagc ccggcggctc cctgaagctg        60
tcctgcgccg cctccggctt caccttctcc aactactaca tgtcctgggt gcgccaagcc       120
cccggcaagc gcctggagtg ggtggcctac atctccatcg acggcaacaa catctaccac       180
cccgactccg tgaagggccg cttcaccatc tcccgcgaca acgccaagaa caccctgtac       240
ctgcagatga actccctgaa ggccgaggac accgccatgt actactgcgc ccgcgactcc       300
gactacggct acttcgacgt gtggggccaa ggcaccctgg tgaccgtgtc ctca             354
```

<210> SEQ ID NO 61
<211> LENGTH: 336
<212> TYPE: DNA
<213> ORGANISM: Artificial Sequence
<220> FEATURE:
<223> OTHER INFORMATION: Synthesized

<400> SEQUENCE: 61

```
gacgtggtga tgacccagac cccccctgtcc ctgcccgtga cccccggcga gcccgcctcc       60
atctcctgcc gctcctccca gtccatcgtg cactccaacg gcaacaccta cctggagtgg      120
tacctgcaga agcccggcca gtcccccaag ctgctgatct acaaggtgtc caagcgcttc      180
tccggcgtgc ccgaccgctt ctccggctcc ggctccggca ccgacttcac cctgaagatc      240
tcccgcgtgg aggccgagga cgtgggcgtg tactactgct tccagggctc ccacgtgccc      300
ctgaccttcg gcggcggcac caaggtggag atcaaa                                 336
```

<210> SEQ ID NO 62
<211> LENGTH: 336
<212> TYPE: DNA
<213> ORGANISM: Artificial Sequence
<220> FEATURE:
<223> OTHER INFORMATION: Synthesized

<400> SEQUENCE: 62

```
gacatcgtga tgacccagac cccccctgtcc ctgcccgtga cccccggcga gcccgcctcc       60
atctcctgcc gctcctccca gtccatcgtg cactccaacg gcaacaccta cctggagtgg      120
tacctgcaga agcccggcca gtcccccaag ctgctgatct acaaggtgtc caagcgcttc      180
tccggcgtgc ccgaccgctt ctccggctcc ggctccggca ccgacttcac cctgaagatc      240
tcccgcgtgg aggccgagga cgtgggcgtg tactactgct tccagggctc ccacgtgccc      300
```

```
ctgaccttcg gcggcggcac caaggtggag atcaaa                                    336
```

```
<210> SEQ ID NO 63
<211> LENGTH: 10
<212> TYPE: PRT
<213> ORGANISM: Artificial Sequence
<220> FEATURE:
<223> OTHER INFORMATION: Synthesized

<400> SEQUENCE: 63

Gly Phe Thr Phe Ser Asn Tyr Tyr Met Ser
1               5                   10
```

…

ANTI-TRANSTHYRETIN ANTIBODIES

CROSS REFERENCE TO RELATED APPLICATIONS

This application is a divisional of U.S. Ser. No. 15/201,416 filed Jul. 2, 2016, which is a continuation in part of Ser. No. 15/009,666 filed Jan. 28, 2016, which claims the benefit of U.S. Provisional Application No. 62/109,001 filed Jan. 28, 2015 and U.S. Provisional Application No. 62/266,557 filed Dec. 11, 2015, each of which is incorporated by reference in its entirety.

REFERENCE TO A SEQUENCE LISTING

This application includes an electronic sequence listing in a file named 508913_SEQLST.txt, created Jan. 3, 2018 and containing 70,850 bytes, which is hereby incorporated by reference in its entirety for all purposes.

BACKGROUND

Several diseases are thought to be caused by the abnormal folding and aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Transthyretin (TTR) is one of the many proteins that are known to misfold and aggregate (e.g., undergo amyloidogenesis). Transthyretin-related amyloidosis encompasses two forms of disease: familial disease arising from misfolding of a mutated or variant TTR, and a sporadic, non-genetic disease caused by misaggregation of wild-type TTR. The process of TTR amyloidogenesis can cause pathology in the nervous system and/or heart, as well as in other tissues.

SUMMARY OF THE CLAIMED INVENTION

In one aspect, the invention provides antibodies that specifically bind transthyretin comprising three heavy chain CDRs and three light chain CDRs substantially from antibody 6C1. Some such antibodies comprise three Kabat heavy chain CDRs (SEQ ID NOS: 10-12, respectively) and three light CDRs (SEQ ID NOS: 18-20, respectively) of antibody 6C1. In some antibodies, the heavy chain CDR-H1 is a composite Kabat-Chothia CDR-H1 (SEQ ID NO: 63). Some such antibodies are monoclonal antibodies. Some such antibodies are chimeric, humanized, veneered, or human antibodies. Some such antibodies have a human IgG1 isotype. Some such antibodies have a human IgG2 or IgG4 isotype.

Some such antibodies are humanized or chimeric 6C1 antibodies that specifically bind to transthyretin, wherein 6C1 is a mouse antibody characterized by a mature heavy chain variable region of SEQ ID NO:1 and a mature light chain variable region of SEQ ID NO:13.

In some antibodies, the humanized mature heavy chain variable region comprises the three heavy chain CDRs of 6C1 and the humanized mature light chain variable region comprises the three light chain CDRs of 6C1. In some antibodies, the humanized mature heavy chain variable region comprises the three Kabat heavy chain CDRs of 6C1 (SEQ ID NOs:10-12) and the humanized mature light chain variable region comprises the three Kabat light chain CDRs of 6C1 (SEQ ID NOs:18-20).

In some antibodies, the humanized mature heavy chain variable region has an amino acid sequence at least 90% identical to SEQ ID NO:9 and the humanized mature light chain variable region has an amino acid sequence at least 90% identical to SEQ ID NO:17. In some such antibodies, position H77 is occupied by T. In some such antibodies, position H49 is occupied by A. In some such antibodies, positions H76 and H82(a) are occupied by S. In some such antibodies, position H49 is occupied by A. In some such antibodies, positions H19, H44, H83, and H89 are occupied by K, R, K, and M, respectively. In some such antibodies, position H49 is occupied by A. In some such antibodies, position L45 is occupied by K. In some such antibodies, position L2 is occupied by V.

Some antibodies comprise a mature heavy chain variable region having an amino acid sequence at least 95% identical to SEQ ID NO:9 and a mature light chain variable region having an amino acid sequence at least 95% identical to SEQ ID NO:17. Some antibodies comprise a mature heavy chain variable region having an amino acid sequence at least 98% identical to SEQ ID NO:9 and a mature light chain variable region having an amino acid sequence at least 98% identical to SEQ ID NO:17.

In some such antibodies, the mature heavy chain variable region has an amino acid sequence of SEQ ID NO:4. In some such antibodies, the mature heavy chain variable region has an amino acid sequence of SEQ ID NO:5. In some such antibodies, the mature heavy chain variable region has an amino acid sequence of SEQ ID NO:6. In some such antibodies, the mature heavy chain variable region has an amino acid sequence of SEQ ID NO:7. In some such antibodies, the mature heavy chain variable region has an amino acid sequence of SEQ ID NO:8. In some such antibodies, the mature heavy chain variable region has an amino acid sequence of SEQ ID NO:9.

In some such antibodies, the mature light chain variable region has an amino acid sequence of SEQ ID NO:16. In some such antibodies, the mature light chain variable region has an amino acid sequence of SEQ ID NO:17.

In some such antibodies, the mature heavy chain variable region has an amino acid sequence of SEQ ID NO:4 and the mature light chain variable region has an amino acid sequence of SEQ ID NO:16. In some such antibodies, the mature heavy chain variable region has an amino acid sequence of SEQ ID NO:4 and the mature light chain variable region has an amino acid sequence of SEQ ID NO:17.

In some such antibodies, the mature heavy chain variable region has an amino acid sequence of SEQ ID NO:5 and the mature light chain variable region has an amino acid sequence of SEQ ID NO:16. In some such antibodies, the mature heavy chain variable region has an amino acid sequence of SEQ ID NO:5 and the mature light chain variable region has an amino acid sequence of SEQ ID NO:17.

In some such antibodies, the mature heavy chain variable region has an amino acid sequence of SEQ ID NO:6 and the mature light chain variable region has an amino acid sequence of SEQ ID NO:16. In some such antibodies, the mature heavy chain variable region has an amino acid sequence of SEQ ID NO:6 and the mature light chain variable region has an amino acid sequence of SEQ ID NO:17.

In some such antibodies, the mature heavy chain variable region has an amino acid sequence of SEQ ID NO:7 and the mature light chain variable region has an amino acid sequence of SEQ ID NO:16. In some such antibodies, the mature heavy chain variable region has an amino acid sequence of SEQ ID NO:7 and the mature light chain variable region has an amino acid sequence of SEQ ID NO:17.

In some such antibodies, the mature heavy chain variable region has an amino acid sequence of SEQ ID NO:8 and the mature light chain variable region has an amino acid sequence of SEQ ID NO:16. In some such antibodies, the mature heavy chain variable region has an amino acid sequence of SEQ ID NO:8 and the mature light chain variable region has an amino acid sequence of SEQ ID NO:17.

In some such antibodies, the mature heavy chain variable region has an amino acid sequence of SEQ ID NO:9 and the mature light chain variable region has an amino acid sequence of SEQ ID NO:16. In some such antibodies, the mature heavy chain variable region has an amino acid sequence of SEQ ID NO:9 and the mature light chain variable region has an amino acid sequence of SEQ ID NO:17.

In some antibodies, the antibody is an intact antibody. In some antibodies, the antibody is a binding fragment. In some such antibodies, the binding fragment is a single-chain antibody, Fab, or Fab'2 fragment.

In some antibodies, the mature light chain variable region is fused to a light chain constant region and the mature heavy chain variable region is fused to a heavy chain constant region. In some such antibodies, the heavy chain constant region is a mutant form of a natural human heavy chain constant region which has reduced binding to a Fcγ receptor relative to the natural human heavy chain constant region. In some such antibodies, the heavy chain constant region is of IgG1 isotype. In some such antibodies, the mature heavy chain variable region is fused to a heavy chain constant region having the sequence of SEQ ID NO:26 and/or the mature light chain variable region is fused to a light chain constant region having the sequence of SEQ ID NO:28.

In some antibodies, any differences in CDRs of the mature heavy chain variable region and mature light chain variable region from SEQ ID NOS:1 and 13, respectively, reside in positions H60-H65.

In another aspect, the invention provides a pharmaceutical composition comprising the any of the above mentioned antibodies and a pharmaceutically acceptable carrier.

In another aspect, the invention provides a nucleic acid encoding the heavy chain and/or light chain of any of the above mentioned antibodies. In another aspect, the invention provides a recombinant expression vector comprising such a nucleic acid. In another aspect, the invention provides a host cell transformed with such a recombinant expression vector.

In another aspect, the invention provides a method of humanizing an antibody, the method comprising:
    (a) selecting an acceptor antibody;
    (b) identifying the amino acid residues of the mouse antibody to be retained;
    (c) synthesizing a nucleic acid encoding a humanized heavy chain comprising CDRs of the mouse antibody heavy chain and a nucleic acid encoding a humanized light chain comprising CDRs of the mouse antibody light chain; and
    (d) expressing the nucleic acids in a host cell to produce a humanized antibody;
wherein the mouse antibody comprises a heavy chain variable region having an amino acid sequence of SEQ ID NO:1 and a light chain variable region having an amino acid sequence of SEQ ID NO:13.

In another aspect, the invention provides a method of producing a humanized, chimeric, or veneered antibody, the method comprising:
    (a) culturing cells transformed with nucleic acids encoding the heavy and light chains of the antibody, so that the cells secrete the antibody; and
    (b) purifying the antibody from cell culture media;
wherein the antibody is a humanized, chimeric, or veneered form of 6C1.

In another aspect, the invention provides a method of producing a cell line producing a humanized, chimeric, or veneered antibody, the method comprising:
    (a) introducing a vector encoding heavy and light chains of an antibody and a selectable marker into cells;
    (b) propagating the cells under conditions to select for cells having increased copy number of the vector;
    (c) isolating single cells from the selected cells; and
    (d) banking cells cloned from a single cell selected based on yield of antibody;
wherein the antibody is a humanized, chimeric, or veneered form of 6C1.

Some such methods further comprise propagating the cells under selective conditions and screening for cell lines naturally expressing and secreting at least 100 mg/L/$10^6$ cells/24 h.

In another aspect, the invention provides a method of inhibiting or reducing aggregation of transthyretin in a subject having or at risk of developing a transthyretin-mediated amyloidosis, comprising administering to the subject an effective regime of any of the above mentioned antibodies, thereby inhibiting or reducing aggregation of transthyretin in the subject.

In any of the above methods, the transthyretin-mediated amyloidosis can be associated with a condition selected from any of cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, macular degeneration and a ligament or tendon disorder.

The invention further provides a method of treating a subject having or at risk of any of cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, macular degeneration and a ligament or tendon disorder, the method comprising administering to the subject an effective regime of the antibody of any one of claims.

In another aspect, the invention provides a method of inhibiting or reducing transthyretin fibril formation in a subject having or at risk of developing a transthyretin-mediated amyloidosis, comprising administering to the subject an effective regime of any of the above mentioned antibodies, thereby inhibiting or reducing transthyretin accumulation in the subject.

In another aspect, the invention provides a method of reducing transthyretin deposits in a subject having or at risk of developing a transthyretin-mediated amyloidosis, comprising administering to the subject an effective regime of any of the above mentioned antibodies, thereby reducing transthyretin deposits in the subject.

In another aspect, the invention provides a method of clearing aggregated transthyretin in a subject having or at risk of developing a transthyretin-mediated amyloidosis, comprising administering to the subject an effective regime of any of the above mentioned antibodies, thereby clearing aggregated transthyretin from the subject relative to a subject having or at risk of developing a transthyretin-mediated amyloidosis who has not received the antibody.

In another aspect, the invention provides a method of stabilizing a non-toxic conformation of transthyretin in a subject having or at risk of developing a transthyretin-mediated amyloidosis, comprising administering to the subject an effective regime of any of the above mentioned antibodies, thereby stabilizing a non-toxic conformation of transthyretin in the subject.

In another aspect, the invention provides a method of treating or effecting prophylaxis of a transthyretin-mediated amyloidosis in a subject, comprising administering to the subject an effective regime of any of the above mentioned antibodies.

In another aspect, the invention provides a method of delaying the onset of a transthyretin-mediated amyloidosis in a subject, comprising administering to the subject an effective regime of any of the above mentioned antibodies.

In another aspect, the invention provides a method of diagnosing a transthyretin-mediated amyloidosis in a subject, comprising contacting a biological sample from the subject with an effective amount of any of the above mentioned antibodies. Some such methods further comprise detecting the binding of antibody to transthyretin, wherein the presence of bound antibody indicates the subject has a transthyretin-mediated amyloidosis. Some such methods further comprise comparing binding of the antibody to the biological sample with binding of the antibody to a control sample, whereby increased binding of the antibody to the biological sample relative to the control sample indicates the subject has a transthyretin-mediated amyloidosis.

In some such methods, the biological sample and the control sample comprise cells of the same tissue origin. In some such methods, the biological sample and/or the control sample is blood, serum, plasma, or solid tissue. In some such methods, the solid tissue is from the heart, peripheral nervous system, autonomic nervous system, kidneys, eyes, or gastrointestinal tract.

In some methods, the transthyretin-mediated amyloidosis is a familial transthyretin amyloidosis or a sporadic transthyretin amyloidosis. In some such methods, the familial transthyretin amyloidosis is familial amyloid cardiomyopathy (FAC), familial amyloid polyneuropathy (FAP), or central nervous system selective amyloidosis (CNSA). In some such methods, the sporadic transthyretin amyloidosis is senile systemic amyloidosis (SSA) or senile cardiac amyloidosis (SCA).

In some methods, the transthyretin-mediated amyloidosis is associated with amyloid accumulation in the heart, peripheral nervous system, autonomic nervous system, kidneys, eyes, or gastrointestinal tract of the subject.

In another aspect, the invention provides a method of detecting the presence or absence of transthyretin deposits in a subject, comprising contacting a biological sample from the subject suspected of comprising the amyloid accumulation with an effective amount of any of the above mentioned antibodies. Some such methods further comprise detecting the binding of antibody to transthyretin, wherein detection of bound antibody indicates the presence of transthyretin deposits. Some such methods further comprise comparing binding of the antibody to the biological sample with binding of the antibody to a control sample, whereby increased binding of the antibody to the biological sample relative to the control sample indicates the subject has a transthyretin-mediated amyloidosis. In some such methods, the biological sample and the control sample comprise cells of the same tissue origin. In some such methods, the biological sample and/or the control sample is blood, serum, plasma, or solid tissue. In some such methods, the solid tissue is from the heart, peripheral nervous system, autonomic nervous system, kidneys, eyes, or gastrointestinal tract.

In another aspect, the invention provides a method of determining a level of transthyretin deposits in a subject, comprising administering any of the above mentioned antibodies and detecting the presence of bound antibody in the subject. In some such methods, the presence of bound antibody is determined by positron emission tomography (PET).

BRIEF DESCRIPTION OF THE DRAWINGS

The patent application file contains at least one drawing executed in color. Copies of this patent application with color drawing(s) will be provided by the Office upon request and payment of the necessary fee.

FIG. 1 depicts an alignment of heavy chain variable regions of the mouse 6C1 antibody, mouse model antibodies, human acceptor antibodies, and humanized versions of the 6C1 antibody. The CDRs as defined by Kabat are enclosed in boxes, except that the first enclosed box is a composite of the Chothia CDR-H1 and the Kabat CDR-H1, with the Kabat CDR-H1 underlined and bolded.

FIG. 2 depicts an alignment of light chain variable regions of the mouse 6C1 antibody, mouse model antibodies, human acceptor antibodies, and humanized versions of the 6C1 antibody. The CDRs as defined by Kabat are enclosed in boxes.

FIG. 3A depicts the binding curve of murine 5A1, 6C1, 9D5, and 14G8 antibodies to ph4-treated TTR. FIG. 3B depicts the binding curve of murine 5A1, 6C1, 9D5, and 14G8 antibodies to ph4-treated or native TTR FIG. 4A depicts the inhibition of TTR-Y78F fiber formation by mis-TTR antibodies. FIG. 4B depicts the inhibition of TTR-V122I fiber formation by 14G8.

FIG. 4C depicts the inhibition of TTR-V122I fiber formation by a control antibody.

FIG. 5A depicts a densitometry analysis of a Western Blot analysis of plasma samples from patients confirmed for V30M ATTR (Sample #11, #12, #15, #18, #19, ##20) and samples from normal subjects (Sample #21, #22, #23, #24, #25, and #27) using the 9D5 mis-TTR antibody. FIG. 5B depicts a densitometry analysis of a Western blot analysis of the same samples using the 5A1 mis-TTR antibody.

FIG. 7A depicts the effect of antibody 14G8 on the uptake of F87M/L110M TTR by THP-1 cells. FIG. 7B depicts the effect of each of the mis-TTR antibodies on the uptake of V30M TTR by THP-1 cells.

FIGS. 8A-C and FIG. 8D. 1-2 14G8 binds to TTR-V122I fibril ends and to oligomeric aggregates as assessed using TEM and AFM. Immunogold labeling with 14G8 was observed in TTR-V122I oligomer aggregates and fibril ends (FIG. 8A), whereas immunogold labeling with an anti-TTR pAb showed binding along the lengths of TTR fibers and to oligomeric clusters (FIG. 8B). IgG1 isotype control mAb did not show immunogold labeling (FIG. 8C). TTR-V122I fibers, alone and in the presence of 14G8±6 nm colloidal gold-conjugated secondary antibody, were assessed using AFM. Gold labeling was observed at fiber ends (FIG. 8D)

FIG. 10A. 1-2, 10B. 1-2, 10C. 1-2, 10D-F, and 10G. 1-3 show 14G8 immunolabeled TTR amyloid present between fibers of the nerve fascicle a patient with ATTR amyloidosis resulting from a TTR-V30M mutation. FIG. 10A panels 1 and 2 show amyloid between fibers of the nerve fascicle, which overlapped with staining by Congo red (FIG. 8B panels 1 and 2) and thioflavin T (FIG. 10C panels 1 and 2), and immunolabeling by a total-TTR antibody (FIG. 10D) in tissue derived from a patient with ATTR amyloidosis. No staining was seen with the use of 2 isotype control antibodies (FIGS. 10E-F); however, axonal degeneration (lack of Schwann cell nuclei) in the areas laden with TTR amyloid deposits were also observed (FIGS. 10E-F [red areas in 6E]). Peripheral nerves from a healthy control were not labeled using either 14G8 or a total-TTR antibody (FIG. 10G panels 1-3).

FIG. 11A. 1-3, 11B. 1-3, 11C. 1-3, 11D. 1-3 and 11E. 1-4 shows antibody 14G8 immunolabels TTR amyloid in the gastrointestinal tract derived from a patient with TTR-C30M amyloidosis. FIG. 11A, B panels 1 show Meissner's plexus and glands in the esophagus, FIG. 11C panel 1 shows the rich vasculature bed in the submucosa, FIG. 11D panel 1 shows the muscularis propria (MP) and muscularis mucosa 14G8-positive TTR amyloid overlapped with Congo red fluorescent staining (FIGS. 11A-D panels 2). FIGS. 11A-D panels 3 show ATTR amyloidosis tissue stained with an isotype control mAb 14G8 immunoreactivity was absent in healthy control tissue (FIG. 11 panels 1-4).

FIGS. 12A-12D show exemplary humanized Vh designs, with backmutations and other mutations based on selected human frameworks. The gray-shaded areas in the first column indicate the CDRs as defined by Chothia, and the gray-shaded areas in the remaining columns indicate the CDRs as defined by Kabat.

FIGS. 13A-13D show exemplary humanized Vk designs, with backmutations and other mutations based on selected human frameworks. The gray-shaded areas in the first column indicate the CDRs as defined by Chothia, and the gray-shaded areas in the remaining columns indicate the CDRs as defined by Kabat.

BRIEF DESCRIPTION OF THE SEQUENCES

Figure 3A:
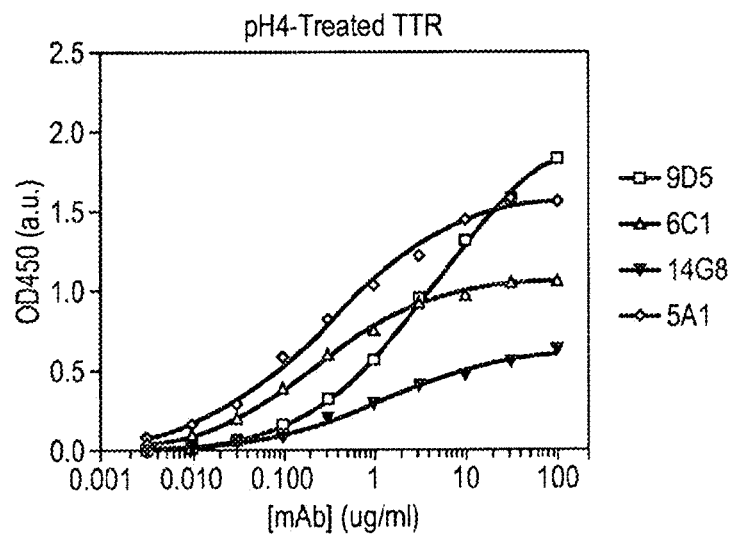
FIGS. 3A & 3B.

SEQ ID NO:1 sets forth the amino acid sequence of the heavy chain variable region of the mouse 6C1 antibody.

SEQ ID NO:2 sets forth the amino acid sequence of the mouse heavy chain variable region structure template.

SEQ ID NO:3 sets forth the amino acid sequence of the heavy chain variable acceptor accession number ADX65650.

SEQ ID NO:4 sets forth the amino acid sequence of the heavy chain variable region of the humanized 6C1 antibody version 1 (Hu6C1VHv1).

SEQ ID NO:5 sets forth the amino acid sequence of the heavy chain variable region of the humanized 6C1 antibody version 1b (Hu6C1VHv1b).

SEQ ID NO:6 sets forth the amino acid sequence of the heavy chain variable region of the humanized 6C1 antibody version 2 (Hu6C1VHv2).

SEQ ID NO:7 sets forth the amino acid sequence of the heavy chain variable region of the humanized 6C1 antibody version 2b (Hu6C1VHv2b).

SEQ ID NO:8 sets forth the amino acid sequence of the heavy chain variable region of the humanized 6C1 antibody version 3 (Hu6C1VHv3).

SEQ ID NO:9 sets forth the amino acid sequence of the heavy chain variable region of the humanized 6C1 antibody version 3b (Hu6C1VHv3b).

SEQ ID NO:10 sets forth the amino acid sequence of Kabat CDR-H1 of the mouse 6C1 antibody.

SEQ ID NO:11 sets forth the amino acid sequence of Kabat CDR-H2 of the mouse 6C1 antibody.

SEQ ID NO:12 sets forth the amino acid sequence of Kabat CDR-H3 of the mouse 6C1 antibody.

SEQ ID NO:13 sets forth the amino acid sequence of the light chain variable region of the mouse 6C1 antibody.

SEQ ID NO:14 sets forth the amino acid sequence of the mouse light chain variable region structure template.

SEQ ID NO:15 sets forth the amino acid sequence of the light chain variable acceptor accession number ABI74084.

SEQ ID NO:16 sets forth the amino acid sequence of the light chain variable region of the humanized 6C1 antibody version 1 (Hu6C1VLv1).

SEQ ID NO:17 sets forth the amino acid sequence of the light chain variable region of the humanized 6C1 antibody version 2 (Hu6C1VLv2).

SEQ ID NO:18 sets forth the amino acid sequence of Kabat CDR-L1 of the mouse 6C1 antibody.

SEQ ID NO:19 sets forth the amino acid sequence of Kabat CDR-L2 of the mouse 6C1 antibody.

SEQ ID NO:20 sets forth the amino acid sequence of Kabat CDR-L3 of the mouse 6C1 antibody.

SEQ ID NO:21 sets forth a nucleic acid sequence encoding the heavy chain variable region of the mouse 6C1 antibody with signal peptide.

SEQ ID NO:22 sets forth the amino acid sequence of the heavy chain variable region of the mouse 6C1 antibody with signal peptide.

SEQ ID NO:23 sets forth a nucleic acid sequence encoding the light chain variable region of the mouse 6C1 antibody with signal peptide.

SEQ ID NO:24 sets forth the amino acid sequence of the light chain variable region of the mouse 6C1 antibody with signal peptide.

SEQ ID NO:25 sets forth the amino acid sequence of an exemplary IgG1 heavy chain constant region.

SEQ ID NO:26 sets forth the amino acid sequence of an exemplary IgG1 G1m3 heavy chain constant region.

SEQ ID NO:27 sets forth the amino acid sequence of an exemplary IgG1 G1m3 heavy chain constant region.

SEQ ID NO:28 sets forth the amino acid sequence of an exemplary light chain constant region with C-terminal Arginine.

SEQ ID NO:29 sets forth the amino acid sequence of an exemplary light chain constant region without C-terminal Arginine.

SEQ ID NO:30 sets forth the amino acid sequence of the heavy chain region of the humanized 6C1 antibody version 1.

SEQ ID NO:31 sets forth the amino acid sequence of the heavy chain region of the humanized 6C1 antibody version 1b.

SEQ ID NO:32 sets forth the amino acid sequence of the heavy chain region of the humanized 6C1 antibody version 2.

SEQ ID NO:33 sets forth the amino acid sequence of the heavy chain region of the humanized 6C1 antibody version 2b.

SEQ ID NO:34 sets forth the amino acid sequence of the heavy chain region of the humanized 6C1 antibody version 3.

SEQ ID NO:35 sets forth the amino acid sequence of the heavy chain region of the humanized 6C1 antibody version 3b.

SEQ ID NO:36 sets forth the amino acid sequence of the light chain region of the humanized 6C1 antibody version 1.

SEQ ID NO:37 sets forth the amino acid sequence of the light chain region of the humanized 6C1 antibody version 2.

SEQ ID NO:38 sets forth the amino acid sequence of human transthyretin set forth in accession number P02766.1 (UniProt).

SEQ ID NO:39 sets forth the amino acid sequence of human transthyretin set forth in accession number AAB35639.1 (GenBank).

SEQ ID NO:40 sets forth the amino acid sequence of human transthyretin set forth in accession number AAB35640.1 (GenBank).

SEQ ID NO:41 sets forth the amino acid sequence of human transthyretin set forth in accession number and ABI63351.1 (GenBank).

SEQ ID NO:42 sets forth the amino acid sequence of residues 89-97 of human transthyretin.

SEQ ID NO:43 sets forth the amino acid sequence of a potential transthyretin immunogen.

SEQ ID NO:44 sets forth the amino acid sequence of a potential transthyretin immunogen.

SEQ ID NO:45 sets forth the amino acid sequence of a potential transthyretin immunogen.

SEQ ID NO:46 sets forth a nucleic acid sequence encoding an exemplary IgG1 G1m3 heavy chain constant region.

SEQ ID NO:47 sets forth a nucleic acid sequence encoding an exemplary light chain constant region with C-terminal Arginine.

SEQ ID NO:48 sets forth a nucleic acid sequence encoding an exemplary light chain constant region without C-terminal Arginine.

SEQ ID NO:49 sets forth the amino acid sequence of a heavy chain constant region signal peptide.

SEQ ID NO:50 sets forth a nucleic acid sequence encoding a heavy chain constant region signal peptide.

SEQ ID NO:51 sets forth the amino acid sequence of a light chain constant region signal peptide.

SEQ ID NO:52 sets forth a nucleic acid sequence encoding a light chain constant region signal peptide.

SEQ ID NO:53 sets forth a nucleic acid sequence encoding a mouse 6C1 variable light chain region.

SEQ ID NO:54 sets forth a nucleic acid sequence encoding a mouse 6C1 variable heavy chain region.

SEQ ID NO:55 sets forth a nucleic acid sequence encoding a heavy chain variable region of the humanized 6C1 antibody version 1 (Hu6C1VHv1).

SEQ ID NO:56 sets forth a nucleic acid sequence encoding a heavy chain variable region of the humanized 6C1 antibody version 1b (Hu6C1VHv1b).

SEQ ID NO:57 sets forth a nucleic acid sequence encoding a heavy chain variable region of the humanized 6C1 antibody version 2 (Hu6C1VHv2).

SEQ ID NO:58 sets forth a nucleic acid sequence encoding a heavy chain variable region of the humanized 6C1 antibody version 2b (Hu6C1VHv2b).

SEQ ID NO:59 sets forth a nucleic acid sequence encoding a heavy chain variable region of the humanized 6C1 antibody version 3 (Hu6C1VHv3).

SEQ ID NO:60 sets forth a nucleic acid sequence encoding a heavy chain variable region of the humanized 6C1 antibody version 3b (Hu6C1VHv3b).

SEQ ID NO:61 sets forth a nucleic acid sequence encoding a light chain variable region of the humanized 6C1 antibody version 1 (Hu6C1VLv1).

SEQ ID NO:62 sets forth a nucleic acid sequence encoding a light chain variable region of the humanized 6C1 antibody version 2 (Hu6C1VLv2).

SEQ ID NO:63 sets forth the amino acid sequence of a composite CDR-H1 (residues 26-35) of the mouse 6C1 antibody.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, Md., 1987 and 1991), The Chothia definition (Chothia & Lesk, *J. Mol. Biol.* 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

The term "antibody" includes intact antibodies and binding fragments thereof. Typically, fragments compete with the intact antibody from which they were derived for specific binding to the target including separate heavy chains, light chains Fab, Fab', F(ab')2, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.*, 79:315-321 (1990); Kostelny et al., *J. Immunol.*, 148:1547-53 (1992)). In some bispecific antibodies, the two different heavy/light chain pairs include a humanized 6C1 heavy chain/light chain pair and a heavy chain/light chain pair specific for a different epitope on transthyretin than that bound by 6C1.

In some bispecific antibodies, one heavy chain/light chain pair is a humanized 6C1 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments

TABLE 1

Conventional Definitions of CDRs Using Kabat Numbering

| Loop | Kabat | Chothia | Composite of Chothia & Kabat | AbM | Contact |
| --- | --- | --- | --- | --- | --- |
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32..H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996). The epitope can be linear, such as an epitope of, for example, 2-5, 3-5, 3-9, or 5-9 contiguous amino acids from SEQ ID NO:38. The epitope can also be a conformational epitope including, for example, two or more non-contiguous segments of amino acids within residues 89-97 of SEQ ID NO:38. If an antibody is said to bind to an epitope within amino acids 89-97 of transthyretin (TTR), for example, what is meant is that the epitope is within the recited range of amino acids including those defining the outer-limits of the range. It does not necessarily mean that every amino acid within the range constitutes part of the epitope. Thus, for example, an epitope within amino acids 89-97 of TTR may consist of amino acids 89-97, 89-96, 90-96, 91-96, 92-96, 93-96, 94-96, 89-96, 89-95, 89-94, 89-93, 89-92 or 89-93, among other linear segments of SEQ ID NO:42, or in the case of conformational epitopes, non-contiguous segments of amino acids of SEQ ID NO:42.

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "native" with respect to the structure transthyretin (TTR) refers to the normal folded structure of TTR in its properly functioning state (i.e., a TTR tetramer). As TTR is a tetramer in its natively folded form, non-native forms of TTR include, for example, misfolded TTR tetramers, TTR monomers, aggregated forms of TTR, and fibril forms of TTR. Non-native forms of TTR can include molecules comprising wild-type TTR amino acid sequences or mutations.

The term "misfolded" with respect to TTR refers to the secondary and tertiary structure of a TTR polypeptide monomer or multimer, and indicates that the polypeptide has adopted a conformation that is not normal for that protein in its properly functioning state. Although TTR misfolding can be caused by mutations in the protein (e.g., deletion, substitution, or addition), wild-type TTR proteins can also be misfolded in diseases, exposing specific epitopes.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include monomeric, misfolded, aggregated, or fibril forms of transthyretin (TTR), such as in TTR amyloid deposits. Control samples can be obtained from individuals not afflicted with a TTR amyloidosis or a specifically chosen type of TTR amyloidosis. Alternatively, control samples can be obtained from patients afflicted with TTR amyloidosis or a specifically chosen type of TTR amyloidosis. Such samples can be obtained at the same time as a biological sample thought to comprise the TTR amyloidosis or on a different occasion. A biological sample and a control sample can both be obtained from the same tissue (e.g., a tissue section containing both TTR amyloid deposits and surrounding normal tissue). Preferably, control samples consist essentially or entirely of tissue free of TTR amyloid deposits and can be used in comparison to a biological sample thought to comprise TTR amyloid deposits. Preferably, the tissue in the control sample is the same type as the tissue in the biological sample (e.g., cardiomyocytes in the heart).

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

Statistical significance means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to residues 89-97 of transthyretin (TTR). The antibodies have the capacity to bind to monomeric, misfolded, aggregated, or fibril forms of TTR. The antibodies can be used for treating or effecting prophylaxis of diseases or disorders associated with TTR accumulation or accumulation of TTR deposits (e.g., TTR amyloidosis). The antibodies can also be used for diagnosing TTR amyloidosis and inhibiting or reducing aggregation of TTR, among other applications.

II. Target Molecules

Transthyretin (TTR) is a 127-amino acid, 55 kDa serum and cerebrospinal fluid transport protein primarily synthesized by the liver. It has also been referred to as prealbumin, thyroxine binding prealbumin, ATTR, and TBPA. In its native state, TTR exists as a tetramer. In homozygotes, the tetramers comprise identical 127-amino-acid beta-sheet-rich subunits. In heterozygotes, the TTR tetramers are made up of variant and/or wild-type subunits, typically combined in a statistical fashion.

The established function of TTR in the blood is to transport holo-retinol binding protein. Although TTR is the major carrier of thyroxine (T4) in the blood of rodents, utilizing binding sites that are orthogonal to those used for holo-retinol binding protein, the T4 binding sites are effectively unoccupied in humans.

TTR is one of at least thirty different human proteins whose extracellular misfolding and/or misassembly (amyloidogenesis) into a spectrum of aggregate structures is thought to cause degenerative diseases referred to as amyloid diseases. TTR undergoes conformational changes in order to become amyloidogenic. Partial unfolding exposes stretches of largely uncharged hydrophobic residues in an extended conformation that efficiently misassemble into largely unstructured spherical aggregates that ultimately undergo conformation conversion into cross-beta sheet amyloid structures.

Unless otherwise apparent from context, reference to transthyretin (TTR) or its fragments or domains includes the natural human amino acid sequences including isoforms, mutants, and allelic variants thereof. Exemplary TTR polypeptide sequences are designated by Accession Numbers P02766.1 (UniProt) (SEQ ID NO:38), AAB35639.1 (GenBank) (SEQ ID NO:39), AAB35640.1 (GenBank) (SEQ ID NO:40), and ABI63351.1 (GenBank) (SEQ ID NO:41). Residues are numbered according to Swiss Prot P02766.1, with the first amino acid of the mature protein (i.e., not including the 20 amino acid signal sequence) designated residue 1. In any other TTR protein, residues are numbered according to the corresponding residues in P02766.1 on maximum alignment.

III. Transthyretin Amyloidosis

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. See, e.g., Almeida and Saraiva, *FEBS Letters* 586:2891-2896 (2012); Ando et al., *Orphanet Journal of Rare Diseases* 8:31 (2013).

In humans, both wild-type TTR tetramers and mixed tetramers comprised of mutant and wild-type subunits can dissociate, misfold, and aggregate, with the process of amyloidogenesis leading to the degeneration of post-mitotic tissue. Thus, TTR amyloidoses encompass diseases caused by pathogenic misfolded TTR resulting from mutations in TTR or resulting from non-mutated, misfolded TTR.

For example, senile systemic amyloidosis (SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. The TTR amyloidoses associated with point mutations in the TTR gene include familial amyloid polyneuropathy (FAP), familial amyloid cardiomyopathy (FAC), and the rare central nervous system selective amyloidosis (CNSA). Patients with hereditary (familial) TTR amyloidosis are almost always heterozygotes, meaning that the TTR tetramers are composed of mutant and/or wild-type TTR subunits, generally statistically distributed. Hereditary (familial) versions of TTR amyloidosis are generally autosomal dominant and are typically earlier onset than the sporadic diseases (SSA and SCA).

There are over 100 mutations in the gene encoding TTR that have been implicated in the autosomal dominant disorders FAP and FAC. See, e.g., US 2014/0056904; Saraiva, *Hum. Mutat.* 17(6):493-503 (2001); Damas and Saraiva, *J. Struct. Biol.* 130:290-299; Dwulet and Benson, *Biochem. Biophys. Res. Commun.* 114:657-662 (1983). These amyloid-causing mutations are distributed throughout the entire molecule of TTR. Generally, the more destabilizing the mutant subunits are to the TTR tetramer structure, the earlier the onset of amyloid disease. The pathogenic potential of a TTR variant is generally determined by a combination of its instability and its cellular secretion efficiency. The initial pathology caused by some TTR variants comes from their selective destruction of cardiac tissue, whereas that from other TTR variants comes from compromising the peripheral and autonomic nervous system. The tissue damage caused by TTR amyloidogenesis appear to stem largely from the toxicity of small, diffusible TTR aggregates, although accumulation of extracellular amyloid may contribute and almost certainly compromises organ structure in the late stages of the TTR amyloidosis.

TTR amyloidosis presents in many different forms, with considerable phenotypic variation across individuals and geographic locations. For example, TTR amyloidosis can present as a progressive, axonal sensory autonomic and motor neuropathy. TTR amyloidosis can also present as an infiltrative cardiomyopathy.

The age at onset of disease-related symptoms varies between the second and ninth decades of life, with great variations across different populations. The multisystem involvement of TTR amyloidosis is a clue to its diagnosis. For example, TTR amyloidosis diagnosis is considered when one or several of the following are present: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic gladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., *Orphanet Journal of Rare Diseases* 8:31 (2013). Other symptoms can include, for example, polyneuropathy, sensory loss, pain, weakness in lower limbs, dyshidrosis, diarrhea, constipation, weight loss, and urinary incontinence/retention.

Diagnosis of TTR amyloidosis typically relies on target organ biopsies, followed by histological staining of the excised tissue with the amyloid-specific dye, Congo red. If a positive test for amyloid is observed, immunohistochemical staining for TTR is subsequently performed to ensure that the precursor protein responsible for amyloid formation is indeed TTR. For familial forms of the diseases, demonstration of a mutation in the gene encoding TTR is then needed before diagnosis can be made. This can be accomplished, for example, through isoelectric focusing electrophoresis, polymerase chain reaction, or laser dissection/liquid chromatography-tandem mass spectrometry. See, e.g., US 2014/0056904; Ruberg and Berk, Circulation 126:1286-1300 (2012); Ando et al., *Orphanet Journal of Rare Diseases* 8:31 (2013).

IV. Antibodies

A. Binding Specificity and Functional Properties

The invention provides monoclonal antibodies binding to transthyretin (TTR) protein, more specifically, to epitopes within amino acid residues 89-97 (SEQ ID NO:42) of TTR. Such epitopes are buried in the native TTR tetramer and exposed in monomeric, misfolded, aggregated, or fibril forms of TTR.

An antibody designated 6C1 is such an exemplary mouse antibody. This antibody specifically binds within amino acid residues 89-97 (SEQ ID NO:42) of TTR. This antibody is further characterized by its ability to bind to monomeric, misfolded, aggregated, or fibril forms of TTR but not to native tetrameric forms of TTR. In addition, this antibody is characterized by its immunoreactivity on TTR-mediated amyloidosis cardiac tissue but not on healthy cardiac tissue. Ability to bind to specific proteins or fragments thereof may be demonstrated using exemplary assay formats provided in the examples.

Some antibodies bind to the same or overlapping epitope as an antibody designated 6C1. The sequences of the heavy and light chain mature variable regions of 6C1 are designated SEQ ID NOS: 1 and 13, respectively. Other antibodies having such a binding specificity can be produced by immunizing mice with TTR, or a portion thereof including the desired epitope (e.g., SEQ ID NO:42), and screening resulting antibodies for binding to monomeric TTR or a peptide comprising SEQ ID NO:42, optionally in competition with an antibody having the variable regions of mouse 6C1 (IgG1,kappa). Fragments of TTR including the desired epitope can be linked to a carrier that helps elicit an antibody response to the fragment and/or be combined with an adjuvant that helps elicit such a response. Such antibodies can be screened for differential binding to wild-type, monomeric versions of TTR or a fragment thereof (e.g., SEQ ID NO:38) compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 6C1) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding (e.g., at least $10^8$ and preferably at least $10^9 M^{-1}$) for monomeric TTR or a fragment thereof (e.g., amino acid residues 89-97) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for monomeric TTR or a fragment thereof (e.g., amino acid residues 89-97) are selected. The resulting antibodies usually have the same or similar epitope specificity as the murine starting material.

Other antibodies can be obtained by mutagenesis of cDNA encoding the heavy and light chains of an exemplary antibody, such as 6C1. Monoclonal antibodies that are at least 70%, 80%, 90%, 95%, 96%, 97%, 98%, or 99% identical to 6C1 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by conventional definition, but preferably Kabat, that are 90%, 95%, 99% or 100% identical to corresponding CDRs of 6C1 are also included.

The invention also provides antibodies having some or all (e.g., 3, 4, 5, and 6) CDRs entirely or substantially from 6C1. Such antibodies can include a heavy chain variable region that has at least two, and usually all three, CDRs entirely or substantially from the heavy chain variable region of 6C1 and/or a light chain variable region having at least two, and usually all three, CDRs entirely or substantially from the light chain variable region of 6C1. The antibodies can include both heavy and light chains. A CDR is substantially from a corresponding 6C1 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 6C1 in the amino acid sequence of the mature heavy and/or light chain variable regions and maintain their functional properties, and/or differ from 6C1 by a small number of functionally inconsequential amino acid substitutions (e.g., conservative substitutions), deletions, or insertions.

Some antibodies identified by such assays can bind to monomeric, misfolded, aggregated, or fibril forms of TTR but not to native tetrameric forms of TTR, as described in the examples or otherwise. Likewise, some antibodies are immunoreactive on TTR-mediated amyloidosis tissue but not on healthy tissue.

Some antibodies can inhibit or reduce aggregation of TTR, inhibit or reduce TTR fibril formation, reduce or clear TTR deposits or aggregated TTR, or stabilize non-toxic conformations of TTR in an animal model or clinical trial. Some antibodies can treat, effect prophylaxis of, or delay the onset of a TTR amyloidosis as shown in an animal model or clinical trial. Exemplary animal models for testing activity against a TTR amyloidosis include those described in Kohno et al., *Am. J. Path.* 150(4):1497-1508 (1997); Teng et al., *Laboratory Investigations* 81:385-396 (2001); Wakasugi et al., Proc. Japan Acad. 63B:344-347 (1987); Shimada et al., *Mol. Biol. Med.* 6:333-343 (1989); Nagata et al., *J Biochem.* 117:169-175 (1995); Sousa et al., *Am. J. Path.* 161:1935-1948 (2002); and Santos et al., *Neurobiology of Aging* 31:280-289 (2010).

B. Non-Human Antibodies

The production of other non-human antibodies, e.g., murine, guinea pig, primate, rabbit or rat, against monomeric TTR or a fragment thereof (e.g., amino acid residues 89-97) can be accomplished by, for example, immunizing the animal with TTR or a fragment thereof. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to monomeric TTR or an epitope within TTR (e.g., an epitope comprising one or more of amino acid residues 89-97). Such screening can be accomplished by determining binding of an antibody to a collection of monomeric TTR variants, such as TTR variants containing amino acid residues 89-97 or mutations within these residues, and determining which TTR variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by any conventional definition but preferably defined by Kabat are identical.

Although humanized antibodies often incorporate all six CDRs (preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.*, 320: 415-428, 2002; Iwahashi et al., *Mol. Immunol.* 36:1079-1091, 1999; Tamura et al, *J. Immunol.*, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the heavy chain is the human mature heavy chain variable region with NCBI accession code ADX65650 (SEQ ID NO:3). This acceptor sequence includes two CDRs having the same canonical form as mouse 6C1 heavy chain. An examples of an acceptor sequence for the light chain is the human mature light chain variable region with NCBI accession code ABI74084 (SEQ ID NO:15). This acceptor sequence includes two CDRs having the same canonical form as mouse 6C1 light chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Exemplary humanized antibodies are humanized forms of the mouse 6C1 antibody, designated Hu6C1. The mouse antibody comprises mature heavy and light chain variable regions having amino acid sequences comprising SEQ ID NO:1 and SEQ ID NO:13, respectively. The invention provides six exemplified humanized mature heavy chain variable regions: Hu6C1VHv1 (SEQ ID NO:4), Hu6C1VHv1b (SEQ ID NO:5), Hu6C1VHv2 (SEQ ID NO:6), Hu6C1VHv2b (SEQ ID NO:7), Hu6C1VHv3 (SEQ ID NO:8), and Hu6C1VHv3b (SEQ ID NO:9). The invention further provides two exemplified human mature light chain variable regions: Hu6C1VLv1 (SEQ ID NO:16) and Hu6C1VLv2 (SEQ ID NO:17). FIGS. 1 and 2 show alignments of the heavy chain variable region and light chain variable region, respectively, of 6C1, mouse model antibodies, human acceptor antibodies, and humanized antibody versions of 6C1.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following ten variable region framework positions were considered as candidates for substitutions in the six exemplified human mature light chain variable regions and the two exemplified human mature heavy chain variable regions, as further specified in the examples: L2, L45, H19, H44, H49, H76, H77, H82(a), H83, and H89.

Here, as elsewhere, the first-mentioned residue is the residue of a humanized antibody formed by grafting Kabat CDRs or a composite Chothia Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions (e.g., Hu6C1VHv1/VLv1 or H1L1, Hu6C1VHv1b/VLv1 or H1bL1, Hu6C1VHv1/VLv2 or H1L2, Hu6C1VHv1b/VLv2 or H1bL2, Hu6C1VHv2/VLv1 or H2L1, Hu6C1VHv2b/VLv1 or H2bL1, Hu6C1VHv2/VLv2 or H2L2, Hu6C1VHv2b/VLv2 or H2bL2, Hu6C1VHv3/VLv1 or H3L1, Hu6C1VHv3b/VLv1 or H3bL1, Hu6C1VHv3/VLv2 or H3L2, and Hu6C1VHv3b/VLv2 or H3bL2).

The invention provides variants of humanized antibodies in which the humanized mature heavy chain variable region shows at least 90%, 95%, 96%, 97%, 98%, or 99% identity to SEQ ID NOs:4-9, and the humanized mature light chain variable region shows at least 90%, 95%, 96%, 97%, 98%, or 99% identity to SEQ ID NOs:16 or 17. In some such antibodies at least 1, 2, 3, 4, 5, 6, 7, 8, 9, or all 10 of the backmutations or other mutations in SEQ ID NOs:4-9, 16, and 17 are retained.

In some antibodies, at least one of positions H19, H44, H49, H76, H77, H82(a), H83, and H89 in the $V_H$ region is occupied by K, R, A, S, T, S, K, and V, respectively. In some antibodies, position H77 in the $V_H$ region is occupied by T, as in Hu6C1VHv1. In some antibodies, positions H49 and H77 in the $V_H$ region are occupied by A and T, respectively, as in Hu6C1VHv1b. In some antibodies, positions H76, H77, and H82(a) in the $V_H$ region are occupied by S, T, and S, respectively, as in Hu6C1VHv2. In some antibodies, positions H49, H76, H77, and H82(a) in the $V_H$ region are occupied by A, S, T, and S, respectively, as in Hu6C1VHv2b. In some antibodies, positions H19, H44, H77, H83, and H89 in the $V_H$ region are occupied by K, R, T, K, and M, respectively, as in Hu6C1VHv3. In some antibodies, positions H19, H44, H49, H77, H83, and H89 in the $V_H$ region are occupied by K, R, A, T, K, and M, respectively, as in Hu6C1VHv3b. In some antibodies, position L45 in the VL region is occupied by K. In some antibodies, position L2 in the $V_L$ region is occupied by I. In some antibodies, one or both of positions L2 and L45 in the $V_L$ region are occupied by V and K, respectively, as in Hu6C1VLv1. In some antibodies, one or both of positions L2 and L45 in the $V_L$ region are occupied by I and K, respectively, as in Hu6C1VLv2. The CDR regions of such humanized antibodies can be identical or substantially identical to the CDR regions of the 6C1 mouse donor antibody. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu6C1 antibodies by a small number (e.g., typically no more than 1, 2, 3, 5, 10, or 15) of replacements, deletions or insertions. Such differences are usually in the framework but can also occur in the CDRs.

A possibility for additional variation in humanized 6C1 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in Hu6C1 variants (whether or not conservative) have no substantial effect on the binding affinity or potency of the humanized mAb, that is, its ability to bind to monomeric TTR (e.g., the potency in some or all of the assays described in the present examples of the variant humanized 6C1 antibody is essentially the same, i.e., within experimental error, as that of murine 6C1).

D. Chimeric and Veneered Antibodies

The invention further provides chimeric and veneered forms of non-human antibodies, particularly the 6C1 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 6C1 antibody are included in the invention.

E. Human Antibodies

Human antibodies against monomeric TTR or a fragment thereof (e.g., amino acid residues 89-97 (SEQ ID NO:42) of TTR) are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for particular epitope specificity by using only a fragment of TTR, such as a TTR variant containing only amino acid residues 89-97 of TTR, as the target antigen, and/or by screening antibodies against a collection of TTR variants, such as TTR variants containing various mutations within amino acid residues 89-97 of TTR.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, *Nat. Biotechnol.* 14:826 (1996); and Kucherlapati, WO 91/10741 (1991)) and phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRT receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO:27. In some antibodies, the isotype is human IgG2 or IgG4.

An exemplary human light chain kappa constant region has the amino acid sequence of SEQ ID NO:28. The N-terminal arginine of SEQ ID NO:28 can be omitted, in which case light chain kappa constant region has the amino acid sequence of SEQ ID NO:29. An exemplary human IgG1 heavy chain constant region has the amino acid sequence of SEQ ID NO:25 (with or without the C-terminal lysine). Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence of SEQ ID NO:26. Another heavy chain constant region of the IgG1 G1m3 allotype has the amino acid sequence of SEQ ID NO:27 (with or without the C-terminal lysine). Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO:46, which encodes a human IgG1 constant region, and SEQ ID NOs:47 and 48, which encode a human kappa light chain constant region.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

H. Antibody Screening Assays

Antibodies can be subject to several screens including binding assays, functional screens, screens in animal models of diseases associated with TTR deposits, and clinical trials. Binding assays test for specific binding and, optionally, affinity and epitope specificity to monomeric TTR or a fragment thereof. For example, binding assays can screen for antibodies that bind to amino acid residues 89-97 (SEQ ID NO:42) of TTR, which is an epitope that is buried in the native TTR tetramer and exposed in monomeric, misfolded, aggregated, or fibril forms of TTR. Antibodies can also be screened for the ability to bind pre-fibrillar, non-native conformations of TTR and TTR amyloid fibrils but not native TTR conformations. For example, antibodies can be screened for the ability to bind to monomeric forms of TTR created by dissociation or disaggregation of native tetrameric TTR, and can be counter-screened against native tetrameric TTR, as described in the examples or otherwise. Likewise, antibodies can also be screened for their immunoreactivity on TTR-mediated amyloidosis tissue but not on healthy tissue. Such screens are sometimes performed in competition with an exemplary antibody, such as an antibody having the variable regions of 6C1 or IgG1 kappa isotype. Optionally, either the antibody or TTR target is immobilized in such assay.

Functional assays can be performed in cellular models including cells naturally expressing TTR or transfected with DNA encoding TTR or a fragment thereof. Suitable cells include cells derived from cardiac tissue or other tissues affected by TTR amyloidogenesis. Cells can be screened for reduced levels of monomeric, misfolded, aggregated, or fibril forms of TTR (e.g., by Western blotting or immunoprecipitation of cell extracts or supernatants) or reduced toxicity attributable to monomeric, misfolded, aggregated, or fibril forms of TTR. For example, antibodies can tested for the ability to inhibit or reduce aggregation of TTR, inhibit or reduce TTR fibril formation, reduce TTR deposits, clear aggregated TTR, or stabilize non-toxic conformations of TTR.

Other functional assays can be performed in solution, such as testing whether an antibody is capable of disrupting or reducing TTR fibril formation when monomeric TTR or misfolded TTR intermediates in solution are contacted with the antibody. The extent of fibril formation can be probed by turbidity measurements, for example, at 400 nm on a UV-visible spectrometer equipped with a temperature control unit. Thioflavin-T can also be used to assess the extent of amyloid fibril formation. For example, a five-fold molar excess of Thioflavin-T can be added to TTR samples and left at room temperature for 30 minutes before measurements are taken. Thioflavin-T fluorescence can be monitored using a spectrofluorimeter. See US 2014/0056904.

Animal model screens test the ability of the antibody to therapeutically or prophylactically treat signs or symptoms in an animal model simulating a human disease associated with accumulation of TTR or TTR deposits. Such diseases include types of TTR amyloidosis, such as senile systemic amyloidosis (SSA), senile cardiac amyloidosis (SCA), familial amyloid polyneuropathy (FAP), familial amyloid cardiomyopathy (FAC), and central nervous system selective amyloidosis (CNSA). Suitable signs or symptoms that can be monitored include the presence and extent of amyloid deposits in various tissues, such as the gastrointestinal tract or heart. The extent of reduction of amyloid deposits can be determined by comparison with an appropriate control, such the level of TTR amyloid deposits in control animals that have received a control antibody (e.g., an isotype matched control antibody), a placebo, or no treatment at all. An exemplary animal model for testing activity against a TTR amyloidosis is a mouse model carrying a null mutation at the endogenous mouse Ttr locus and the human mutant TTR gene comprising a V30M mutation that is associated with familial amyloidotic polyneuropathy. See, e.g., Kohno et al., *Am. J. Path.* 150(4):1497-1508 (1997); Cardoso and Saraiva, *FASEB J* 20(2):234-239 (2006). Similar models also exist, including other models for familial versions of TTR amyloidosis and models for sporadic versions of TTR amyloidosis. See, e.g., Teng et al., *Lab. Invest.* 81(3): 385-396 (2001); Ito and Maeda, Mouse Models of Transthyretin Amyloidosis, in Recent Advances in Transthyretin Evolution, Structure, and Biological Functions, pp. 261-280 (2009) (Springer Berlin Heidelberg). Transgenic animals can include a human TTR transgene, such as a TTR transgene with a mutation associated with TTR amyloidosis or a wild-type TTR transgene. To facilitate testing in animal models, chimeric antibodies having a constant region appropriate for the animal model can be used (e.g., mouse-rat chimeras could be used for testing antibodies in rats). It can be concluded that a humanized version of an antibody will be effective if the corresponding mouse antibody or chimeric antibody is effective in an appropriate animal model and the humanized antibody has similar binding affinity (e.g., within experimental error, such as by a factor of 1.5, 2, or 3).

Clinical trials test for safety and efficacy in a human having a disease associated with TTR amyloidosis.

I. Nucleic Acids

The invention further provides nucleic acids encoding any of the heavy and light chains described above (e.g., SEQ ID NOS:4-9, 16, and 17). Optionally, such nucleic acids further encode a signal peptide and can be expressed with the signal peptide linked to the constant region (e.g., signal peptides having amino acid sequences of SEQ ID NOS:49 (heavy chain) and 51 (light chain) that can be encoded by SEQ ID NOS:50, respectively (heavy chain) and 52, respectively (light chain)). Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens exposed in pathogenic forms of TTR but not in native tetrameric forms of TTR, such as amino acid residues 89-97 (SEQ ID NO:42) of TTR, are useful in detecting the presence of monomeric, misfolded, aggregated, or fibril forms of TTR; monitoring and evaluating the efficacy of therapeutic agents being used to treat patients diagnosed with a TTR amyloidosis; inhibiting or reducing aggregation of TTR; inhibiting or reducing TTR fibril formation; reducing or clearing TTR deposits; stabilizing non-toxic conformations of TTR; or treating or effecting prophylaxis of a TTR amyloidosis in a patient. For example, such antibodies can be conjugated with other therapeutic moieties, other proteins, other antibodies, and/or detectable labels. See WO 03/057838; U.S. Pat. No. 8,455,622.

Conjugated therapeutic moieties can be any agent that can be used to treat, combat, ameliorate, prevent, or improve an unwanted condition or disease in a patient, such as a TTR amyloidosis. Therapeutic moieties can include, for example, immunomodulators or any biologically active agents that facilitate or enhance the activity of the antibody. An immunomodulator can be any agent that stimulates or inhibits the development or maintenance of an immunologic response. If such therapeutic moieties are coupled to an antibody specific for monomeric, misfolded, aggregated, or fibril forms of TTR, such as the antibodies described herein, the coupled therapeutic moieties will have a specific affinity for non-native, pathogenic forms of TTR over native tetrameric forms of TTR. Consequently, administration of the conjugated antibodies directly targets tissues comprising pathogenic forms of TTR with minimal damage to surrounding normal, healthy tissue. This can be particularly useful for therapeutic moieties that are too toxic to be administered on their own. In addition, smaller quantities of the therapeutic moieties can be used.

Examples of suitable therapeutic moieties include drugs that reduce levels of TTR, stabilize the native tetrameric structure of TTR, inhibit aggregation of TTR, disrupt TTR fibril or amyloid formation, or counteract cellular toxicity. See, e.g., Almeida and Saraiva, *FEBS Letters* 586:2891-2896 (2012); Saraiva, *FEBS Letters* 498:201-203 (2001); Ando et al., *Orphanet Journal of Rare Diseases* 8:31 (2013); Ruberg and Berk, *Circulation* 126:1286-1300 (2012); and Johnson et al., *J. Mol. Biol.* 421(2-3):185-203 (2012). For example, antibodies can be conjugated to tafamidis, diflunisal, ALN-TTR01, ALNTTR02, ISIS-TTRRx, doxycycline (doxy), tauroursodeoxycholic acid (TUDCA), Doxy-TUDCA, epigallocatechin gallate (EGCG), curcumin, or resveratrol (3,5,4'-trihydroxystilbene). Other representative therapeutic moieties include other agents known to be useful for treatment, management, or amelioration of a TTR amyloidosis or symptoms of a TTR amyloidosis. See, e.g., Ando et al., *Orphanet Journal of Rare Diseases* 8:31 (2013) for common clinical symptoms of TTR amyloidosis and typical agents used to treat those symptoms.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007);

Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within TTR or a portion thereof or can bind to a different target antigen.

Antibodies can also be coupled with a detectable label. Such antibodies can be used, for example, for diagnosing a TTR amyloidosis, for monitoring progression of a TTR amyloidosis, and/or for assessing efficacy of treatment. Such antibodies are particularly useful for performing such determinations in subjects having or being susceptible to a TTR amyloidosis, or in appropriate biological samples obtained from such subjects. Representative detectable labels that may be coupled or linked to a humanized 6C1 antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as yttrium$^{90}$ (90Y), radiosilver-111, radiosilver-199, Bismuth$^{213}$, iodine ($^{131}$I, $^{125}$I, $^{123}$I, $^{121}$I,), carbon ($^{14}$C), sulfur ($^5$S), tritium ($^3$H), indium ($^{115}$In, $^{113}$In, $^{112}$In, $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Therapeutic moieties, other proteins, other antibodies, and/or detectable labels may be coupled or conjugated, directly or indirectly through an intermediate (e.g., a linker), to a murine, chimeric, veneered, or humanized 6C1 antibody using techniques known in the art. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.,* 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

V. Therapeutic Applications

The above antibodies can be used for treating or effecting prophylaxis of a disease in a patient having or at risk for the disease mediated at least in part by transthyretin (TTR), and particularly by monomeric, misfolded, aggregated, or fibril forms of TTR. Although an understanding of mechanism is not required for practice, it is believed that any or all of the following mechanisms may contribute to treatment of TTR amyloidosis using the above antibodies: antibody-mediated inhibition of TTR aggregation and fibril formation, antibody-mediated stabilization of non-toxic conformations of TTR (e.g., tetrameric forms), or antibody-mediated clearance of aggregated TTR, oligomeric TTR, or monomeric TTR. Antibody-drug conjugates can have additional mechanisms of action determined by the conjugated moiety.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

VI. Pharmaceutical Compositions and Methods of Use

Provided herein are several methods of diagnosing, monitoring, treating or effecting prophylaxis of diseases or conditions mediated at least in part by transthyretin (TTR), and particularly by monomeric, misfolded, aggregated, or fibril forms of TTR (e.g., TTR amyloidosis). Examples of such diseases include familial TTR amyloidoses, such as familial amyloid cardiomyopathy (FAC) or cardiomyopathy or hypertrophy in athletes or others undergoing extreme aerobic exercise, familial amyloid polyneuropathy (FAP), or central nervous system selective amyloidosis (CNSA), and sporadic TTR amyloidoses, such as senile systemic amyloidosis (SSA) or senile cardiac amyloidosis (SCA). TTR amyloidosis can also be associated as a cause or result of various diseases and conditions characterized by tissue or organ degeneration or trauma. Accumulation of TTR deposits contributes to organ or tissue dysfunction associated with the disease or condition. An example of such a condition amenable to treatment or prophylaxis with the present agents and methods is spinal stenosis (Westermark et al., Upsala J. Medical Sciences 119, 223-238 (2014) and Yanagisawa et al., Modern Pathology 28, 201-207 (2015). Another disease likewise amenable to treatment or prophylaxis is osteoarthritis (Takanashi et al., Amyloid 20, 151-155 (2013), Gu et al., Biomed & Biotechnol. 15, 92-99; Takinami et al., Biomarker Insights 8, 85-95 (2014); Akasaki et al., Arthritis Rheumatol. 67, 2097-2107 (2015). Another disease likewise amenable to treatment or prophylaxis is rheumatoid arthritis (Clement et al., JCI Insight 1 epublish (2016). Another disease amenable to treatment or prophylaxis is juvenile idiopathic arthritis (Sharma et al., PLOSone 9, 1-12 (2014). Another disease amenable to treatment or prophylaxis is age related macular degeneration (wet or dry). Another class of conditions likewise amenable to treatment or prophylaxis are ligament and tendon disorders, such as disorders of the rotator cuff (Sueyoshi et al., Human Pathol. 42, 1259-64 (2011).

Antibodies described above can be incorporated into a pharmaceutical composition for use treatment or prophylaxis of any of the above diseases and conditions. In general, an antibody or pharmaceutical composition containing an antibody is administered to a subject in need thereof. Patients amenable to treatment include individuals at risk of TTR amyloidosis but not showing symptoms, as well as patients presently showing symptoms. Some patients can be treated during the prodromal stage of TTR amyloidosis.

Individuals suffering from TTR amyloidosis can sometimes be recognized from the clinical manifestations of TTR amyloidosis, including one or more of the following: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic gladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., Orphanet Journal of Rare Diseases 8:31 (2013). Definitive diagnosis of TTR amyloidosis, however, typically relies on target organ biopsies, followed by histological staining of the excised tissue with the amyloid-specific dye, Congo red. If a positive test for amyloid is observed, immunohistochemical staining for TTR is subsequently performed to ensure that the precursor protein responsible for amyloid formation is indeed TTR. For familial forms of the diseases, demonstration of a mutation in the gene encoding TTR is then needed before a definitive diagnosis can be made.

The identification of the subject can occur in a clinical setting, or elsewhere, such as in the subject's home, for example, through the subject's own use of a self-testing kit. For example, the subject can be identified based on various symptoms such as peripheral neuropathy (sensory and motor), autonomic neuropathy, gastrointestinal impairment, cardiomyopathy, nephropathy, or ocular deposition. See Ando et al., Orphanet Journal of Rare Diseases 8:31 (2013). The subject can also be identified by increased levels of non-native forms of TTR in plasma samples from the subject compared to control samples, as disclosed in the examples.

As warranted by family history, genetic testing, or medical screening for TTR amyloidosis, treatment can begin at any age (e.g., 20, 30, 40, 50, 60, or 70 years of age). Treatment typically entails multiple dosages over a period of time and can be monitored by assaying antibody or activated T-cell or B-cell responses to a therapeutic agent (e.g., a truncated form of TTR comprising amino acid residues 89-97) over time. If the response falls, a booster dosage is indicated.

In prophylactic applications, an antibody or a pharmaceutical composition of the same is administered to a subject susceptible to, or otherwise at risk of a disease (e.g., TTR amyloidosis) in a regime (dose, frequency and route of administration) effective to reduce the risk, lessen the severity, or delay the onset of at least one sign or symptom of the disease. In therapeutic applications, an antibody or immunogen to induce an antibody is administered to a subject suspected of, or already suffering from a disease (e.g., TTR amyloidosis) in a regime (dose, frequency and route of administration) effective to ameliorate or at least inhibit further deterioration of at least one sign or symptom of the disease.

A regime is considered therapeutically or prophylactically effective if an individual treated subject achieves an outcome more favorable than the mean outcome in a control population of comparable subjects not treated by methods disclosed herein, or if a more favorable outcome is demonstrated for a regime in treated subjects versus control subjects in a controlled clinical trial (e.g., a phase II, phase II/III, or phase III trial) or an animal model at the $p<0.05$ or 0.01 or even 0.001 level.

An effective regime of an antibody can be used for, e.g., inhibiting or reducing aggregation of TTR in a subject having or at risk of a condition associated with TTR accumulation; inhibiting or reducing TTR fibril formation in a subject having or at risk of a condition associated with TTR accumulation; reducing or clearing TTR deposits or aggregated TTR in a subject having or at risk of a condition associated with TTR accumulation; stabilizing non-toxic conformations of TTR in a subject having or at risk of a condition associated with TTR accumulation; inhibiting toxic effects of TTR aggregates, fibrils or deposits in a subject having or at risk of a condition associated with TTR accumulation; diagnosing the presence or absence of TTR amyloid accumulation in a tissue suspected of comprising the amyloid accumulation; determining a level of TTR deposits in a subject by detecting the presence of bound antibody in the subject following administration of the antibody; detecting the presence of monomeric, misfolded, aggregated, or fibril forms of TTR in a subject; monitoring and evaluating the efficacy of therapeutic agents being used to treat patients diagnosed with a TTR amyloidosis; inducing an immune response comprising antibodies to TTR in a subject; delaying the onset of a condition associated with TTR amyloid accumulation in a subject; or treating or effecting prophylaxis of a TTR amyloidosis in a patient.

Effective doses vary depending on many different factors, such as means of administration, target site, physiological state of the subject, whether the subject is human or an animal, other medications administered, and whether treatment is prophylactic or therapeutic.

An exemplary dose range for antibodies can be from about 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Antibody can be administered in such doses daily, on alternative days, weekly, fortnightly, monthly, quarterly, or according to any other schedule determined by empirical analysis. An exemplary treatment entails administration in multiple doses over a prolonged period, for example, of at least six months. Additional exemplary treatment regimes entail administration once per every two weeks or once a month or once every 3 to 6 months.

Antibodies can be administered via a peripheral route. Routes of administration include topical, intravenous, oral, subcutaneous, intraarterial, intracranial, intrathecal, intraperitoneal, intranasal or intramuscular. Routes for administration of antibodies can be intravenous or subcutaneous. Intravenous administration can be, for example, by infusion over a period such as 30-90 min. This type of injection is most typically performed in the arm or leg muscles. In some methods, agents are injected directly into a particular tissue where deposits have accumulated, for example intracranial injection.

Pharmaceutical compositions for parenteral administration can be sterile and substantially isotonic (250-350 mOsm/kg water) and manufactured under GMP conditions. Pharmaceutical compositions can be provided in unit dose form (i.e., the dose for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with another agent effective in treatment or prophylaxis of the disease being treated. Such agents can include siRNA to inhibit expression of TTR or Vyndaqel, a stabilizer of TTR in tetramer formation.

After treatment, the subject's condition can be evaluated to determine the progress or efficacy of such treatment. Such methods preferably test for changes in TTR amyloid levels or levels of non-native forms of TTR. For example, TTR amyloid levels may be evaluated to determine improvement relative to the subject's TTR amyloid levels under comparable circumstances prior to treatment. The subject's TTR amyloid levels can also be compared with control populations under comparable circumstances. The control populations can be similarly afflicted, untreated subjects or normal untreated subjects (among other control subjects). Improvement relative to similarly afflicted, untreated subjects or levels approaching or reaching the levels in untreated normal subjects indicates a positive response to treatment.

TTR amyloid levels can be measured by a number of methods, including imaging techniques. Examples of suitable imaging techniques include PET scanning with radio-labeled TTR of fragments thereof, TTR antibodies or fragments thereof, Congo-red-based amyloid imaging agents, such as, e.g., PIB (US 2011/0008255), amyloid-imaging peptide p31 (Biodistribution of amyloid-imaging peptide, p31, correlates with amyloid quantitation based on Congo red tissue staining, Wall et al., Abstract No. 1573, 2011 ISNM Annual Meeting), and other PET labels. Levels of non-native forms of TTR can be measured, for example, by performing SDS-PAGE/Western blot or Meso Scale Discovery plate assays with the antibodies disclosed herein on plasma samples or biopsy samples from a subject and comparing to control samples, as described in the examples.

A. Diagnostics and Monitoring Methods

Also provided are methods of detecting an immune response against TTR in a patient suffering from or susceptible to diseases associated with TTR deposition or pathogenic forms of TTR (e.g., monomeric, misfolded, aggregated, or fibril forms of TTR). The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to TTR in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting monomeric, misfolded, aggregated, or fibril forms of TTR in a subject, for example, by measuring TTR amyloid or pathogenic forms of TTR (e.g., monomeric, misfolded, aggregated, or fibril forms of TTR) in a sample from a subject or by in vivo imaging of TTR in a subject. Such methods are useful to diagnose or confirm diagnosis of diseases associated with such pathogenic forms of TTR (e.g., TTR amyloidosis), or susceptibility thereto. The methods can also be used on asymptomatic subjects. The presence of monomeric, misfolded, aggregated, or fibril forms of TTR indicates susceptibility to future symptomatic disease. The methods are also useful for monitoring disease progression and/or response to treatment in subjects who have been previously diagnosed with a TTR amyloidosis.

Biological samples obtained from a subject having, suspected of having, or at risk of having a TTR amyloidosis can be contacted with the antibodies disclosed herein to assess the presence of monomeric, misfolded, aggregated, or fibril forms of TTR. For example, levels of monomeric, misfolded, aggregated, or fibril forms of TTR in such subjects may be compared to those present in healthy subjects. Alternatively, levels of TTR amyloid or pathogenic forms of TTR (e.g., monomeric, misfolded, aggregated, or fibril forms of TTR) in such subjects receiving treatment for the disease may be compared to those of subjects who have not been treated for a TTR amyloidosis. Some such tests involve a biopsy of tissue obtained from such subjects. ELISA assays may also be useful methods, for example, for assessing levels of monomeric, misfolded, aggregated, or fibril forms of TTR in fluid samples. Some such ELISA assays involve anti-TTR antibodies that preferentially bind monomeric, misfolded, aggregated, or fibril forms of TTR relative to normal tetrameric forms of TTR.

The in vivo imaging methods can work by administering a reagent, such as antibody that binds to monomeric, misfolded, aggregated, or fibril forms of TTR in the subject, and then detecting the reagent after it has bound. Such antibodies typically bind to an epitope within residues 89-97 of TTR. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the subject, or via other routes deemed reasonable. The dose of reagent should be within the same ranges as for treatment methods. Typically, the reagent is labeled, although in some methods, the primary reagent with affinity for monomeric, misfolded, aggregated, or fibril forms of TTR is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. A decrease in values relative to base line generally signals a positive response to treatment.

IX. Kits

The invention further provides kits (e.g., containers) comprising the humanized 6C1 antibodies disclosed herein and related materials, such as instructions for use (e.g., package insert). The instructions for use may contain, for example, instructions for administration of the antibodies and optionally one or more additional agents. The containers of antibodies may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

X. Other Applications

The antibodies can be used for detecting monomeric, misfolded, aggregated, or fibril forms of transthyretin (TTR), or fragments thereof, in the context of clinical diagnosis or treatment or in research. For example, the antibodies can be used to detect the presence of monomeric, misfolded, aggregated, or fibril forms of TTR in a biological sample as an indication that the biological sample comprises TTR amyloid deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of monomeric, misfolded, aggregated, or fibril forms of TTR) to the biological sample(s) is increased, decreased, or the same relative to antibody binding to the control sample(s). Increased binding of the antibody to the biological sample(s) relative to the control sample(s) indicates the presence of monomeric, misfolded, aggregated, or fibril forms of TTR in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of monomeric, misfolded, aggregated, or fibril forms of TTR in a biological sample to monitor and evaluate the efficacy of a therapeutic agent being used to treat a patient diagnosed with a TTR amyloidosis. A biological sample from a patient diagnosed with a TTR amyloidosis is evaluated to establish a baseline for the binding of the antibodies to the sample (i.e., a baseline for the presence of the monomeric, misfolded, aggregated, or fibril forms of TTR in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of monomeric, misfolded, aggregated, or fibril forms of TTR) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of monomeric, misfolded, aggregated, or fibril forms of TTR) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of monomeric, misfolded, aggregated, or fibril forms of TTR), it can be concluded that the therapeutic agent was effective in treating the TTR amyloidosis in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of TTR amyloidosis.

The antibodies can also be used as research reagents for laboratory research in detecting monomeric, misfolded, aggregated, or fibril forms of TTR, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify monomeric, misfolded, aggregated, or fibril forms of TTR, or binding partners of monomeric, misfolded, aggregated, or fibril forms of TTR, e.g., by affinity chromatography.

The antibodies can also be used for inhibiting or reducing aggregation of TTR, inhibiting or reducing TTR fibril formation, reducing or clearing TTR deposits or TTR aggregates, or stabilizing non-toxic conformations of TTR in a biological sample. The biological sample can comprise, for example, blood, serum, plasma, or tissue (e.g., tissue from the heart, peripheral nervous system, autonomic nervous system, kidneys, eyes, or gastrointestinal tract). In some instances, TTR aggregation, TTR fibril formation, or TTR deposits are inhibited or reduced by at least 10%, 20%, 25%, 30%, 40%, 50%, or 75%, (e.g., 10%-75% or 30%-70%). Assays for detecting fibril formation are described elsewhere herein. See also US 2014/0056904.

Antibody 6C1 has been deposited subject to the Budapest Treaty under accession number PTA-124077 on Apr. 4, 2017 at the American Type Culture Collection 10801 University Boulevard Manassas, Va. 20110 USA. All restrictions imposed by the depositor on the availability to the public of the deposited material will be irrevocably removed on the granting of a patent except as permitted under 37 CFR 1.808(b).

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of Mis-TTR Monoclonal Antibodies

Conformationally-specific monoclonal antibodies against monomeric, mis-folded, fibril, or aggregated forms of TTR (mis-TTR) were generated, screened, expressed, and purified as described in Materials and Methods (a-d). In order to generate mis-TTR monoclonal antibodies, the crystal structure of human tetrameric TTR was examined to find regions of the protein that are buried in the tetramer, but exposed upon dissociation of the tetramer into its monomeric subunits. The region identified was residues 89-97 (EHAEVVFTA) (SEQ ID NO:42) located within the F strand of TTR and sequestered at the dimer interface of the tetrameric protein. A BLAST search of the protein database did not reveal any other human proteins possessing this sequence.

A peptide comprising this sequence (ggEHAEVVFTAgkg) (SEQ ID NO:43), was synthesized. Capitalized letters represent residues 89-97 of TTR. Lower case letters represent additional linker residues added to increase the solubility of the antigenic peptide and to establish the 9 amino acid fragment as an internal sequence. This peptide was linked to a poly-lysine dendritic core, generating a multiple antigenic peptide immunogen (TTR-MAP) comprising a core of lysine residues with multiple branches linked to the TTR 89-97 peptide. The antibodies listed in Table 2 were generated against TTR-MAP.

In addition to this multiple antigenic peptide, two other immunogens containing the same TTR fragment were generated by covalently linking similar TTR 89-97 peptides (Ac-cggEHAEVVFTA-amide (SEQ ID NO:44) and Ac-EHAEVVFTAcgg-amide) (SEQ ID NO:45) via the N- and C-terminal cysteine residues to keyhole limpet hemocyanin (TTR89-97-N-KLH and TTR89-97-C-KLH).

Following antibody generation, screening, expression, and purification, detailed binding kinetic parameters (association rate ($k_a$), dissociation rate ($k_d$), and binding affinity constant ($K_D$)) were determined for lead mis-TTR antibodies by Surface Plasmon Resonance (SPR) for recombinant human TTR F87M/L110M, as shown in Table 2. Anti-mouse IgG (GE Healthcare) was immobilized on a sensor chip C5 (lacking dextran chains) via amine coupling following the instructions provided in the GE Healthcare anti-mouse kit, and mis-TTR mAbs were captured to a level to ensure a maximum binding of analyte of 30-50 RU. Various concentrations of analyte (recombinant human TTR F87M/L110M) were passed over the captured ligand at 30 µl/min in running buffer (HBS+0.05% P-20, 1 mg/mL BSA) in 3-fold dilutions. For each concentration, the reaction proceeded for a time frame allowing for the higher analyte concentrations to reach equilibrium during association, as well as at least 10% of signal to decay during dissociation. At least one concentration (not the highest or lowest) was run in duplicate. Concentration ranges of analyte were selected based on preliminary experimentation to span at least 10-fold above $K_D$ to 10-fold below $K_D$.

The results of SPR analysis of lead mis-TTR mAbs is shown in Table 2 below.

TABLE 2

SPR Analysis of Lead mis-TTR Antibodies Binding to Human TTR (F87M/L110M)

| mAb | $k_a$(1/Ms) | $k_d$(1/s) | $K_D$(M) | $R_{max}$ |
|---|---|---|---|---|
| 9D5 | 2.715E+4 | 4.930E-4 | 1.816E-8 | 31.55 |
| 14G8 | 2.880E+4 | 5.358E-4 | 1.861E-8 | 27.13 |
| 5A1 | 6.107E+4 | 4.693E-4 | 7.684E-9 | 30.98 |
| 6C1 | 4.607E+4 | 4.151E-4 | 9.010E-9 | 26.32 |

Example 2. Binding of Mis-TTR Antibodies to TTR Antigen

Four lead mis-TTR mAbs (9D5, 14G8, 6C1, and 5A1) were assayed by ELISA at concentrations ranging from 0.31 to 2.5 µg/ml using both pH4.0-treated TTR (pH4-TTR) and native TTR as the coating antigen. TTR antigen preparation and ELISA protocols are described elsewhere in Materials and Methods (e-g).

Figure 3B:
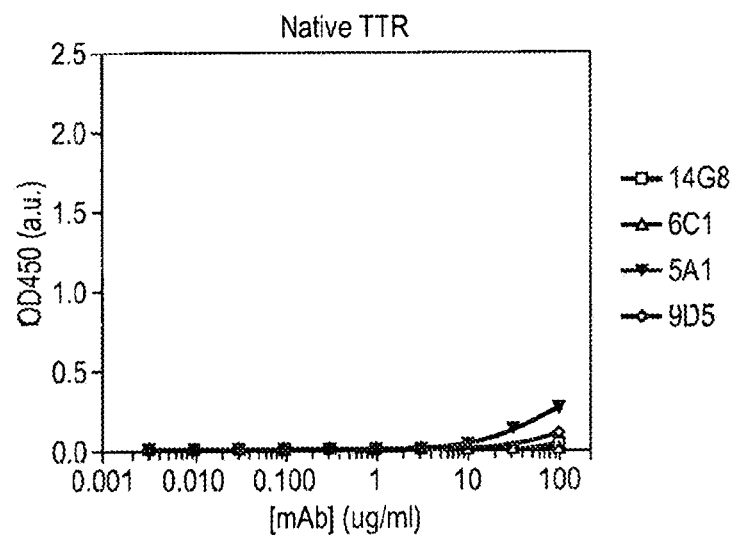

The resulting binding curves and tabulated $K_d$ and $B_{max}$ values are shown in FIG. 3 and Table 3 below. The results in FIG. 3 are presented in arbitrary units (a.u.) on the y-axis. All mAbs showed significant binding to pH4-TTR with $K_d$ values ranging from 16 nM (6C1) to 282 nM (9D5). $B_{max}$ values for binding to pH4-TTR ranged from a low of 0.65 a.u. (14G8) to a high of 2.02 (9D5). In contrast to the binding to pH4-TTR, none of the antibodies showed significant binding to native TTR, indicating that all TTR antibodies generated were specific for non-native forms of TTR.

TABLE 3

ELISA Analysis of Lead mis-TTR Antibodies Binding to pH4-TTR

| mAb | $K_d$ (nM) | $B_{max}$ (a.u.) |
|---|---|---|
| 9D5 | 282 | 2.02 |
| 14G8 | 108 | 0.65 |
| 6C1 | 16 | 1.07 |
| 5A1 | 23 | 1.61 |

Example 3. Analysis of Mis-TTR Antibodies by SDS-PAGE and Native-PAGE

9D5 and 14G8 were analyzed by SDS-PAGE/Western to demonstrate specificity of binding toward monomeric/denatured forms of TTR versus native, non-denatured TTR. SDS-PAGE, Native-PAGE, and Western Blot protocols are described elsewhere in the Methods and Materials (h-j).

Non-denatured TTR or pH4-TTR was run on an SDS-PAGE gel alongside heat-denatured TTR and heat-denatured pH4-TTR. After electrophoresis, the gel was Western blotted onto nitrocellulose and stained with TTR mAbs 9D5 and 14G8. Both antibodies only recognized TTR when it was treated at pH4 or when TTR or pH4-TTR was first heat-denatured prior to SDS-PAGE. These 9D5 and 14G8 thus show a specificity for TTR conformers generated either by denaturation of TTR or by treatment of TTR at pH4.

6C1 and 5A1 along with total TTR mAbs (7G7, 8C3) and the commercially available Sigma polyclonal antibody were also analyzed by SDS-PAGE/Western. Each blot contained stained molecular weight markers, non-denatured TTR, and pH4-TTR.

The stained SDS-PAGE gel showed that the major species present in the non-denatured TTR sample was an ~38 kDa dimer. In contrast, the major component present in the pH4-TTR sample ran as an ~35 kDa dimer with a small amount of dimer of an ~15 kDa monomer. This dimer ran as a slightly smaller protein than the dimer present in the non-denatured TTR sample, indicating a conformational difference between these two TTR dimer species.

The Western blots of TTR and pH4-TTR using the four mis-TTR antibodies showed that these mAbs do not recognize non-denatured TTR, but do bind to both the denatured monomer and dimer present in the pH4-TTR sample. Thus, the four mis-TTR mAbs (9D5, 14G8, 6C1, and 5A1) show similar specificities for non-native conformations of TTR when analyzed by SDS-PAGE/Westerns.

In contrast to the four mis-TTR mAbs, the two TTR control mAbs, 7G7 and 8C3 generated through immunization of mice with intact TTR recognized all TTR species present in the TTR and pH4-TTR samples, including tetrameric TTR species. Thus unlike the mis-TTR mAbs, these control mAbs bind TTR but with no conformational specificity. The Sigma polyclonal antibody behaved similarly to the 7G7 and 8C3 control mAbs.

TTR and pH4-TTR were also run on a native gel to see if the four mis-TTR mAbs were capable of showing conformation specificity under non-denaturing gel conditions. On a stained native PAGE gel, TTR ran as an ~35 kDa native dimer with a small amount of tetramer. In contrast, pH4-TTR ran primarily as a high molecular-weight smear with a trace amount of the ~35 kDa dimer. The non-specific Sigma polyclonal antibody recognized all TTR species present in both the TTR and the pH4-TTR sample. In contrast, 9D5 only recognized the high molecular weight TTR species present in the pH4-TTR sample. As observed in the SDS-PAGE/Western study, 9D5 did not recognize any of the native TTR species.

All four mis-TTR mAbs were subsequently analyzed by native-PAGE/Western blot. As expected and similar to 9D5, the other mis-TTR mAbs, 14G8, 6C1, and 5A1, specifically bound to the high molecular weight non-native forms of TTR present in the pH4-TTR sample. None of these antibodies recognized the ~35 kDa native TTR dimer. These results indicate that the four mis-TTR mAbs behave similarly and recognize only non-native TTR species that are conformationally distinct from native TTR.

Example 4. Inhibition of TTR Fiber Formation by Mis-TTR Antibodies

TTR-Y78F is a TTR variant containing a point mutation at position 78 in the protein sequence that destabilizes the TTR tetramer. With time and under mildly acidic conditions, this TTR variant dissociates into its monomeric subunits which can then go on to aggregate and form fibers capable of binding to thioflavin-T. The extent of fiber formation can thus be monitored by measuring thioflavin-T fluorescence at 480 nm. Introduction of a mis-TTR antibody specific for dissociated TTR monomers or aggregates would prevent the assembly of TTR fibers resulting in a decrease in thioflavin-T fluorescence relative to a no-antibody control reaction. Protocols for examining inhibition of TTR fiber formation are described elsewhere in the Materials and Methods (k).

Figure 4A:
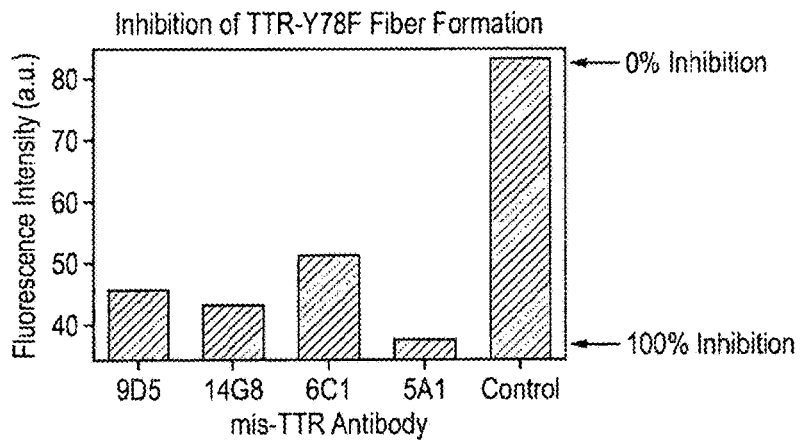
FIGS. 4A, 4B & 4C.

All four mis-TTR antibodies strongly inhibited the formation of thioflavin-T reactive TTR-Y78F fibers relative to the isotype control (the results are shown in FIG. 4 and are presented in arbitrary units (a.u.) on the y-axis). Mis-TTR antibody 5A1 almost completely inhibited fiber formation.

These results are consistent with the notion that mis-TTR antibodies bind monomeric and/or aggregated forms of TTR, thereby preventing the formation of TTR fibers.

Table 4 summarizes the characterization data obtained for the set of 4 mis-TTR antibodies (9D5, 14G8, 6C1, and 5A1) that showed good conformational selectivity for non-native forms of TTR. These antibodies had affinities ($K_D$) for pH4-TTR ranging from 14.5 nM (6C1) to 257 nM (9D5) and $B_{max}$ values ranging from 0.65 a.u. (14G8) to 2.02 (9D5). None of these antibodies recognized native TTR, but did bind to pH4-TTR on an SDS-PAGE/Western and to the high molecular weight TTR aggregates on a native-PAGE/Western. These antibodies also inhibited the formation of TTR fibrils in the fibril formation assay using Thio-T as the read-out.

TABLE 4 mis-TTR-Y78F mAb Characterization Summary Table

| Clone ID | Sandwich ELISA (pH 4-TTR) | | Western Blot | | |
|---|---|---|---|---|---|
| | $K_D$ (nM) | $B_{max}$ (OD$_{450}$ a.u.) | SDS-PAGE (TTR) | (pH 4-TTR) | Native (HMW-TTR) | % Inh. Fibrils (Thio-T) |
| 9D5 | 257 | 2.02 | – | +++ | +++ | 83 |
| 14G8 | 98.7 | 0.65 | – | +++ | ++ | 65 |
| 6C1 | 14.6 | 1.07 | – | +++ | +++ | 72 |
| 5A1 | 21.3 | 1.61 | – | +++ | +++ | 100 |

Figure 4B:
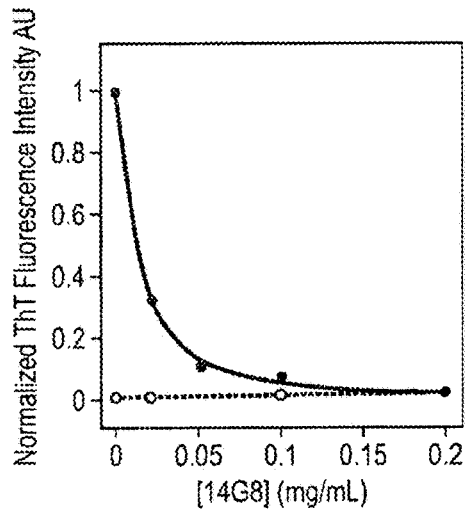
Figure 4C:
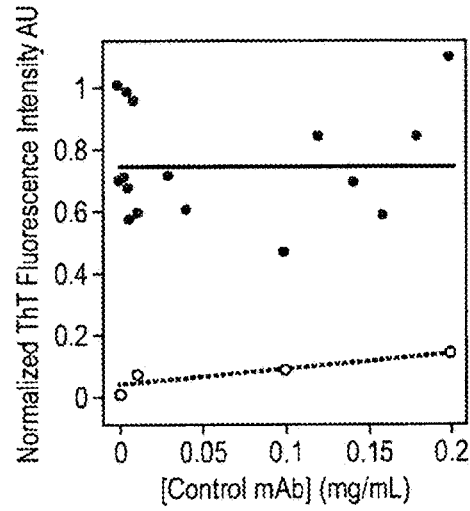

TTR-V122I is a TTR variant containing a single point mutation at position 122 that destabilizes the tetramer. Fibril formation was associated with an increase in ThT fluorescence Increasing 14G8 mAb concentrations caused a monotonic decrease in ThT fluorescence indicating a substoichiometric inhibition of TTR fibrillation ($IC_{50}=0.028\pm0.009$ mg/mL; n=3; FIG. 4B and Table 4a). The isotype control mAb did not cause inhibition of TTR fibrillation (FIG. 4C), thus demonstrating the specificity of 14G8 mediated inhibition.

Comparable substoichiometric $IC_{50}$ values determined for 5A1 and 6C1 (Table 4a) suggested analogous mechanisms of fibril inhibition for each of these mis-TTR mAbs. In contrast, 9D5 unexpectedly failed to inhibit TTR-V122I fibril formation, despite showing similar specificity and affinity for non-native TTR. It remains to be explored whether 9D5 is more sensitive to the assay conditions used.

TABLE 4a mis-TTR-V122I mAb Characterization Summary Table

| Antibody | $IC_{50} \pm SD$ (mg/mL) |
|---|---|
| 9D5 | No inhibition |
| 14G8 | 0.028 ± 0.009 |
| 6C1 | 0.048 ± 0.059 |
| 5A1 | 0.015 ± 0.02 |
| EG 27/1 | No inhibition |

Example 5. Immunohistochemical (IHC) Characterization of ATTR Tissue Using Mis-TTR mAbs The lead mis-TTR mAbs raised to the TTR 89-97 fragment of the transthyretin protein were immunohistochemically tested on fresh frozen and paraffin processed tissue from confirmed TTR cardiac amyloidosis patients. Protocols for obtaining and preparing cardiac tissue samples, immunohistochemistry (IHC), and image analysis, are provided elsewhere in the Materials and Methods (l-o). The antibodies used for IHC are described in Table 5.

TABLE 5

Antibodies Used for Immunohistochemical Characterization

| Antibody | Antibody Type | Vendor | Stain Cardiac Tissue | Concentration |
|---|---|---|---|---|
| 14G8 | mis-TTR | Prothena Biosciences | Yes | 0.5 µg/mL |
| 9D5 | mis-TTR | Prothena Biosciences | Yes | 0.5 µg/mL |
| 6C1 | mis-TTR | Prothena Biosciences | Yes | 0.5 µg/mL |
| 5A1 | mis-TTR | Prothena Biosciences | Yes | 0.5 µg/mL |
| 7G7 | TTR | Prothena Biosciences | Yes | 0.5 µg/mL |
| 6F10 | Isotype Control | Prothena Biosciences | No | 0.5 µg/mL |
| Prealbumin (A0002) | TTR | Dako North America | Yes | 1:2,000 & 1:20,000 |
| Kappa Light Chains (A0191) | LC-κ | Dako North America | No | 1:8,000 |
| Lambda Light Chains (A0193) | LC-λ | Dako North America | No | 1:8,000 |
| Amyloid A (M0759) | AA | Dako North America | No | 1:8,000 |

Cardiac tissue samples were obtained from patients with confirmed diagnoses of ATTR mutations. Demographics for cases examined immunohistochemically were as follows and are summarized in Table 6: FAC=familial amyloidotic cardiomyopathy; FAP=familial amyloidotic polyneuropathy; 1° AL=light-chain amyloidosis; ATTR=transthyretin-mediated amyloidosis; Unk=Unknown

TABLE 6

Immunohistochemical Staining of Cardiac Tissue Samples with mis-TTR Antibodies

| Case | Diagnosis | TTR Mutations | Format | Stained with TTR Antibodies? |
|---|---|---|---|---|
| Patient 1 | FAC | Ileu122 | Frozen | Yes |
| Patient 2 | FAP | Wild type | Frozen | Yes |
| Patient 3 | FAP | 84Ser | Frozen | Yes |
| Patient 4 | FAP | 84Ser | Frozen | Yes |
| Patient 5 | 1° AL | — | Frozen | No |
| Patient 6 | 1° AL | — | Frozen | No |
| Patient 7 | ATTR | 10Arg | Frozen | Yes |
| Patient 8 | ATTR | V122I | Frozen | Yes |
| Patient H1 | ATTR | Val122Ile | FFPE | Yes |
| Patient H2 | ATTR | Thr60Ala | FFPE | Yes |
| Patient H3 | ATTR | Thr49Ala | FFPE | Yes |
| Patient H4 | ATTR | Ile84Ser | FFPE | Yes |
| Patient H5 | Unk. | Senile Cardiac | FFPE | Yes |
| Patient H6 | ATTR | Ile84Ser | FFPE | Yes |

Mouse monoclonal antibodies (mis-TTR mAbs) raised to the 89-97 fragment of the transthyretin protein were immunohistochemically tested on fresh frozen and paraffin processed tissue from confirmed TTR cardiac amyloidosis patients. Each mis-TTR antibody showed immunoreactivity on ATTR cardiac tissue. Dark staining was observed in deposits throughout the myocardium and the vasculature.

When immunoreactivity was compared to staining with Congo Red of Thioflavin-T, the majority of the immunoreactivity in the tissue showed high congruence with Congo red birefringence and Thioflavin T-positive staining. This confirms the beta pleated sheet nature of the TTR amyloid deposited in this tissue. These mis-TTR antibodies also detected pre-amyloid TTR, which were localized to areas of the myocardium that were TTR-immunopositive but Congo red or Thioflavin T-negative. Both the IgG-isotype control antibody and primary antibody omission sections were negative for staining across all tissues tested. Antibodies reactive toward other amyloidogenic proteins (lambda and kappa light chains or amyloid A) were non-reactive toward the ATTR cardiac tissue used in this analysis, indicating that deposits were specifically TTR in nature.

The staining pattern of mis-TTR antibodies were compared to that obtained with a well characterized commercial TTR reference antibody (prealbumin, A0002; Dako; Carpinteria, Calif.). The DAKO reference antibody stained the diseased myocardium in the same areas as the mis-TTR antibodies, but produced a more diffuse staining pattern. The DAKO reference antibody did not stain the congophillic TTR amyloid deposits present on the vasculature as strongly as the mis-TTR antibodies.

The mis-TTR antibodies did not stain normal, non-disease tissue. Furthermore, as expected, staining with an isotype control antibody, 6F10 was also negative.

To determine if the reactivity of mis-TTR antibodies was specific for TTR deposits, cross reactivity of these antibodies toward cardiac tissue derived from patients diagnosed with primary AL amyloidosis was examined. As expected, no staining of AL amyloid tissue was observed, confirming that TTR antibodies react specifically toward ATTR diseased tissue.

Cardiac tissue from patients with confirmed diagnoses of senile systemic amyloidosis or from patients with confirmed FAC, or FAP caused by point mutations in the TTR gene also stained positively with 14G8, 9D5, 6C1, and 5A1. These results indicate that mis-TTR antibodies have the ability to recognize TTR deposits in cardiac tissue regardless of the ATTR genotype.

Other non-cardiac tissues known to express TTR were also examined for staining by 14G8, 9D5, 6C1, and 5A1 and compared to the staining obtained using the DAKO reference antibody. As expected, the liver, pancreas and choroid plexus all stained positively for TTR using the Dako reference antibody. In contrast, mis-TTR antibodies only stained the pancreatic alpha cells located in the islets of Langerhans and the choroid plexus, suggesting that some of the TTR localized to these organs are conformationally distinct from TTR expressed in the liver. The lack of mis-TTR mAb immunoreactivity in the liver suggests that the large amount of TTR expressed there is primarily tetrameric, native TTR and does not have the exposed mis-TTR epitope.

Example 6. Analysis of ATTR Vs Normal Human Plasma by SDS-PAGE/Western Blot and by Meso Scale Discovery (MSD) Plate Assay Six plasma samples from patients confirmed for V30M ATTR (Sample #11, #12, #15, #18, #19, #20) and 6 samples (#21, #22, #23, #24, #25, #27) from normal subjects were obtained from M. Saraiva (Porto University, Portugal). Sample #C6 was a normal human serum sample obtained from a commercial source (BioreclamationIVT). Samples were analyzed by SDS-PAGE and Western blot, or by MesoScale Discovery (MSD) Plate Assay. Protocols for these assays are described elsewhere in the Materials and Methods (p-r). A standard curve was generated for the MSD Plate Assay using 6C1.

In the resulting Western blots using either the 9D5 or 5A1 mis-TTR mAb, differences between normal and TTR-V30M diseased plasma samples were evident. All plasma samples contained an ~14 kDa TTR band that co-migrated with the non-native TTR monomer present in the pH4-TTR reference sample. In general, plasma samples derived from TTR-V30M patients (#21, 22, 23, 24, 25, & 27) had more of this mis-TTR species. In addition, plasma samples derived from V30M patients also contained an ~30 kDa band that co-migrates with the non-native TTR dimer present in the reference sample. With the exception of samples #12 and #18, plasma samples derived from normal individuals possessed less of this dimer species.

Figure 5A:
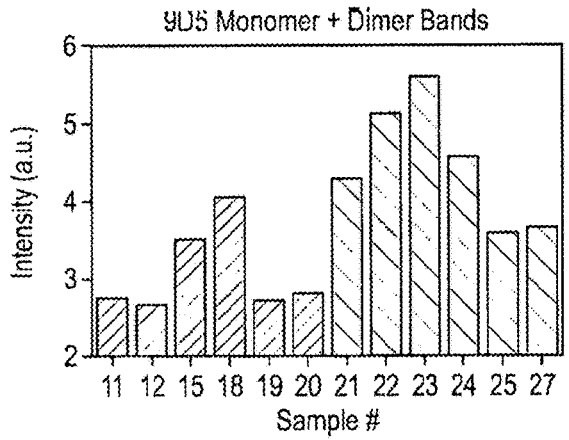
FIGS. 5A & 5B.
Figure 5B:
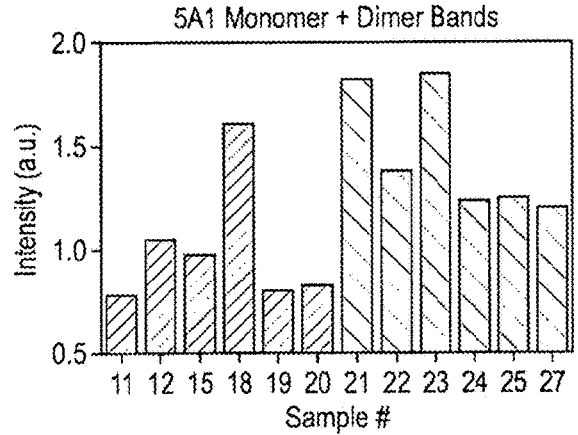

The resulting Western blots were scanned and the intensities of the combined 9D5- or 5A1-reactive TTR dimer and monomer bands were plotted for each sample (the results are shown in FIGS. 5A (9D5) and 5B (5A1) and are presented in arbitrary units (a.u.) on the y-axis). With the exception of plasma samples #15 and #18, plasma samples derived from normal individuals (11, 12, 19, and 20) contained less 9D5 reactive dimer and monomer than samples derived from V30M patients (21-25 and 27).

Figure 6:
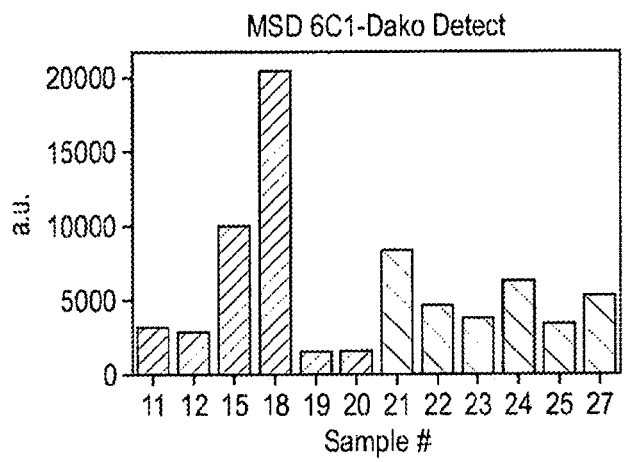
FIG. 6 depicts a MesoScale Discovery (MSD) plate assay of plasma samples from patients confirmed for V30M ATTR (Sample #11, #12, #15, #18, #19, #20) and samples from normal subjects (#21, #22, #23, #24, #25, #27) using the 6C1 antibody.
Figure 7A:
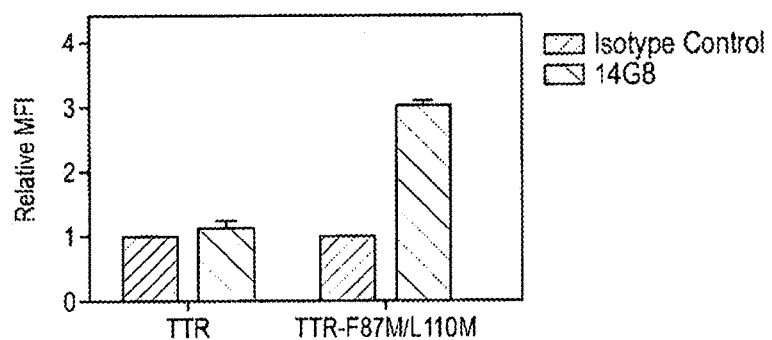
FIGS. 7A & 7B.
Figure 7B:
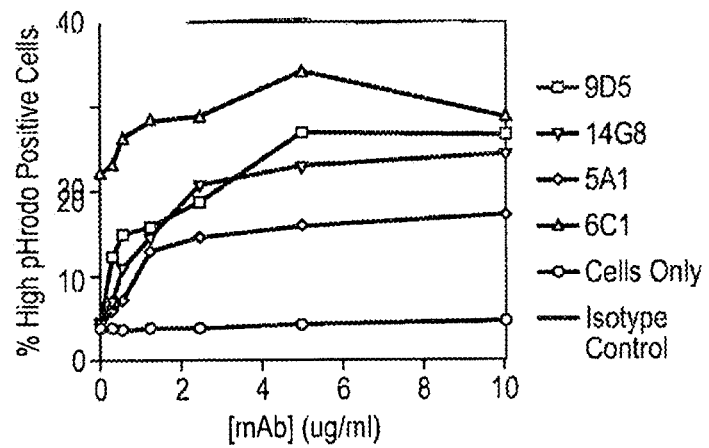

The 12 serum samples analyzed by 9D5 and 5A1 Western blot were also analyzed by MSD plate assay using 6C1 as the mis-TTR capture antibody and the Dako-SulfoTag antibody as the detection antibody. Results of these MSD assays are shown in FIG. 6 and are presented in arbitrary units (a.u.) on the y-axis. Samples 11, 12, 15, 18, 19, and 20 represent normal plasma. Samples 21-25 and 27 represent V30M diseased plasma.

With the exception of plasma samples #15 and #18, the amount of 6C1-reactive TTR present in plasma samples derived from normal individuals was lower than that observed in plasma from TTR-V30M diseased individuals. The levels of 6C1 reactivity measured by MSD assay correlated very well with the amount of 9D5 reactive dimer and monomer observed above by SDS-PAGE/Western.

In order to determine the concentration of the reactive TTR species present in plasma samples, the same samples were re-assayed using 6C1 as the capture antibody and 8C3-SulfoTag as the detection antibody. MSD signals were converted to ng/ml concentrations of reactive TTR species using the TTR F87M/L110M standard curve generated above. Based on this analysis, the average concentration of 6C1-reactive TTR present in the control samples was 271+/− 185 ng/ml. In contrast, the average concentration of reactive TTR present in the V30M diseased plasma samples was higher, at 331+/−95 ng/ml. Taken together, these MSD results suggest that mis-TTR antibodies are capable of distinguishing between ATTR disease versus normal plasma. This warrants further development of mis-TTR antibodies for use in diagnostic assays of ATTR disease.

Example 7. Design of Humanized 6C1 Antibodies

The starting point or donor antibody for humanization was the mouse antibody 6C1. The heavy chain variable amino acid sequence of mature m6C1 is provided as SEQ ID NO:1. The light chain variable amino acid sequence of mature m6C1 is provided as SEQ ID NO:13. The heavy chain CDR1, CDR2, and CDR3 amino acid sequences are provided as SEQ ID NOS:10-12, respectively. The light chain CDR1, CDR2, and CDR3 amino acid sequences are provided as SEQ ID NOS:18-20, respectively. Kabat numbering is used throughout in this Example.

The variable kappa (Vk) of m6C1 belongs to mouse Kabat subgroup 2, which corresponds to human Kabat subgroup 2. The variable heavy (Vh) of m6C1 belongs to mouse Kabat subgroup 3d, which corresponds to Kabat subgroup 3. See Kabat et al. Sequences of Proteins of Immunological Interest, Fifth Edition. NIH Publication No. 91-3242, 1991. The 16-residue CDR-L1 belongs to canonical class 4, the 7-residue CDR-L2 belongs to canonical class 1, and the 9-residue CDR-L3 belongs to canonical class 1 in Vk. See Martin & Thornton, J. Mol. Biol. 263:800-15, 1996. The 10-residue CDR-H1 (a composite of Chothia and Kabat CDR-H1, residues 26-35 as shown in FIGS. 12A-12D) belongs to canonical class 1, and the 17-residue CDR-H2 belongs to canonical class 1. See Martin & Thornton, J Mol. Biol. 263:800-15, 1996. The CDR-H3 has no canonical classes.

The residues at the interface between the Vk and Vh domains are the ones commonly found.

A search was made over the protein sequences in the PDB database (Deshpande et al., Nucleic Acids Res. 33: D233-7, 2005) to find structures which would provide a rough structural model of 6C1. The crystal structure of antibody fab (pdb code 3EYS) (Gardberg et al., Biochemistry (2009) Vol. 48(23), pp. 5210-5217) was used for Vk structure since it had good resolution (1.95 A), overall sequence similarity to 6C1 Vk, and retained the same canonical structure for the loops as 6C1. A dimeric antibody (pdb code 2OTU) (Li et al., Submission to GenBank (2007)) was used for the Vh structure since it had good similarity and resolution (1.68 A) and contained the same canonical structures for CDR-H1 and CDR-H2 as that of 6C1 VH. BioLuminate software (licensed from Schrodinger Inc.) was used to model a rough structure of 6C1.

A search of the non-redundant protein sequence database from NCBI allowed selection of suitable human frameworks into which to graft the murine CDRs. For Vh, human Ig heavy chain ADX65650 (GI: 323432015) (SEQ ID NO:3) was chosen (Scheel et al., Submission to GenBank (2010)). It shares the canonical forms of 6C1. For Vk, a human kappa light chain with NCBI accession code ABI74084 (GI: 114385652) was chosen (SEQ ID NO:15) (Shriner et al. Submission to GenBank (2006)). It has the same canonical classes for CDR-L1 and L2 as that for the parental Vk.

Six humanized heavy chain variable region variants and two humanized light chain variable region variants were constructed containing different permutations of substitutions (Hu6C1VHv1, Hu6C1VHv1b, Hu6C1VHv2, Hu6C1VHv2b, Hu6C1VHv3, and Hu6C1VHv3b (SEQ ID NOS:4-9, respectively) and Hu6C1VLv1-2 (SEQ ID NOS: 16 and 17, respectively)) (FIGS. 12A-12D and FIGS. 13A-13D). The exemplary humanized Vh and Vk designs, with backmutations and other mutations based on selected human frameworks, are shown in FIGS. 12A-12D and FIGS. 13A-13, respectively. The gray-shaded areas in the first column in FIGS. 12A-12D and FIGS. 13A-13D indicate the CDRs as defined by Chothia, and the gray-shaded areas in the remaining columns in FIGS. 12A-12D and FIGS. 13A-13D indicate the CDRs as defined by Kabat. SEQ ID NOS:4-9, 16, and 17 contain backmutations and other mutations as shown in Table 7. The amino acids at positions L2, L45, H19, H44, H49, H76, H77, H82(a), H83, and H89 in Hu6C1VHv1, Hu6C1VHv1b, Hu6C1VHv2, Hu6C1VHv2b, Hu6C1VHv3, and Hu6C1VHv3b, and in Hu6C1VLv1-2, are listed in Table 8.

TABLE 7

$V_H$, $V_L$ Backmutations and Other Mutations

| $V_H$ or $V_L$ Variant | $V_H$ or $V_L$ Exon Acceptor Sequence | Donor Framework Residues |
|---|---|---|
| Hu6C1VHv1 (SEQ ID NO: 4) | NCBI accession code ADX65650 (SEQ ID NO: 3) | H77 |
| Hu6C1VHv1b (SEQ ID NO: 5) | NCBI accession code ADX65650 (SEQ ID NO: 3) | H49, H77 |
| Hu6C1VHv2 (SEQ ID NO: 6) | NCBI accession code ADX65650 (SEQ ID NO: 3) | H76, H77, H82(a) |
| Hu6C1VHv2b (SEQ ID NO: 7) | NCBI accession code ADX65650 (SEQ ID NO: 3) | H49, H76, H77, H82(a) |
| Hu6C1VHv3 (SEQ ID NO: 8) | NCBI accession code ADX65650 (SEQ ID NO: 3) | H19, H44, H77, H83, H89 |
| Hu6C1VHv3b (SEQ ID NO: 9) | NCBI accession code ADX65650 (SEQ ID NO: 3) | H19, H44, H49, H77, H83, H89 |
| Hu6C1VLv1 (SEQ ID NO: 16) | NCBI accession code ABI74084 (SEQ ID NO: 15) | L2, L45 |
| Hu6C1VLv2 (SEQ ID NO: 17) | NCBI accession code ABI74084 (SEQ ID NO: 15) | L45 |

TABLE 8

Kabat Numbering of Framework Residues for Backmutations and Other Mutations in Humanized 6C1 Antibodies

| Residue | ADX65650 Heavy Chain | ABI74084 Light Chain | Mouse 6C1 | Hu6C1 VHv1 | Hu6C1 VHv1b | Hu6C1 VHv2 | Hu6C1 VHv2b | Hu6C1 VHv3 | Hu6C1 VHv3b | Hu6C1 VLv1 | Hu6C1 VLv2 |
|---|---|---|---|---|---|---|---|---|---|---|---|
| L2  | —  | I  | V  | —  | —  | —  | —  | —  | —  | V  | I  |
| L45 | —  | Q  | K  | —  | —  | —  | —  | —  | —  | K  | K  |
| H19 | R  | —  | K  | R  | R  | R  | R  | K  | K  | —  | —  |
| H44 | G  | —  | R  | G  | G  | G  | G  | R  | R  | —  | —  |
| H49 | S  | —  | A  | S  | A  | S  | A  | S  | A  | —  | —  |
| H76 | N  | —  | N  | N  | N  | S  | S  | N  | N  | —  | —  |

TABLE 8-continued

Kabat Numbering of Framework Residues
for Backmutations and Other Mutations in Humanized 6C1
Antibodies

| Residue | ADX65650 Heavy Chain | ABI74084 Light Chain | Mouse 6C1 | Hu6C1 VHv1 | Hu6C1 VHv1b | Hu6C1 VHv2 | Hu6C1 VHv2b | Hu6C1 VHv3 | Hu6C1 VHv3b | Hu6C1 VLv1 | Hu6C1 VLv2 |
|---|---|---|---|---|---|---|---|---|---|---|---|
| H77 | S | — | T | T | T | T | T | T | T | — | — |
| H82(a) | N | — | S | N | N | S | S | N | N | — | — |
| H83 | R | — | K | R | R | R | R | K | K | — | — |
| H89 | V | — | M | V | V | V | V | M | M | — | — |

An alignment of the murine 6C1 Vh sequence (SEQ ID NO:1) with the mouse model sequence (2 OUT_B.pro; SEQ ID NO:2), the human acceptor sequence (ADX65650; SEQ ID NO:3), and the Hu6C1VHv1, Hu6C1VHv1b, Hu6C1VHv2, Hu6C1VHv2b, Hu6C1VHv3, and Hu6C1VHv3b sequences (SEQ ID NOS:4-9, respectively), is shown in FIG. 1. The CDR regions as defined by Kabat are shaded. Positions at which canonical, vernier, or interface residues differ between mouse and human acceptor sequences are candidates for substitution. Examples of vernier/CDR foundation residues include Kabat residues 2, 49, 69, 71, 75, 78, and 94 in FIGS. 12A-12D. Examples of canonical/CDR interacting residues include Kabat residues 24, 48, and 73 in FIGS. 12A-12D. Examples of interface/packing (VH+VL) residues include Kabat residues 37, 39, 45, 47, 91, 93, and 103 in FIGS. 12A-12D.

An alignment of the murine 6C1 Vk sequence (SEQ ID NO:13) with the mouse model sequence (3EYS_L_St.pro; SEQ ID NO:14), the human acceptor sequence (ABI74084; SEQ ID NO:15), and the Hu6C1VLv1 and Hu6C1VLv2 sequences (SEQ ID NOS:16 and 17, respectively), is shown in FIG. 2. The CDR regions as defined by Kabat are shaded. Positions at which canonical, vernier, or interface residues differ between mouse and human acceptor sequences are candidates for substitution. Examples of vernier/CDR foundation residues include Kabat residues 4, 35, 46, 49, 66, 68, and 69 in FIGS. 13A-13D. Examples of canonical/CDR interacting residues include Kabat residues 2, 48, 64, and 71 in Table 8. Examples of interface/packing (VH+VL) residues include Kabat residues 36, 38, 44, 87, and 98 in FIGS. 13A-13D.

The rationales for selection of the positions indicated in Tables 7 and 8 in the light chain variable region as candidates for substitution are as follows.

I2V: This is a canonical CDR interacting residue. The bulkier side chain of Ile could potentially interfere with CDRs L1 and L2 packing. This residue is backmutated to Val in Hu6C1VH1.

Q45K: Lys is more frequent at this position than Gln in the human sequence; therefore this is a frequency based backmutation.

The rationales for selection of the positions indicated in Tables 9 and 10 in the heavy chain variable region as candidates for substitution are as follows.

R19K: Lys forms H-bonds with adjoining residues whereas Arg does not.

G44R: Arg forms H-bonds with interface residue Phe98 in the light chain, whereas Gly does not.

S49A: Ser can potentially form an H-bond with Hys in CDR-H2.

N76S: There is a high deamidation exposure at this residue. Ser is second most frequent in human germline at this position.

S77T: Serine at this position is very rare in the human germane heavy chain frameworks, whereas, Threonine is most frequent at position 77. This back mutation has been made to mitigate any immunogenecity potential.

N82(a)S: There is a high deamidation exposure at this residue. Ser is second most frequent in human germline at this position.

R83K: Lys at this position forms multiple interactions with adjoining residues, seeming to exert a stabilizing effect on the loop, whereas Arg does not.

V89M: Met forms H-bonds with interference residue Tyr91 and appears to stabilize the interface, whereas Val does not interact with Tyr91.

The two humanized light chain variable region variants and two humanized heavy chain variable region variants are as follows:

Hu6C1VL version 1 (I2V and Q45K backmutations in lowercase):
(SEQ ID NO: 16)
DvVMTQTPLSLPVTPGEPASISCRSSQSIVHSNGNTYLEWYLQKPGQSPk
WYKVSKRFSGVPDRFSGSGSGTDFTLKISRVEAEDVGVYYCFQGSHVPLT
FGGGTKVEIK Hu6C1VL version 2 (Q45K backmutation in lowercase):
(SEQ ID NO: 17)
DIVMTQTPLSLPVTPGEPASISCRSSQSIVHSNGNTYLEWYLQKPGQSPk
WYKVSKRFSGVPDRFSGSGSGTDFTLKISRVEAEDVGVYYCFQGSHVPLT
FGGGTKVEIK Hu6C1VH version 1 (S77T backmutation in lowercase):
(SEQ ID NO: 4)
EVQLVESGGGLVQPGGSLRLSCAASGFTFSNYYMSWVRQAPGKGLEWVSY
ISIDGNNIYHPDSVKGRFTISRDNAKNtLYLQMNSLRAEDTAVYYCARDS
DYGYFDVWGQGTLVTVS Hu6C1VH version 1b (S49A and S77T backmutations in lowercase):
(SEQ ID NO: 5)
EVQLVESGGGLVQPGGSLRLSCAASGFTFSNYYMSWVRQAPGKGLEWVaY
ISIDGNNIYHPDSVKGRFTISRDNAKNtLYLQMNSLRAEDTAVYYCARDS
DYGYFDVWGQGTLVTVSS Hu6C1VH version 2 (N76S, S77T, and N82(a)S backmutations in lowercase):
(SEQ ID NO: 6)
EVQLVESGGGLVQPGGSLRLSCAASGFTFSNYYMSWVRQAPGKGLEWVSY
ISIDGNNIYHPDSVKGRFTISRDNAKstLYLQMsSLRAEDTAVYYCARDS
DYGYFDVWGQGTLVTVSS -continued Hu6C1VH version 2b (S49A, N765, S77T, and N82(a)S backmutations in lowercase):
(SEQ ID NO: 7)
EVQLVESGGGLVQPGGSLRLSCAASGFTFSNYYMSWVRQAPGKGLEWVaY
ISIDGNNIYHPDSVKGRFTISRDNAKstLYLQMsSLRAEDTAVYYCARDS
DYGYFDVWGQGTLVTVSS Hu6C1VH version 3 (R19K, G44R, S77T, R83K, and V89M backmutations in lowercase):
(SEQ ID NO: 8)
EVQLVESGGGLVQPGGSLkLSCAASGFTFSNYYMSWVRQAPGKrLEWVSY
ISIDGNNIYHPDSVKGRFTISRDNAKNtLYLQMNSLkAEDTAmYYCARDS
DYGYFDVWGQGTLVTVSS Hu6C1VH version 3b (R19K, G44R, S49A, S77T, R83K, and V89M backmutations in lowercase):
(SEQ ID NO: 9)
EVQLVESGGGLVQPGGSLkLSCAASGFTFSNYYMSWVRQAPGKrLEWVaY
ISIDGNNIYHPDSVKGRFTISRDNAKNtLYLQMNSLkAEDTAmYYCARDS
DYGYFDVWGQGTLVTVSS Example 8. Binding Kinetic Analysis of Humanized 6C1 Antibodies Binding kinetics of humanized 6C1 antibodies comprising a heavy chain selected from version 3b and a light chain selected from version 2 were characterized by Biacore and shown below.

| mAb | $k_a$(1/Ms) | $k_d$(1/s) | $K_D$(M) | $R_{max}$ |
|---|---|---|---|---|
| Hu-6C1-H3bL2 | 3.724E+5 | 5.449E−4 | 1.463E−9 | 38.80 |

Example 9. Materials and Methods a. Antibody Generation Protocol

Mice were immunized weekly with the antigenic peptides TTR-MAP, TTR89-97-N-KLH or TTR89-97-C-KLH in RIBI adjuvant or monthly in TiterMax adjuvant. Three to four days prior to fusion, selected mice were given a final IV boost with immunogen in saline solution. Spleen were homogenized to prepare splenocytes and fused with SP2/0 myeloma cells using a standard electrofusion protocol. Fused cells in selection media were plated in 96-well plates and screened after 7-10 days.

b. Antibody Screening Protocol

Hybridoma selection was based on the following ELISA screen: 96-well ELISA plates were coated with chicken anti-His, 1 µg/mL PBS and incubated for 1 hour. Plates were blocked with of 1% BSA/PBS solution, 200 uL/well for 15 minutes then 0.5 µg/mL pH4-TTR, 50 µL/well was added and incubated for 1 hour. pH4-TTR is TTR that has been subjected to low pH (50 mM sodium acetate, pH 4.0) in order to dissociate/aggregate TTR, exposing the TTR89-97 epitope. Plates were washed twice with TBS-T. Supernatant from fusion plates was added, 50 µL/well and incubated for 1 hour. Plates were washed twice with TBS-T. The detection antibody, goat anti-mouse (IgG1, 2a, 2b, 3 specific)-HRP diluted 1:5,000 in 0.5% BSA/PBS/TBS-T, 50 µL/well was added and incubated for 1 hour. Finally, plates were washed five times with TBS-T and TMB substrate, 100 µL/well was added. After 15 minutes, substrate development was stopped with 2N Sulfuric Acid, 50 µL/well. Plates were read at 450 nm. Wells with an O.D.>1.0 were selected and cells were transferred to a 24-well plate. After 3 days of growth, clones were counter screened with the above assay to confirm binding, and substituting native TTR for pH4-TTR as a negative counter screen, allowing for selection of clones producing TTR mAbs specific for non-native forms of TTR.

c. Antibody Expression Protocols

CMV driven light chain and heavy chain plasmids carrying humanized monoclonal antibody sequences were transfected into CHO-S1 cells (Life Technology). Dual selection was applied to make a selected pool. Conditioned media was assayed for titer, binding and analyzed by SDS-PAGE/Western blotting. Selected pools were used for clone generation using Clonepix system (Molecular Devices). Clones were ranked based on antibody titer. Selected clones were expanded and banked.

The highest producing clone was expanded in shake flasks and the culture was used to inoculate 10-25 L Wave bag cultures. A mixture of FreeStyle-CHO, CD OptiCHO and FreeStyle F17 expression media supplemented with Glutamax (media and Glutamax from Life Technology) was used for shake flask as well as for Wave bag cultures. Batch culture was made using a Wave Bioreactor (GE Heathcare) at 37° C., 7% $CO_2$ under constant agitation. Samples were drawn periodically to monitor cell number, viability and antibody production. Supplementation with Cell Boost (Hy-Clone) was made if needed. The batch culture was harvested when cell viability starts to decline below 90% (5-7 days).

d. Antibody Purification Protocol

The cell culture was harvested after first allowing the cells in suspension to settle down to the bottom of the Wave bag via gravity at 4° C. Harvested media was clarified through a depth filter (Millistak Pod COHC, Millipore), concentrated 10-fold by tangential flow filtration (Pelicon 2PLC 30K, Millipore) and sterile filtered through a 0.2 µm filter (Opticap XL, Millipore). The concentrated conditioned media was then loaded onto a Protein G Sepharose Fast Flow column (GE Lifesciences) pre-equilibrated in 1×PBS, pH 7.4 using an FPLC (Akta Avant, GE Lifesciences). Unbound proteins were washed off the column with 5-10 column volumes of 1×PBS, pH 7.4 until the $OD_{280}$ reached baseline. The bound antibody was eluted from the column with 2 column volumes of IgG Elution Buffer (Thermo Scientific). Elution fractions were collected and pH neutralized with 2M Tris, pH 9.0 (60 µL per 1 ml elution).

Antibody-containing fractions were pooled and dialyzed overnight at 4° C. against 1×PBS, pH 7.4. The dialyzed sample was then sterilized by ultrafiltration through a 0.2 µm PES filter and stored at 4° C. The final protein concentration was determined by bicinchoninic acid (BCA) using bovine gamma-globulin as the protein standard (Thermo Scientific).

e. Recombinant TTR Expression and Purification Protocols

E. coli (BL21-A1) cells were transformed with a pET21a (+) plasmid containing a TTR insert (Met-hTTR-(His)$_6$ or a TTR variant containing an F87M/L110M double mutation. Cells were grown in 2YT broth containing 100 µg/ml ampicillin. Expression of TTR was induced overnight at 20° C. in the presence of 1 mM IPTG and 005% arabinose.

The cells were collected by centrifugation at 4000×g for 10 min. and stored at −80° C. until used. 10-15 g cell pellets were thawed and lysed in 50 ml Buffer A (1×PBS containing 500 mM NaCl, 20 mM imidazole) by processing through an LV-1 high-shear processor (Microfluidics, Inc.). Lysed cells were centrifuged at 12,000×g for 15 min, filtered through a 0.2 µm PES filter prior to purification on a His-Trap HP column (GE Lifesciences). After loading, the column was washed with 10 c.v. of Buffer A and eluted with Buffer B (1×PBS with 500 mM NaCl, 500 mM imidazole). Peak fractions corresponding to TTR were collected, dialyzed against 1×PBS and stored at −80° C. until used.

f. TTR Antigen Preparation

Native TTR antigen was prepared by diluting a concentrated stock of recombinant TTR-6His to a final concentration of 2.5 µg/ml in 1×PBS. pH4-treated TTR was generated by incubating recombinant TTR at a concentration of 0.2 mg/ml in 50 mM sodium acetate, pH 3.95 for 72 hours at room temperature. Under these conditions, TTR dissociates into mixture of TTR monomers and aggregated forms that are structurally distinct from native TTR. The pH4-TTR was then diluted to a final concentration of 2.5 µg/ml in 1×PBS immediately before use in the assay. 96-well plates (Costar #3690) were coated at room temperature with 50 µl per well of 1.0 µg/ml chicken-anti-his polyclonal antibody (Abcam #Ab9107) in 1×PBS for 1 hr. The coating solution was discarded and the plate was blocked with a 250 µl/well volume of 1×BSA-containing block buffer diluted in 1×PBS (G-Biosciences #786-193) for 1 hr.

g. ELISA Protocol

Coated and blocked 96-well plates were treated with 50 µl per well of 2.5 µg/ml TTR antigen (either native TTR or pH4-TTR) for 1 hr. at room temperature. The plates were then washed two times with 250 µl per well of wash buffer (1× Tris Buffered Saline containing 0.05% Tween-20). Washed plates were then treated with 50 µl per well of the appropriate anti-TTR monoclonal antibody at concentrations ranging from of 0.31 to 2.5 µg/ml, for 1 hr.

The treated plates were washed 3 times with 250 µl per well wash buffer. After washing, the plates were treated for 1 hr. with 50 µl per well of detection antibody comprising a 1:5,000 dilution of peroxide-conjugated goat-anti-mouse (Jackson ImmunoResearch #115-035-164) in 1×PBS. The plate was then washed 3 times prior to the addition of 100 µl per well TMB substrate (Rockland). The HRP reaction was allowed to proceed at room temperature for 15 min. before quenching with a 50 µl per well volume of 1N $H_2SO_4$. Spectroscopic absorbance was measured at a wavelength of 450 nm.

h. SDS-PAGE

Electrophoresis on SDS-polyacrylamide gels was carried out as follows. 0.1-1 µg TTR or pH 4.0-TTR in 1×LDS sample buffer (Life Technologies) was loaded onto a 10% NuPAGE bis-tris gel and subjected to electrophoresis in IVIES buffer at a constant 90V for 105 minutes. After electrophoresis, the gel was either stained in Instant Blue (Expedeon) or transferred to nitrocellulose filters for Western blot analysis.

i. Native-PAGE

Electrophoresis on native Tris-glycine gels was carried out as follows. 0.1-1 µg TTR or pH 4.0-TTR in 1×Tris-glycine sample buffer (Life Technologies) was loaded onto a 10-20% Tris-glycine gel and subjected to electrophoresis in 1× Native Tris-glycine running buffer at a constant 120V for 105 minutes. After electrophoresis, the gel was either stained in Instant Blue (Expedeon) or transferred to nitrocellulose filters for Western blot analysis.

Western Blot

SDS- or Native-PAGE gels were blotted onto nitrocellulose filter paper (iBlot, P7 Program) and blocked with blocking buffer (Licor) for 30 minutes. The filters were then incubated in 0.5 µg/ml primary antibody in blocking buffer for 1 hour at room temperature (or over-night at 4° C.), followed by three, 10 minutes washes with 1×TBS. The filters were placed in IRDye 800CW-conjugated goat-anti-mouse secondary diluted 1:20,000 in block buffer. After incubating the filters in secondary antibody solution for 1 hour at room temperature, the filters were washed and imaged on an Odyssey CLx infrared imager (Licor).

k. TTR Fiber Formation Assay Procotol

A solution of 3.6 µM (0.2 mg/ml) TTR-Y78F in 50 mM sodium acetate, pH 4.8 was incubated at 37° C. for 72 hours in the presence of 1.4 µM (0.2 mg/ml) mis-TTR antibody or an isotype control. After incubation, a 5× molar excess of thioflavin-T was added to the mixture and allowed to bind for 30 minutes. Fluorometric measurements were measured at an emissions wavelength of 480 nm with an excitation wavelength set at 440 nm. The 0% inhibition was set as the fluorescence intensity in the presence of an isotype control antibody (83 a.u.) and the 100% inhibition point was set as the fluorescence in the absence of TTR-Y78F protein (38 a.u.).

l. Cardiac Tissue Samples

Fresh frozen and paraffin-processed blocks of cardiac tissue with confirmed diagnoses of ATTR mutations were obtained from Dr. Merrill Benson at Indiana University. Samples included eight fresh frozen samples and six FFPE samples and each sample was diagnosed with either ATTR or some other cardiac amyloidosis. The diagnosis of the tissue was further confirmed at Prothena via IHC staining with antibodies to kappa and lambda light chains and amyloid A prior to characterization with the TTR antibodies.

m. Immunohistochemistry

Immunohistochemistry was performed on lightly paraformaldheyde-fixed, 10 µm slide-mounted cryosections and on 5 µm paraffin sections. The immunoperoxidase method was the principal detection system, which was performed on the Leica Bond Rx (Leica Biosystems, Buffalo Grove, Ill.) using the Bond Polymer Refine Detection Kit (DS980, Leica Biosystems). The primary antibodies were incubated for one hour (according to concentrations in Table 2.) followed by incubation with anti-mouse and anti-rabbit polymeric HRP-linker antibody conjugates. The staining was visualized with a DAB chromogen, which produced a brown deposit. The slides were counterstained with hematoxylin, dehydrated in an ascending series of alcohols, cleared in xylenes, and coverslipped with CytoSeal 60 (Richard Allen Scientific; Kalamazoo, Mich.). Negative control consisted of performing the entire immunohistochemical procedure on adjacent sections with a non-immune IgG isotype control or an omission of the primary antibody.

n. Demonstration of Amyloid: Congo Red and Thioflavin T Staining

Congo red stain was performed to demonstrate TTR amyloid in the tissue using a kit from American MasterTech (Lodi, Calif.). The staining was performed according to the manufacturer's procedure. Slides were stained in the Congo Red solution for 1 hour followed by differentiation in 1% sodium hydroxide for approximately 15 seconds. The slides were then rinsed in running water, dehydrated through an alcohol series of increasing concentrations, and cleared through three changes of xylenes, and coverslipped with CytoSeal 60.

A modified Thioflavin T staining protocol (Schmidt et al 1995.) was employed to determine the presence of TTR amyloid in the tissue. Briefly, slides were counterstained with a Mayers hematoxylin, rinsed in running water and stained with a filtered solution of 0.015% Thioflavin T (T3516-25G; Sigma-Aldrich, St. Louis, Mo.) in 50% ethanol for ten minutes. The slides were then rinsed in running water and differentiated in 1% (v/v) acetic acid for 10 minutes and rinsed three times in water. The slides were allowed to air dry before being coverslipped with ProLong Gold (Life Technologies).

o. Image Analysis

Slides were imaged with either an Olympus BX61 microscope, Hamamatsu Nanozoomer 2.0HT digital slide scanner, or a Leica SPE spectral confocal system. Images were collected and stored as TIFF files.

p. Analysis of Human Plasma Samples by SDS-PAGE/Western

Six plasma samples from patients confirmed for V30M ATTR (Sample #11, #12, #15, #18, #19, #20) and 6 samples (#21, #22, #23, #24, #25, #27) from normal subjects were obtained from M. Saraiva (Porto University, Portugal). Sample #C6 was a normal human serum sample obtained from a commercial source (BioreclamationIVT). These plasma samples were separated by SDS-PAGE and Western blotted with 9D5 as follow. A 1.4 µl volume of plasma was diluted 1:8 into 1×LDS sample buffer in the absence of reducing agent (Life Technologies). Samples were subjected to SDS-PAGE separation and Western blotted with 0.5 µg/ml 9D5 as described previously.

q. Analysis of Human Plasma Samples by MesoScale Discovery (MSD) Plate Assay 96-well MSD plates were coated with monoclonal antibody 6C1 at a concentration of 4 µg/mL in PBS and incubated for 2 hours at room temperature with shaking, or overnight at 4° C. Plates were washed three times with 1×TBST before being blocked with of 3% MSD Blocker A solution, 150 µL per well for 1 hour shaking. A 30 µl per well volume of human plasma samples diluted 1:10 in a sample buffer comprised of 0.6% globulin-free bovine serum albumin, 1.5 mM monobasic sodium phosphate, 8 mM dibasic sodium phosphate, 145 mM sodium chloride, 0.05% Triton X-405, and 0.05% thimerosal was added to the blocked MSD plates for 1 hour. Plates were washed 3 times with 1×TBST. A 50 µl per well volume of 1 µg/ml sulfo-tagged detection antibody (either 8C3 total TTR antibody of the Dako polyclonal antibody) in sample buffer was added for 1 hr. at room temperature with shaking. Plates were washed three times with 1×TBST followed by the addition of 150 µl per well 1× Read Buffer T solution (Meso Scale Discovery). Plates were then read in the MSD Sector imager.

r. Generation of an MSD Standard Curve

In order to quantitate the amount of non-native, 6C1-reactive TTR protein present in human plasma samples, a MSD standard curve was generated using recombinant TTR-F87M/L110M as a 6C1-reactive TTR standard. This TTR variant contains two amino acid substitutions that prevent tetramer formation and keeps the protein in the monomer state (Jiang et al. (2001) *Biochemistry* 40, 11442-11452). As such, this TTR variant is recognized by all mis-TTR mAbs and is therefore well-suited for use as a reference standard in the MSD assay.

To generate the standard curve, 96-well MSD plates were coated with mis-TTR antibody 6C1 at a concentration of 4 µg/mL in PBS and incubated for 2 hours at room temperature with shaking, or overnight at 4° C. Plates were washed three times with 1×TBST before being blocked with of 3% MSD Blocker A solution, 150 µL per well for 1 hour shaking. The blocked plates were then treated for 1 hour with 50 µl per well of 25 µg/mL TTR-F87M/L110M serially diluted 1:5 with the last dilution being a buffer blank. Plates were washed 3 times with 1×TBST before the addition of a 50 µl per well volume of 1 µg/ml SulfoTag-detection antibody (8C3-SulfoTag or Dako pAb-SulfoTag) for 1 hour at room temperature with shaking. Both 8C3 mAb and the Dako antibody were coupled to the SulfoTag and could be used at the detection antibody since they bound to total TTR and were not conformation specific.

After treatment with the detection antibody, plates were washed three times with a 150 µl per well volume of 1×TBST, followed by the addition of 150 µl per well 1× Read Buffer T (MSD). Plates were read in the MSD Sector imager and a resulting TTR F87M/L110M calibration curve was generated.

Example 10. Evaluation of Mis-TTR. Antibodies in Transgenic Louse Model

In vivo studies are conducted in a humanized transgenic mouse model V30M hTTR (Inoue et al., (2008) Specific pathogen free conditions prevent transthyretin amyloidosis in mouse models. Transgenic Research 17:817-826) to assess the efficacy of anti-TTR antibodies in the binding and removal of aggregated hTTR.

Transgenic mice are bred using standard procedures and their circulating hTTR levels are assessed by ELISA. Mice with a serum level of 200-400 µg/ml of hTTR are used for subsequent efficacy studies. The first set of studies examine the natural deposition of hTTR in transgenic mice. Detection of hTTR deposits begins at 12 months of age and is repeated every 3-6 months thereafter. Once an acceptable level of aggregates is seen in transgenic mice, efficacy studies are initiated. Animals are divided into three treatment groups (n=10/group) and treated weekly for four weeks with an IP dose of vehicle, control antibody (isotype control, 10 mpk) or an anti-hTRR antibody (10 mpk). One week after the last treatment the mice are euthanized, tissues collected and processed, and then stained to assess the number and size of remaining TTR deposits. Quantitative methods and statistics are employed to determine the degree of clearance seen among groups.

In an alternative approach, hTTR aggregates are prepared in vitro and then injected into the kidney of transgenic mice to seed the deposition of new aggregates. Applicant has determined that the injection of these preparations can expedite the deposition of new aggregates in a predictable manner. Based on these findings, animals are sedated, the left kidney exposed and pre-aggregated hTTR material injected into the cortex of the kidney. After a suitable recovery period, mice are divided into three treatment groups (n=10/group) and treated weekly for four-eight weeks with an IP dose of vehicle, control antibody (isotype control, 10 mpk) or an anti-hTRR antibody (10 mpk). One week after the last treatment the mice are euthanized, the kidneys collected and processed, and then stained to assess the number and size of TTR deposits. Quantitative methods and statistics are employed to determine the degree of change seen among groups.

Example 11. Evaluation of Mis-TTR Antibodies in a Matrigel Implant Model

Applicant has determined that pre-aggregated hTTR can be suspended in Matrigel (BD Bioscience, Cat #354263), allowed to solidify and then placed subcutaneously in mice. At four weeks post implantation, the Matrigel implant maintained its structure and the aggregated hTTR was still present within the implant. Moreover, the implant was well tolerated by the mice and anti-hTTR antibodies were able to penetrate and bind to the aggregates suspended in the Matrigel. Based on these findings, an antibody efficacy study is conducted. Animals are sedated and an implant containing pre-aggregated hTTR suspended in Matrigel placed subcutaneously in mice. After a suitable recovery period, mice are divided into three treatment groups (n=10/group) and treated weekly, for two-four weeks with an IP dose of vehicle, control antibody (isotype control, 10 mpk) or an anti-hTRR antibody (10 mpk). After the last treatment, the mice are euthanized, the skin containing the implant collected and processed, and then the amount of TTR deposits remaining assessed using histological and/or biochemical methods. Quantitative analysis and statistics are employed to determine the degree of clearance seen among groups.

Example 12 Electron and Atomic Force Microscopy

Figure 8A:
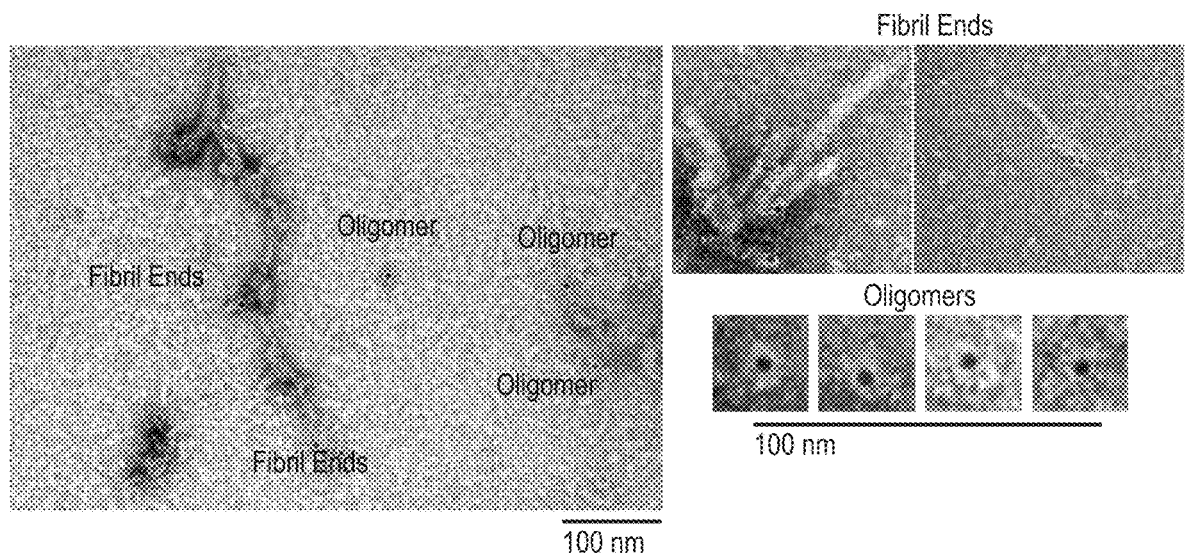
Figure 8B:
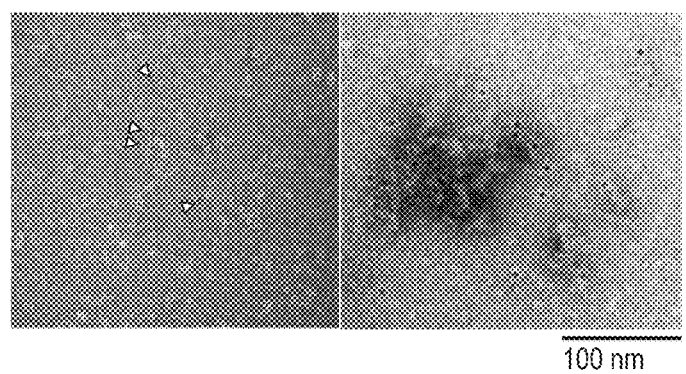
Figure 8C:
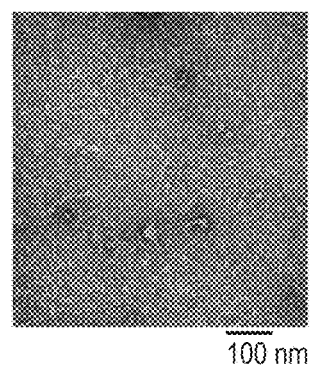
Figure 9B:
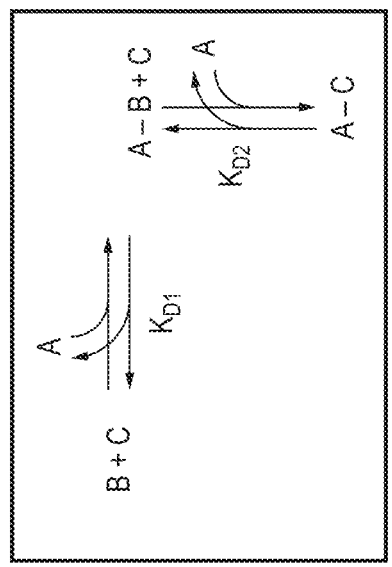
FIGS. 9A. 1-4 and 9B: Interaction of 14G8 with mature TTR-V122I fibrils assessed using ITC fits to a 2-binding site model. ITC data and binding isotherms for 14G8 binding to aggregated TTR variants are presented in FIG. 8A. Binding was fit to a 2-binding site model with KD values shown (FIG. 8B).

Immunogold transmission electron microscopy (TEM) and atomic force microscopy (AFM) were used to generate images of the interaction between mis-TTR mAbs and both aggregated and fibrillar forms of the protein. Isothermal titration calorimetry (ITC) was carried out by titrating 14G8 into a solution of aggregated TTR using standard methods. Using TEM, immunogold labeling with 14G8 was observed in TTR-V122I oligomer aggregates and fibril ends (FIG. 8A), whereas immunogold labeling with an anti-TTR pAb shows binding along the lengths of TTR fibers and to oligomeric clusters (FIG. 8B). IgG1 isotype control mAb does not show immunogold labeling (FIG. 8C). TTR-V122I fibers, alone and in the presence of 14G8±6 nm colloidal gold-conjugated secondary antibody, were assessed using AFM. Gold labeling was observed at fiber ends (FIG. 8D). FIG. 9A shows isothermal titration calorimetry (ITC) data and binding isotherms for 14G8 binding to aggregated TTR variants. FIG. 9B shows binding fitted to a 2-binding site model with KD values shown. TEM, AFM, and ITC analysis provide evidence mis-TTR mAbs bind to TTR aggregates and fibrils primarily at 2 distinct sites: oligomers and fibril ends.

Example 13: Antibody Binding to TTR Amyloid in the Peripheral Nerves and Gastrointestinal Tract of a Patient with ATTR Amyloidosis from a TTR-V30M Mutation 14G8 and control antibodies were evaluated immunohistochemically to determine their reactivity for TTR amyloid deposits in nerve, and gastrointestinal tract samples obtained from patients with confirmed diagnoses of ATTR amyloidosis from a V30M mutation. FIGS. 10A-G show 14G8 immunolabeled TTR amyloid present between fibers of the nerve fascicle (FIG. 10A panels 1 and 2), which overlapped with staining by Congo red (FIG. 10B panels 1 and 2) and thioflavin T (FIG. 10C panels 1 and 2), and immunolabeling by a total-TTR antibody (FIG. 10D) in tissue derived from a patient with ATTR amyloidosis. No staining was seen with the use of 2 isotype control antibodies (FIGS. 10E-F); however, axonal degeneration (lack of Schwann cell nuclei) in the areas laden with TTR amyloid deposits were also observed (FIGS. 10E-F [red areas in 10E]). Peripheral nerves from a healthy control were not labeled using either 14G8 or a total-TTR antibody (FIG. 10G panels 1-3)

14G8 labelled TTR amyloid deposited throughout the gastrointestinal tract; Meissner's plexus and glands in the esophagus (FIG. 11A, B panels 1), the rich vasculature bed in the submucosa (FIG. 11C panel 1), and the muscularis propria (MP) and muscularis mucosa (MM) of the jejunum (FIG. 11D panel 1) were immunolabeled with 14G8. 14G8-positive TTR amyloid overlapped with Congo red fluorescent staining (FIGS. 11A-D panels 2). ATTR amyloidosis tissue stained with an isotype control mAb (FIGS. 119A-D panels 3). 14G8 immunoreactivity was absent in healthy control tissue (FIG. 11E panels 1-4)

These findings provide evidence that mis-TTR mAbs can be useful in preventing the deposition or enhancing the clearance, or both, of TTR amyloid in patients with ATTR amyloidosis regardless of the specific organ(s) involved while sparing the function of the normal tetrameric form of the protein.

What is claimed is:

1. A method of treating a subject having or at risk of having a transthyretin-mediated amyloidosis associated with a condition selected from cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, age related macular degeneration, and a ligament or tendon disorder, the method comprising administering to the subject an effective regime of an antibody that specifically binds transthyretin comprising three heavy chain CDRs and three light chain CDRs from antibody 6C1.

2. A method of treating or delaying onset of or reducing severity of a transthyretin-mediated amyloidosis in a subject, comprising administering to the subject an effective regime of an antibody that specifically binds transthyretin comprising three heavy chain CDRs and three light chain CDRs from antibody 6C1.

3. The method of claim 2, wherein the transthyretin-mediated amyloidosis is associated with a condition selected from cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, age related macular degeneration, and a ligament or tendon disorder.

4. The method of claim 2, wherein administering the antibody delays the onset of a transthyretin-mediated amyloidosis in the subject.

5. The method of claim 2, wherein administering the antibody inhibits or reduces aggregation of transthyretin in the subject.

6. The method of claim 2, wherein administering the antibody inhibits or reduces transthyretin fibril formation in the subject.

7. The method of claim 2, wherein administering the antibody reduces transthyretin deposits in the subject.

8. The method of claim 2, wherein administering the antibody clears aggregated transthyretin in the subject relative to a subject with a transthyretin-mediated amyloidosis who has not received the antibody.

9. The method of claim 2, wherein administering the antibody stabilizes a non-toxic conformation of transthyretin in the subject.

10. The method of claim 2, wherein the antibody comprises three Kabat heavy chain CDRs designated SEQ ID NOS: 10-12, respectively and three light CDRs designated SEQ ID NOS: 18-20, respectively.

11. The method of claim 10, wherein the antibody has a human IgG1 isotype.

12. The method of claim 10, provided position H77 of the antibody is occupied by T.

13. The method of claim 12, provided position H49 of the antibody is occupied by A.

14. The method of claim 12, provided positions H76 and H82(a) of the antibody are occupied by S.

15. The method of claim 12, provided positions H19, H44, H83, and H89 of the antibody are occupied by K, R, K, and M, respectively.

16. The method of claim 10, provided position L45 of the antibody is occupied by K.

17. The method of claim 16, provided position L2 of the antibody is occupied by V.

18. The method of claim 2, wherein the antibody is a humanized or chimeric 6C1 antibody that specifically binds to transthyretin, wherein 6C1 is a mouse antibody characterized by a mature heavy chain variable region of SEQ ID NO:1 and a mature light chain variable region of SEQ ID NO:13.

19. The method of claim 2, wherein the antibody comprises a humanized mature heavy chain variable region having an amino acid sequence at least 90% identical to SEQ ID NO:9 and a humanized mature light chain variable region having an amino acid sequence at least 90% identical to SEQ ID NO:17.

20. The method of claim 19, wherein the antibody comprises a mature heavy chain variable region having an amino acid sequence at least 95% identical to SEQ ID NO:9 and a mature light chain variable region having an amino acid sequence at least 95% identical to SEQ ID NO:17.

21. The method of claim 20, wherein the antibody comprises a mature heavy chain variable region having an amino acid sequence at least 98% identical to SEQ ID NO:9 and a mature light chain variable region having an amino acid sequence at least 98% identical to SEQ ID NO:17.

22. The method of claim 18, wherein the mature heavy chain variable region of the antibody has the amino acid sequence of SEQ ID NO:4.

23. The method of claim 18, wherein the mature heavy chain variable region of the antibody has the amino acid sequence of SEQ ID NO:5.

24. The method of claim 18, wherein the mature heavy chain variable region of the antibody has the amino acid sequence of SEQ ID NO:6.

25. The method of claim 18, wherein the mature heavy chain variable region of the antibody has the amino acid sequence of SEQ ID NO:7.

26. The method of claim 18, wherein the mature heavy chain variable region of the antibody has the amino acid sequence of SEQ ID NO:8.

27. The method of claim 18, wherein the mature heavy chain variable region of the antibody has the amino acid sequence of SEQ ID NO:9.

28. The method of any one of claims 22-27, wherein the mature light chain variable region of the antibody has the amino acid sequence of SEQ ID NO:16 or SEQ ID NO:17.

29. The method of claim 2, wherein the mature heavy chain has the amino acid sequence of SEQ ID NO: 9 and the mature light chain variable region of the antibody has an amino acid sequence of SEQ ID NO:17.

30. The method of claim 2 or 21, wherein the antibody is a binding fragment.

31. The method of claim 30, wherein the binding fragment is a single-chain antibody, Fab, or Fab'2 fragment.

32. The method of claim 2 or 21, wherein the mature light chain variable region of the antibody is fused to a light chain constant region and the mature heavy chain variable region of the antibody is fused to a heavy chain constant region.

33. The method of claim 32, wherein the heavy chain constant region is a mutant form of a natural human heavy chain constant region which has reduced binding to a Fcγ receptor relative to the natural human heavy chain constant region.

34. The method of claim 32, wherein the mature heavy chain variable region is fused to a heavy chain constant region having the sequence of SEQ ID NO:26 and/or the mature light chain variable region is fused to a light chain constant region having the sequence of SEQ ID NO:28.

\* \* \* \* \*